(12) United States Patent
Kincaid et al.

(10) Patent No.: US 12,065,439 B2
(45) Date of Patent: Aug. 20, 2024

(54) PYRROLOPYRIDINE-ANILINE COMPOUNDS FOR TREATMENT OF DERMAL DISORDERS

(71) Applicant: NFLECTION THERAPEUTICS, INC., BOSTON, MA (US)

(72) Inventors: John Kincaid, Boston, MA (US); Matthew Duncton, Boston, MA (US)

(73) Assignee: NFLECTION THERAPEUTICS, INC., Boston, MA (US)

( * ) Notice: Subject to any disclaimer, the term of this patent is extended or adjusted under 35 U.S.C. 154(b) by 446 days.

(21) Appl. No.: 17/399,661

(22) Filed: Aug. 11, 2021

(65) Prior Publication Data

US 2022/0033399 A1 Feb. 3, 2022

Related U.S. Application Data

(62) Division of application No. 16/615,086, filed as application No. PCT/US2018/033547 on May 18, 2018, now Pat. No. 11,161,845.

(60) Provisional application No. 62/508,997, filed on May 19, 2017, provisional application No. 62/663,202, filed on Apr. 26, 2018.

(51) Int. Cl.
C07D 471/04 (2006.01)
A61P 35/00 (2006.01)

(52) U.S. Cl.
CPC ............ *C07D 471/04* (2013.01); *A61P 35/00* (2018.01)

(58) Field of Classification Search
CPC ............................... C07D 471/04; A61P 35/00
See application file for complete search history.

(56) References Cited

U.S. PATENT DOCUMENTS

| 11,161,845 B2 | 11/2021 | Kincaid et al. |
| 2013/0345181 A1 | 12/2013 | Bavetsias et al. |

FOREIGN PATENT DOCUMENTS

| CN | 105384754 A | 3/2016 |
| WO | WO-2006/130160 | 12/2006 |
| WO | WO-2007/002433 | 1/2007 |
| WO | WO-2007/088345 | 8/2007 |
| WO | WO-2008/020206 | 2/2008 |
| WO | WO-2008/024724 | 2/2008 |
| WO | WO-2008/024725 | 2/2008 |
| WO | WO-2008/055236 | 5/2008 |
| WO | WO-2008/067481 | 6/2008 |
| WO | WO-2008/148034 | 12/2008 |
| WO | WO-2009/082687 | 7/2009 |
| WO | WO-2009/093008 | 7/2009 |
| WO | WO-2009/093009 | 7/2009 |
| WO | WO-2009/093013 | 7/2009 |
| WO | WO-2009/153554 | 12/2009 |
| WO | WO-2012/040636 | 3/2012 |
| WO | WO-2014/179785 | 11/2014 |

OTHER PUBLICATIONS

Adams et al., "Design and Synthesis of Orally Available MEK Inhibitors With Potent in Vivo Antitumor Efficacy," Bioorganic & Medicinal Chemistry Letters, 22(7), pp. 2411-2414 (2012).
Akinleye et al., "MEK and the Inhibitors: From Bench to Bedside," Journal of Hematology & Oncology, 6(27), 11 pages (2013).
Hatzivassiliou et al., "Mechanism of MEK inhibition determines efficacy in mutant KRAS-versus BRAF-driven cancers," Nature, 501(7466), pp. 232-236 (2013).
International Search Report and Written Opinion for International PCT Application No. PCT/US2018/033544 mailed Aug. 9, 2018 (11 pages).
International Search Report and Written Opinion for International PCT Application No. PCT/US2018/033547, mailed Aug. 9, 2018 (11 pages).
Laing et al., "Fused Thiophene Derivatives as MEK Inhibitors," Bioorganic & Medicinal Chemistry Letters, 22(1), pp. 472-475 (2012).
Wallace et al., "Structure-based Design and Synthesis of Pyrrole Derivatives as MEK Inhibitors," Bioorganic & Medicinal Chemistry Letters, 20(14), pp. 4156-4158 (2010).
RN 1347327-80-3 Registry ED Entered STN: Dec. 2, 2011.
RN 1347341-78-9 Registry ED Entered STN: Dec. 2, 2011.
RN 1347421-15-1 Registry ED Entered STN: Dec. 2, 2011.
RN 1348075-68-2 Registry ED Entered STN: Dec. 4, 2011.
RN 1348201-64-8 Registry ED Entered STN: Dec. 4, 2011.
RN 1348347-40-9 Registry ED Entered STN: Dec. 4, 2011.
RN 1348375-35-8 Registry ED Entered STN: Dec. 4, 2011.
RN 1348394-69-3 Registry ED Entered STN: Dec. 4, 2011.
RN 1348492-53-4 Registry ED Entered STN: Dec. 4, 2011.
RN 1348494-88-1 Registry ED Entered STN: Dec. 4, 2011.
RN 1348595-42-5 Registry ED Entered STN: Dec. 4, 2011.
RN 1348618-58-5 Registry ED Entered STN: Dec. 4, 2011.
RN 1348655-12-8 Registry ED Entered STN: Dec. 4, 2011.
RN 1348673-54-0 Registry ED Entered STN: Dec. 4, 2011.
RN 1349147-82-5 Registry ED Entered STN: Dec. 5, 2011.

(Continued)

*Primary Examiner* — Timothy R Rozof
(74) *Attorney, Agent, or Firm* — Mintz Levin Cohn Ferris Glovsky & Popeo, P.C.

(57) ABSTRACT

Provided herein are compounds, pharmaceutical compositions comprising the compounds, methods of preparing the compounds, and methods of using the compounds and compositions in treating diseases or disorders in a subject where the subject is in need of an inhibitor of MEK where the compound is according to Formula (I):

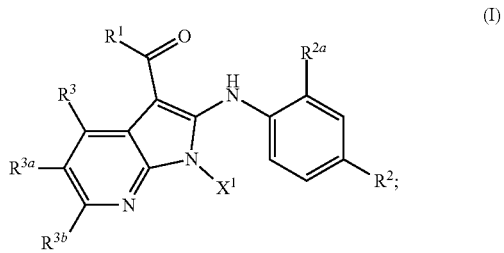

wherein $X^1$, $R^1$, $R^2$, $R^{2a}$, $R^3$, $R^{3a}$, and $R^{3b}$ are as described herein.

33 Claims, 4 Drawing Sheets

(56) References Cited

OTHER PUBLICATIONS

RN 1349255-80-6 Registry ED Entered STN: Dec. 5, 2011.
RN 1349369-24-9 Registry ED Entered STN: Dec. 6, 2011.
RN 1349383-92-1 Registry ED Entered STN: Dec. 6, 2011.
RN 1349420-35-4 Registry ED Entered STN: Dec. 6, 2011.
RN 1349476-92-1 Registry ED Entered STN: Dec. 6, 2011.
RN 1349510-77-5 Registry ED Entered STN: Dec. 6, 2011.
RN 1349524-53-3 Registry ED Entered STN: Dec. 6, 2011.
RN 1349623-68-2 Registry ED Entered STN: Dec. 6, 2011.
RN 1349668-73-0 Registry Ed Entered STN: Dec. 6, 2011.
RN 1349887-30-4 Registry ED Entered STN: Dec. 6, 2011.
RN 1349985-90-5 Registry ED Entered STN: Dec. 7, 2011.

Figure 1a and 1b. Suppression of pERK by Compound of Ex. 2 in Human Neurofibroma Explants Figure 2. Suppression of p-ERK in Human Cutaneous Neurofibroma (cNF) Explants with 500 nM of Compound of Example 2
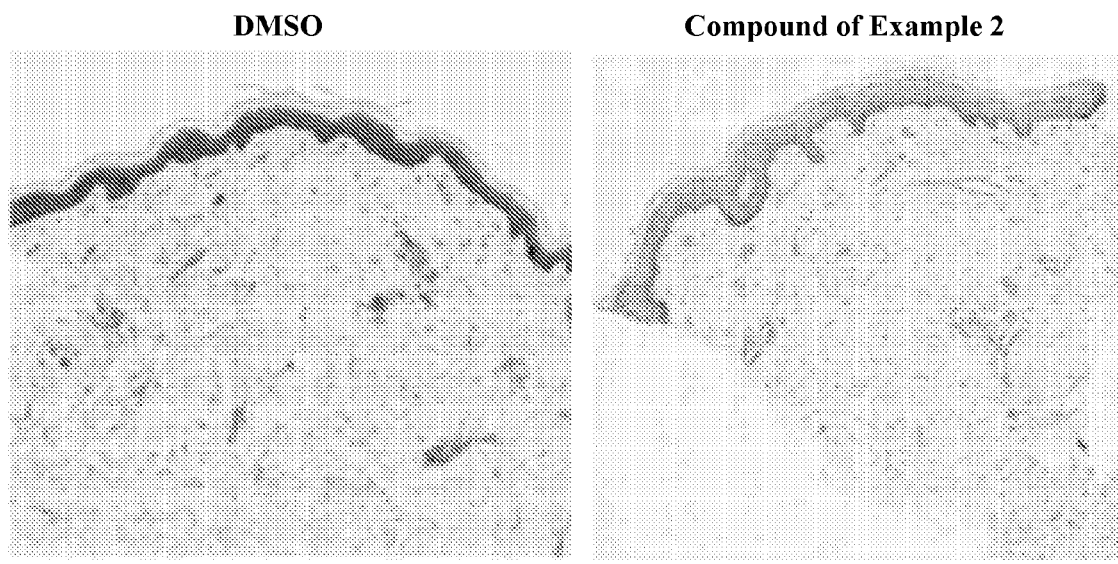

Figure 3. Dose Dependent Suppression of p-ERK with Compound of Example 2 in Human cNF Explants
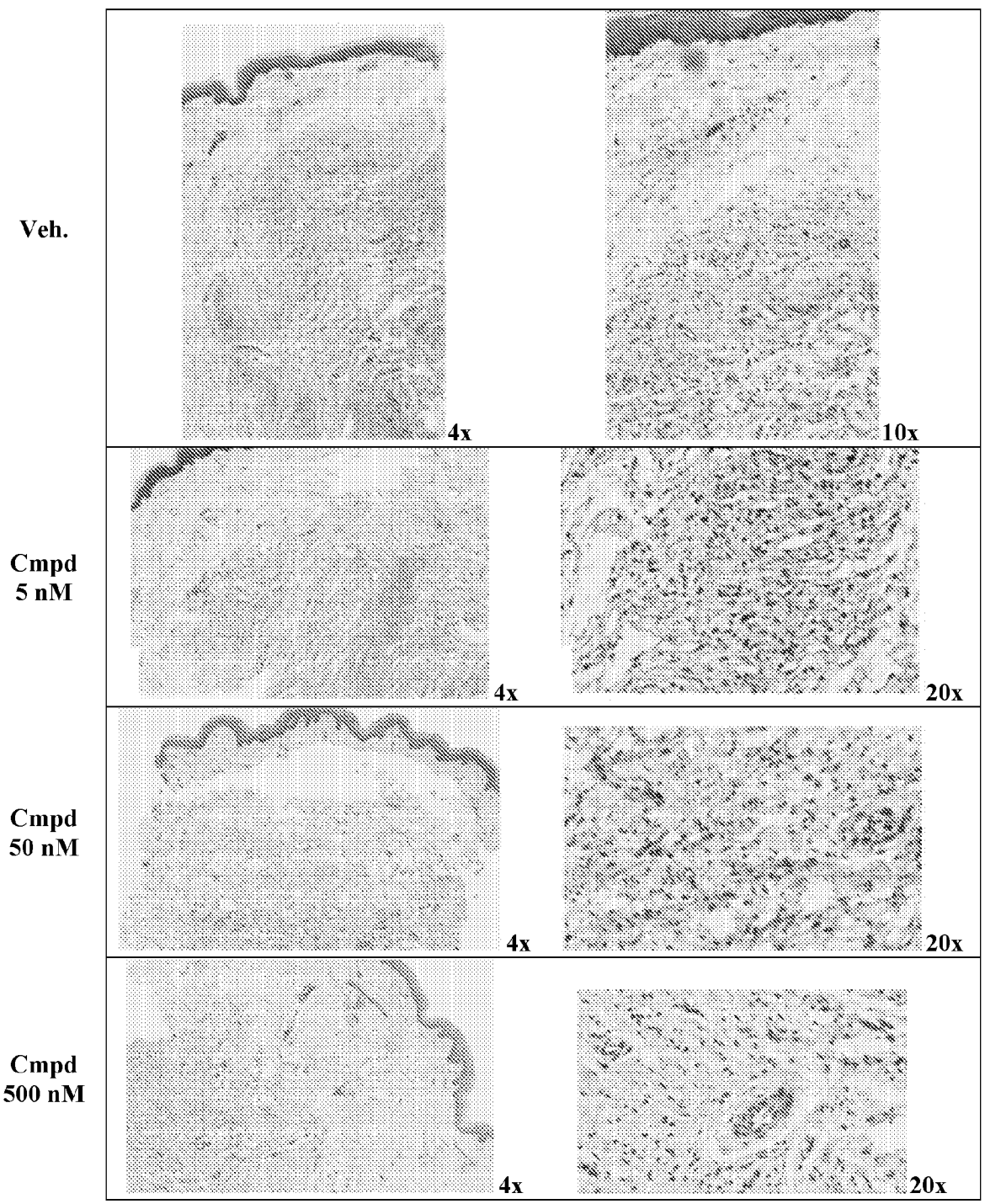

Figure 4. Suppression of p-ERK After Application of a Topical Gel Comprising a Compound of Example 2 in Human cNF Explants
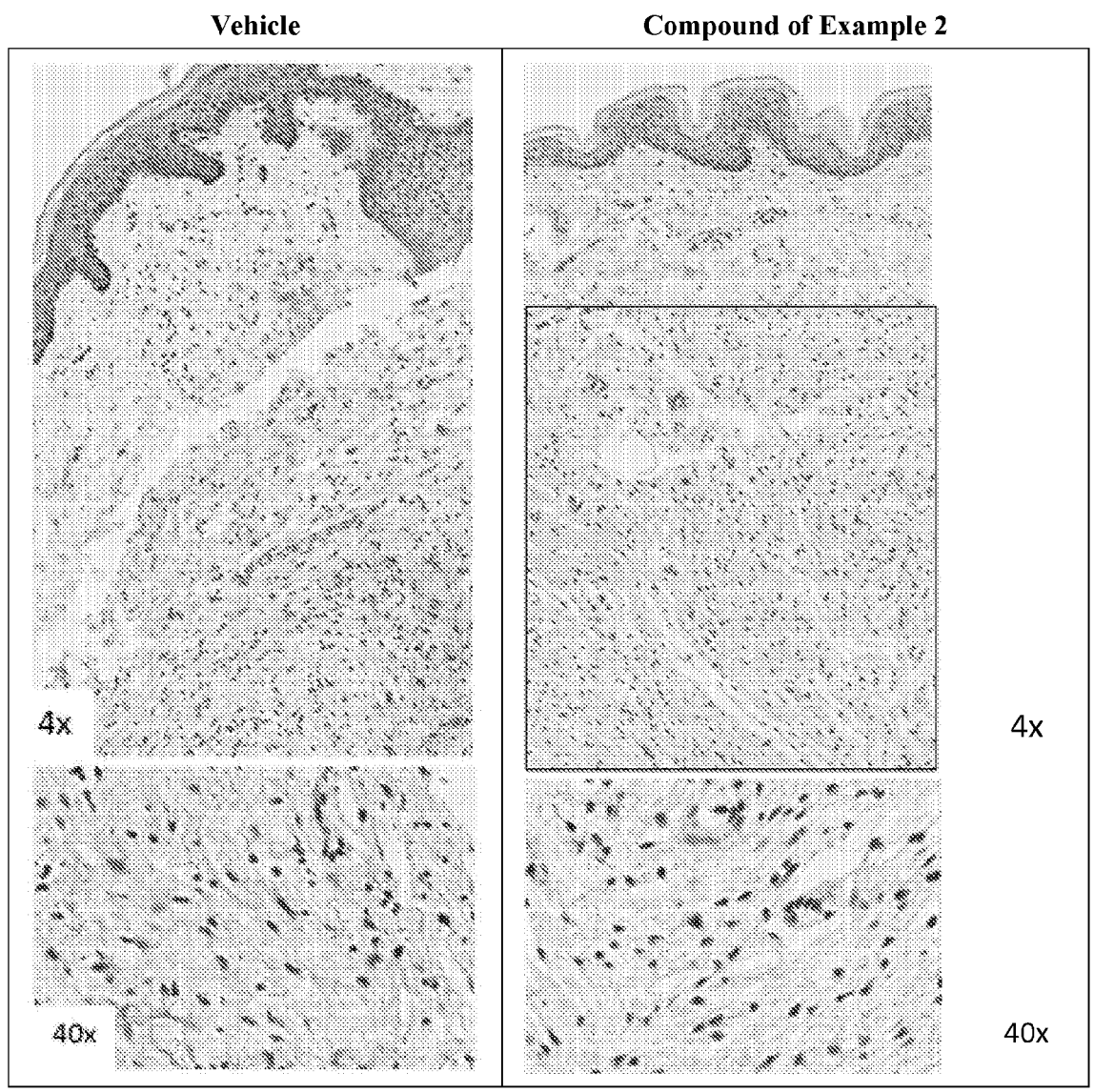

PYRROLOPYRIDINE-ANILINE COMPOUNDS FOR TREATMENT OF DERMAL DISORDERS

CROSS-REFERENCE TO RELATED APPLICATIONS

This application is a Divisional of U.S. patent application Ser. No. 16/615,086 filed Nov. 19, 2019, which is a U.S. National Phase Application of PCT International Application No. PCT/US2018/033547 filed May 18, 2018, which claims the benefit of priority to U.S. Provisional Application No. 62/508,997 filed on May 19, 2017 and U.S. Provisional Application No. 62/663,202 filed on Apr. 26, 2018, each of which is incorporated herein in its entirety for all purposes.

FIELD

Provided herein are compounds, pharmaceutical compositions comprising the compounds, and methods of using the compounds and compositions that are useful in treating dermal diseases or dermal disorders associated therewith. Also provided herein are methods of treating diseases or disorders in a mammal comprising administering a therapeutically or prophylactically effective amount of a compound or composition disclosed herein to a mammal.

BACKGROUND

Neurofibromatosis type 1 (NF1) occurs in approximately 1:3,500 births, and is one of the most common autosomal dominant single-gene disorders affecting neurological function in humans. Clinically, NF1 disease is characterized by the presence of benign peripheral nerve tumors, called neurofibromas, involving Schwann cells with biallelic mutations in the NF1 gene, as well as other tumor and non-tumor manifestations. (Jousma et al. *Pediatr. Blood Cancer* 62: 1709-1716, 2015). NF1 is associated with several dermal disorders, including dermal neurofibromas or cutaneous neurofibromas; plexiform neurofibromas; café au lait spots; and axillary and inguinal freckling. Dermal neurofibromas or cutaneous neurofibromas occur in over 95% of NF1 patients, can appear anywhere on the body, causing itching, irritation, infection, physical pain, and disfigurement. Moreover, dermal neurofibromas or cutaneous neurofibromas are associated with social isolation and anxiety.

NF1 is caused by one or more germ line mutations in NF1, a gene that inactivates the RAS pathway. Because the NF1 gene encodes a Ras-GAP protein, NF1 loss results in high Ras-GTP. Therefore, NF1 research has focused intensively on testing inhibitors in the Ras signaling pathway, including the Ras-MAPK cascade. (Jousma et al. *Pediatr. Blood Cancer* 62: 1709-1716, 2015). Four distinct MAPK cascades have been identified and named according to their MAPK module. (Akinleye et al. *Journal of Hematology & Oncology* 6:27, 2013). MEK proteins belong to a family of enzymes that lie upstream to their specific MAPK targets in each of the four MAP kinase signaling pathways. Two of these MEK proteins, MEK1 and MEK2, are closely related and participate in this signaling pathway cascade. Inhibitors of MEK1 and MEK2 have been shown to effectively inhibit MEK signaling downstream of Ras, and thus provide a rationale for targeting MEK in the treatment of NF1. (Rice et al. *Medicinal Chemistry Letters* 3:416-421, 2012).

Currently available MEK inhibitors are designed to have oral bioavailability for systemic delivery, and are associated with significant side effects including decreased left ventricular ejection fraction, elevated creatine phosphokinase, pneumonitis, renal failure, diarrhea, infection, urticaria, and maculo-papular rash, all of which are dose limiting or require permanent discontinuation. Moreover, clinical trials have shown side effects with prolonged high-dose administration of MEK inhibitors. (Huang et al. *J. Ocul. Pharmacol. Ther.* 25:519-530, 2009). For example, PD0325901, a clinically-tested MEK inhibitor, has exhibited neurological side effects associated with ataxia, confusion, and syncope. In addition, a number of other side effects have been observed with systemic exposure to MEK inhibitors including: acneiform rash, CPK elevation, nausea, vomiting, diarrhea, abdominal pain, and fatigue. Thus, there is a need for therapies that inhibit MEK to treat NF1 associated dermal neurofibromas or cutaneous neurofibromas, which limit one or more of these serious side effects.

SUMMARY

Provided herein are compounds, pharmaceutical compositions comprising the compounds, and methods of using the compounds and compositions for treating dermal diseases or dermal disorders associated therewith. Also provided herein are methods of treating diseases or disorders in a mammal comprising administering a therapeutically or prophylactically effective amount of a compound or composition disclosed herein to a mammal. In an embodiment, the mammal is a human.

In one aspect, provided is a Compound of Formula (I):

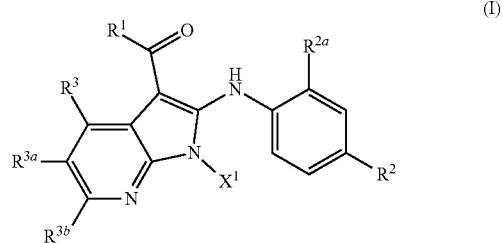

where
$R^1$ is $-OR^4$, $-NR^5R^{5a}$, or an N-linked heterocycloalkyl where the N-linked heterocycloalkyl is optionally substituted with one or two $R^{10}$;
$R^{2a}$ is halo or $C_1$-$C_6$ alkyl;
$R^2$ is $-S-C_1$-$C_6$ alkyl, $C_1$-$C_6$ alkyl, $C_2$-$C_6$ alkenyl, $C_2$-$C_6$ alkynyl, or halo;
$X^1$ is $C_1$-$C_6$-alkyl;
$R^3$, $R^{3a}$, and $R^{3b}$ are independently hydrogen, $C_1$-$C_6$ alkyl, $C_2$-$C_6$ alkenyl, $C_2$-$C_6$ alkynyl, $-S-C_1$-$C_6$ alkyl, halo, $C_1$-$C_6$-alkoxy; $C_3$-$C_8$-cycloalkyloxy; heterocycloalkyloxy; heteroaryloxy, or phenoxy where each phenyl and heteroaryl is independently optionally substituted with 1, 2, or 3 $R^6$;
$R^4$ is $C_1$-$C_6$ alkyl, $C_3$-$C_8$ cycloalkyl, $C_3$-$C_8$ cycloalkylalkyl, $C_1$-$C_6$ hydroxyalkyl, or $C_1$-$C_6$ alkoxyalkyl;
$R^5$ is hydrogen; $C_1$-$C_6$ alkyl optionally substituted with one heterocycloalkyl; $C_3$-$C_8$ cycloalkyl; $C_3$-$C_8$ cycloalkyl-$C_1$-$C_6$-alkyl-; $C_1$-$C_6$ hydroxyalkyl; $C_1$-$C_6$ alkoxy-$C_1$-$C_6$-alkyl; or $-OR^{5b}$;
$R^{5a}$ is hydrogen or $C_1$-$C_6$ alkyl;
$R^{5b}$ is hydrogen, $C_1$-$C_6$ alkyl, $C_3$-$C_8$ cycloalkyl, $C_3$-$C_8$ cycloalkyl-$C_1$-$C_6$-alkyl, $C_1$-$C_6$ hydroxyalkyl, or $C_1$-$C_6$ alkoxy-$C_1$-$C_6$-alkyl;

each $R^6$ is independently selected from the group consisting of carboxy, $C_1$-$C_6$-alkoxycarbonyl, $C_1$-$C_6$-alkyl, $C_1$-$C_6$-haloalkyl, $C_1$-$C_6$-alkoxy-$C_1$-$C_6$-alkyl, $C_3$-$C_8$ cycloalkyl, heterocycloalkyl, —OC(O)R$^7$, —OS(O)$_2$R$^7$, —O—$C_1$-$C_6$-haloalkyl, $C_3$-$C_8$ cycloalkyloxy, heterocycloalkyloxy, aryloxy, heteroaryloxy, amino, $C_1$-$C_6$-alkylamino, di-$C_1$-$C_6$-alkylamino, —NR$^{8a}$S(O)$_2$R$^8$, —NR$^{8a}$C(O)R$^8$, —S(O)$_2$R$^8$, —S(O)$_2$NR$^{8a}$R$^8$, —C(O)R$^8$, —C(O)NR$^{8a}$R$^8$, and —$C_1$-$C_6$-alkylene-R$^{6a}$;

each $R^{6a}$ is independently selected from the group consisting of $C_3$-$C_8$ cycloalkyl, heterocycloalkyl, —NH$_2$, —NH($C_1$-$C_6$-alkyl), —N($C_1$-$C_6$-alkyl)$_2$, —NR$^{9a}$S(O)$_2$R$^9$, —NR$^{9a}$C(O)R$^9$, —S(O)$_2$R$^9$, —S(O)$_2$NR$^{9a}$R$^9$, —C(O)R$^9$, and —C(O)NR$^{9a}$R$^9$;

each $R^7$ is independently selected from the group consisting of amino, $C_1$-$C_6$-alkylamino, di-$C_1$-$C_6$-alkylamino, $C_1$-$C_6$ alkyl, $C_3$-$C_8$ cycloalkyl, $C_1$-$C_6$-alkoxy, heterocycloalkyl, aryl, and heteroaryl;

each $R^{8a}$ and $R^{9a}$ is independently H or $C_{1-6}$ alkyl;

each $R^8$ and $R^9$ is independently $C_1$-$C_6$ alkyl, aryl, heteroaryl, $C_3$-$C_8$ cycloalkyl, or heterocycloalkyl; and each $R^{10}$ is independently hydrogen, halo, hydroxy, oxo, $C_1$-$C_6$ alkyl, $C_1$-$C_6$-hydroxyalkyl, halo-$C_1$-$C_6$-alkyl, amino-$C_1$-$C_6$-alkyl, $C_1$-$C_6$-alkylamino-$C_1$-$C_6$-alkyl, di-$C_1$-$C_6$-alkylamino-$C_1$-$C_6$-alkyl, $C_1$-$C_6$-alkoxy, $C_3$-$C_8$ cycloalkyl, heterocycloalkyl, or heteroaryl;

or an N-oxide, a stereoisomer, mixture of stereoisomers, and/or a pharmaceutically acceptable salt thereof.

In another aspect, provided herein are pharmaceutical compositions, single unit dosage forms, and kits suitable for use in treating a MEK-inhibitor responsive disorder or disease, MEK-inhibitor responsive dermal disorder or disease, MEK-mediated disorder or disease, or a MEK-mediated dermal disorder or disease which comprise a therapeutically or prophylactically effective amount of a compound provided herein, e.g., of some or any of the embodiments, of Formula (I)-(Iu) and the claims, and compounds in Embodiment A.

In an aspect, a method of treatment of MEK-inhibitor responsive disorder or disease, MEK-inhibitor responsive dermal disorder or disease, MEK-mediated disorder or disease, or a MEK-mediated dermal disorder or disease is provided comprising administering to an individual in need thereof a therapeutically or prophylactically effective amount of a compound described herein, e.g., of some or any of the embodiments, of Formula (I)-(Iu) and the claims, and compounds in Embodiment A.

BRIEF DESCRIPTION OF THE DRAWINGS

FIG. 2. demonstrates the suppression of p-ERK in human cNF explants with 500 nM of the compound of Ex. 2, obtained according to Biological Example 7.

FIG. 3. demonstrates the dose-dependent suppression of p-ERK with the compound of Ex. 2 in human cNF explants, obtained according to Biological Example 7.

FIG. 4. demonstrates that p-ERK was suppressed after application of a topical gel comprising Compound of Ex. 2 in Human cNF Explants, obtained according to Biological Example 7.

DESCRIPTION OF EXEMPLARY EMBODIMENTS

Figure 1A:
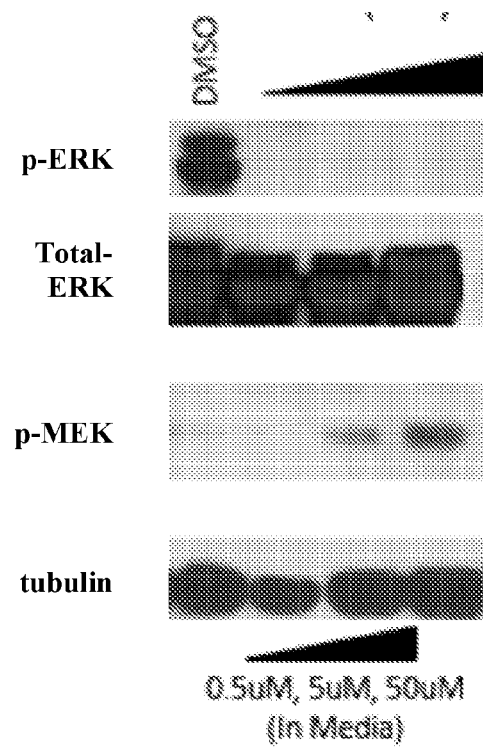
FIGS. 1a and 1b. demonstrate the suppression of pERK by the compound of Ex. 2 in human cutaneous neurofibroma (cNF) explants, obtained according to Biological Example 7.

Provided herein are compounds, pharmaceutical compositions comprising the compounds, and methods of using the compounds and compositions in the treatment of a MEK-inhibitor responsive disorder or disease, MEK-inhibitor responsive dermal disorder or disease, MEK-mediated disorder or disease, or a MEK-mediated dermal disorder or disease. Also provided herein are methods of treating a MEK-inhibitor responsive disorder or disease, MEK-inhibitor responsive dermal disorder or disease, MEK-mediated disorder or disease, or a MEK-mediated dermal disorder or disease in a mammal comprising administering a therapeutically or prophylactically effective amount of a compound or composition to a mammal. In an embodiment, the mammal is a human.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. Unless specified otherwise, where a term is defined as being substituted, the groups in the list of substituents are themselves unsubstituted. For example, a substituted alkyl group can be substituted, for example, with a cycloalkyl group, and the cycloalkyl group is not further substituted unless specified otherwise.

"Alkenyl," as used herein, unless otherwise specified, means a straight or branched hydrocarbon radical having at least one double bond. In certain embodiments, the alkenyl group includes two to ten carbon atoms, i.e., $C_2$ to $C_{10}$ alkenyl. In certain embodiments, the alkenyl is a $C_{2-6}$alkenyl. In some embodiments, alkenyl is ethenyl, propenyl, 1-but-3-enyl, 1-pent-3-enyl, or 1-hex-5-enyl.

"Alkynyl" means a straight or branched hydrocarbon radical having at least one triple bond. In certain embodiments, the alkynyl group includes two to ten carbon atoms, i.e., $C_2$ to $C_{10}$ alkyl. In certain embodiments, the alkynyl is a $C_{2-6}$alkyl. In some embodiments, alkynyl is ethynyl, propynyl, butynyl, pentyn-2-yl and the like.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl is a $C_{1-6}$alkyl. In certain embodiments, the alkyl group is selected from the group consisting of methyl, ethyl, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl.

The term "alkoxy," as used herein, and unless otherwise specified, refers to the group —OR' where R' is alkyl. Alkoxy groups include, in certain embodiments, methoxy, ethoxy, n-propoxy, isopropoxy, n-butoxy, tert-butoxy, sec-butoxy, n-pentoxy, n-hexoxy, 1,2-dimethylbutoxy, and the like.

The term "alkoxyalkyl," as used herein, and unless otherwise specified, refers to an alkyl group substituted with 1, 2, 3, or 4 alkoxy groups, as defined herein. In certain embodiments, the alkoxyalkyl is a alkoxy-$C_{1-6}$alkyl. In certain embodiments, the alkoxyalkyl is a $C_{1-6}$alkyl substituted with one, two, or three alkoxy, in some embodiments with one or two alkoxy, in some embodiments with one alkoxy.

The term "alkoxycarbonyl," as used herein, and unless otherwise specified, refers to a —C(O)R group where R is alkoxy, as defined herein.

The term "alkylamino," as used herein, and unless otherwise specified, means a —NHR radical where R is alkyl as defined herein, or an N-oxide derivative thereof. In some embodiments, alkylamino is methylamino, ethylamino, n-, iso-propylamino, n-, iso-, tert-butylamino, or methylamino-N-oxide, and the like.

The term "alkylthio," as used herein, and unless otherwise specified, refers to the group —SR' where R' is $C_{1-10}$alkyl. In some embodiments, alkylthio is $C_{1-6}$alkylthio. In some embodiments, alkylthio is methylthio.

The term "amino," as used herein, and unless otherwise specified, means a —$NH_2$.

The term "aryl," as used herein, and unless otherwise specified, means a monovalent six- to fourteen-membered, mono- or bi-carbocyclic ring, wherein the monocyclic ring is aromatic and at least one of the rings in the bicyclic ring is aromatic. In some embodiments, aryl is phenyl, naphthyl, or indanyl.

The term "aminoalkyl," as used herein, unless otherwise specified, refers to an alkyl group substituted with one or two $NH_2$.

The term "alkylaminoalkyl," as used herein, unless otherwise specified, refers to an alkyl group substituted with one or two —NH(alkyl) groups.

The term "dialkylaminoalkyl," as used herein, unless otherwise specified, refers to an alkyl group substituted with one or two —N(alkyl)$_2$ groups.

The term "aryloxy," as used herein, unless otherwise specified, refers to a —OR group where R is aryl as defined herein.

The term "cycloalkyl," as used herein, unless otherwise specified, refers to a monovalent, saturated or partially unsaturated (but not aromatic) mono or multi-cyclic hydrocarbon. In certain embodiments, the cycloalkyl group may be a bridged or non-bridged, spirocyclic or not spirocyclic, and/or fused or not fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), from 3 to 8 ($C_{3-8}$), or from 3 to 7 ($C_{3-7}$) carbon atoms. In certain embodiments, the cycloalkyl group is monocyclic or bicyclic. In certain embodiments, the cycloalkyl group is monocyclic. In certain embodiments, the cycloalkyl group is bicyclic. In certain embodiments, the cycloalkyl group is tricyclic. In certain embodiments, the cycloalkyl group is fully saturated. In certain embodiments, the cycloalkyl group is partially unsaturated. In certain embodiments, the cycloalkyl group is cyclopropyl, cyclobutyl, cyclopentyl, cyclohexyl, cycloheptyl, bicyclo[2.1.1]hexyl, bicyclo[2.2.1]heptyl, decalinyl or adamantyl.

The term "cycloalkylalkyl," as used herein, unless otherwise specified, refers to an alkyl group, as defined herein (in one embodiment, $C_1$-$C_6$), substituted with one or two cycloalkyl groups as defined herein.

The term "cycloalkyloxy," as used herein, unless otherwise specified, refers to a —OR group where R is cycloalkyl as defined herein.

The term "dialkylamino," as used herein, and unless otherwise specified, means an —NRR' radical where R and R' are independently alkyl as defined herein, and an N-oxide thereof. In some embodiments, dialkylamino is dimethylamino, diethylamino, N,N-methylpropylamino or N,N-methylethylamino, and the like.

The term "haloalkyl," as used herein, and unless otherwise specified, refers to an alkyl group substituted with 1, 2, 3, 4, or 5 halo groups. In certain embodiments, the haloalkyl is a halo-$C_{1-6}$alkyl.

The terms "halogen" and "halo," as used herein, and unless otherwise specified, are synonymous and refer to chloro, bromo, fluoro or iodo.

The term "heteroaryloxy," as used herein, unless otherwise specified, refers to a —OR group where R is heteroaryl as defined herein.

The term "heterocyclic," as used herein, and unless otherwise specified, refers to a monovalent monocyclic non-aromatic ring system and/or a multicyclic ring system that contains at least one non-aromatic ring; wherein one or more (in certain embodiments, 1, 2, 3, or 4) of the non-aromatic monocyclic ring atoms is a heteroatom independently selected from O, $S(O)_{0-2}$, and N, and the remaining ring atoms are carbon atoms; and wherein one or more (in certain embodiments, 1, 2, 3, or 4) of any of the ring atoms in the multicyclic ring system is a heteroatom(s) independently selected from O, $S(O)_{0-2}$, and N, and the remaining ring atoms are carbon. In certain embodiments, the heterocyclic ring comprises one or two heteroatom(s) which are nitrogen. In certain embodiments, heterocyclic is multicyclic and comprises one heteroatom in a non-aromatic ring, or comprises one heteroatom in an aromatic ring, or comprises two heteroatoms in an aromatic ring, or comprises two heteroatoms where one is in an aromatic ring and the other is in a non-aromatic ring. In certain embodiments, the heterocyclic group has from 3 to 20, 3 to 15, 3 to 10, 3 to 8, 4 to 7, or 5 to 6 ring atoms. In certain embodiments, the heterocyclic is a monocyclic, bicyclic, tricyclic, or tetracyclic ring system. In certain embodiments, the heterocyclic group may be a bridged or non-bridged, spirocyclic or not spirocyclic, and/or fused or not fused bicyclic group. One or more of the nitrogen and sulfur atoms may be optionally oxidized, one or more of the nitrogen atoms may be optionally quaternized, one or more of the carbon atoms may be optionally replaced with Some rings may be partially or fully saturated, or aromatic provided that heterocyclic is not fully aromatic. The monocyclic and multicyclic heterocyclic rings may be attached to the main structure at any heteroatom or carbon atom which results in a stable compound. The multicyclic heterocyclic may be attached to the main structure through any of its rings, including any aromatic or nonaromatic ring, regardless of whether the ring contains a heteroatom. In certain embodiments, heterocyclic is "heterocycloalkyl" which is 1) a saturated or partially unsaturated (but not aromatic) monovalent monocyclic heterocyclic group which contains at least one ring heteroatom, as described herein, or 2) a saturated or partially unsaturated (but not aromatic) monovalent bi- or tri-cyclic heterocyclic group in which at least one ring contains at least one heteroatom as described herein. In certain embodiments, heterocyclic is "heteroaryl" which is an aromatic heterocyclic containing at least one ring heteroatom, as described herein. When heterocyclic, heteroaryl, and heterocycloalkyl are substituted, they can be substituted on any ring, i.e. on any aromatic or nonaromatic ring comprised by heterocyclic, heteroaryl, and heterocycloalkyl. In certain embodiments, such heterocyclic includes, but are not limited to, imidazolyl, thienyl, furyl, pyrazolyl, pyrrolyl, thiazolyl, oxazolyl, oxadiazolyl, pyridyl, pyrimidinyl, pyridazinyl, pyrazinyl, quinolinyl, azepinyl, benzodioxanyl, benzodioxolyl, benzofuranonyl, benzopyranonyl, benzopyranyl, dihydrobenzofuranyl, benzotetrahydrothienyl, benzothiopyranyl, benzoxazinyl, O-carbolinyl, chromanyl, chromonyl, cinnolinyl, coumarinyl, decahydroquinolinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, 2,4-dioxo-imidazolidinyl, imidazolinyl, indolinyl, 2-oxo-indolinyl, isobenzotetrahydrofuranyl, isobenzotetrahydrothienyl, isochromanyl, isocoumarinyl, isoindolinyl, 1-oxo-isoindolinyl, 1,3-dioxo-isoindolinyl, isothiazolidinyl, isoxazolidinyl, 3-oxo-isoxazolidinyl, morpholinyl, 3,5-dioxo-morpholinyl, octahydroindolyl, octahydroisoindolyl, 1-oxo-octahydroisoindolyl, 1,3-dioxo-hexahydroisoindolyl, oxazolidinonyl, oxazolidinyl, oxiranyl, piperazinyl, 2,6-dioxo-piperazinyl, piperidinyl, 2,6-dioxo-piperidinyl, 4-piperidonyl, pyrazolidinyl, pyrazolinyl, pyrrolidinyl, pyrrolinyl, 2-oxopyrrolidinyl, 2,5-dioxopyrrolidinyl, quinuclidinyl, tetrahydrofuryl, tetrahydroisoquinolinyl, tetrahydropyranyl, tetrahydrothienyl, thiamorpholinyl, thiomorpholinyl, 3,5-dioxo-thiomorpholinyl, thiazolidinyl, 2,4-dioxo-thiazolidinyl, tetrahydroquinolinyl, phenothiazinyl, phenoxazinyl, xanthenyl, and 1,3,5-trithianyl. In some or any embodiments, heterocyclic is benzo-1,4-dioxanyl, benzodioxolyl, indolinyl, 2-oxo-indolinyl, pyrrolidinyl, piperidinyl, 2,3-dihydrobenzofuranyl, or decahydroquinolinyl.

The term "heteroaryloxy," as used herein, unless otherwise specified, refers to a —OR group where R is heterocycloalkyl as defined herein.

The term "heterocycloalkyloxy," as used herein, unless otherwise specified, refers to a —OR group where R is heterocycloalkyl as defined herein.

The term "hydroxyalkyl," as used herein, and unless otherwise specified, refers to an alkyl group substituted with 1, 2, 3, or 4 hydroxy groups. In certain embodiments, the hydroxyalkyl is a hydroxy-$C_{1-6}$alkyl. In certain embodiments, the hydroxyalkyl is a $C_{1-6}$alkyl substituted with one, two, or three hydroxy, in some embodiments with one or two hydroxy, in some embodiments with one hydroxy.

The term "phenoxy," as used herein refers to an —OR group where R is phenyl as defined herein. The phenyl is optionally substituted as described herein.

The term "protecting group," as used herein, and unless otherwise specified, refers to a group that is added to an oxygen, nitrogen or phosphorus atom to prevent its further reaction or for other purposes. A wide variety of oxygen and nitrogen protecting groups are known to those skilled in the art of organic synthesis. (See for example those described in Greene, et al., Protective Groups in Organic Synthesis, John Wiley and Sons, Fourth Edition, 2006, hereby incorporated by reference.) In some embodiments, a nitrogen-protecting group (e.g. for $PG^1$ and $PG^2$) is 9-fluorenylmethyloxycarbonyl (Fmoc), tert-butoxycarbonyl (Boc), benzyloxycarbonyl (CBz), acetyl, trichloroacetyl, trifluoroacetyl, —C(O)OCH$_2$CCl$_3$ (Troc), p-methoxyphenyl, benzyl, p-methoxybenzyl, p-methoxybenzylcarbonyl, triphenylmethyl, benzylidenyl, 2,2,2-trichloroethoxysulfonyl (Tces), p-methoxybenzenesulfonyl (Mbs) or p-toluenesulfonyl (tosyl). In some embodiments, an oxygen-protecting group (e.g. for $X^1$) is methoxymethyl (MOM), ethoxyethyl, methoxyethoxymethyl, tetrahydrofuranyl, tetrahydropyranyl, methyl, tert-butyl, allyl, benzyl, trimethylsilyl, triethylsilyl, triisopropylsilyl, tert-butyldimethylsilyl, tert-butyldiphenylsilyl, acetyl, pivalyl, benzoyl, dimethoxytrityl, trityl, methoxytrityl, p-methoxybenzyl, or methylthiomethyl.

The term "pharmaceutically acceptable salt," as used herein, and unless otherwise specified, refers to any salt of a compound provided herein which retains its biological properties and which is not toxic or otherwise desirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; and (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, in certain embodiments, and without limitation, sodium, potassium, calcium, magnesium, ammonium, tetraalkylammonium salts and the like. When the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "substantially free of" or "substantially in the absence of" stereoisomers with respect to a composition refers to a composition that includes at least 85 or 90% by weight, in certain embodiments 95%, 98%, 99% or 100% by weight, of a designated stereoisomer of a compound in the composition. In certain embodiments, in the methods and compounds provided herein, the compounds are substantially free of stereoisomers.

Similarly, the term "isolated" with respect to a composition refers to a composition that includes at least 85, 90%, 95%, 98%, 99% to 100% by weight, of a specified compound, the remainder comprising other chemical species or stereoisomers.

The term "solvate," as used herein, and unless otherwise specified, refers to a compound provided herein or a salt thereof, that further includes a stoichiometric or non-stoichiometric amount of solvent bound by non-covalent intermolecular forces. Where the solvent is water, the solvate is a hydrate.

The term "isotopic composition," as used herein, and unless otherwise specified, refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopic enrichment," as used herein, and unless otherwise specified, refers to the percentage of incorporation of an amount of a specific isotope at a given atom in a molecule in the place of that atom's natural isotopic abundance. In certain embodiments, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

The term "isotopically enriched," as used herein, and unless otherwise specified, refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkoxy," "heterocycloalkyl," "heterocyclic," and "heteroaryl," groups optionally comprise deuterium at one or more positions where hydrogen atoms are present, and wherein the deuterium composition of the atom or atoms is other than the natural isotopic composition.

Also as used herein, "alkyl," "cycloalkyl," "alkoxy," "heterocycloalkyl," "heterocyclic," and "heteroaryl," groups optionally comprise carbon-13 at an amount other than the natural isotopic composition.

As used herein, and unless otherwise specified, the term "$IC_{50}$" refers to an amount, concentration or dosage of a particular test compound that achieves a 50% inhibition of a maximal response in an assay that measures such response.

As used herein, the terms "subject" and "patient" are used interchangeably. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and in certain embodiments, a human. In certain embodiments, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a condition, is sufficient to effect such treatment for the condition. A "therapeutically effective amount" can vary depending on, inter alia, the compound, the disease or disorder and its severity, the size of the lesion to be treated, and the age, weight, etc., of the subject to be treated.

"Treating" or "treatment" of any disease or disorder refers, in certain embodiments, to ameliorating a disease or disorder that exists in a subject, including prophylactically. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder. In yet another embodiment, "treating" or "treatment" includes the reduction or elimination of either the disease or disorder (e.g. MEK-inhibitor responsive disorder or disease, MEK-inhibitor responsive dermal disorder or disease, MEK-mediated disorder or disease, or a MEK-mediated dermal disorder or disease) or one or more symptoms (e.g. MEK-inhibitor responsive disorder or disease, MEK-inhibitor responsive dermal disorder or disease, MEK-mediated disorder or disease, or a MEK-mediated dermal disorder or disease) of the disease or disorder, or to retard the progression of the disease or disorder (e.g. MEK-inhibitor responsive disorder or disease, MEK-inhibitor responsive dermal disorder or disease, MEK-mediated disorder or disease, or a MEK-mediated dermal disorder or disease) or of one or more symptoms (e.g. MEK-inhibitor responsive disorder or disease, MEK-inhibitor responsive dermal disorder, MEK-mediated disorder or disease, or disease or a MEK-mediated dermal disorder or disease) of the disease or disorder, or to reduce the severity of the disease or disorder (e.g. MEK-inhibitor responsive disorder or disease, MEK-inhibitor responsive dermal disorder, MEK-mediated disorder or disease, or disease or a MEK-mediated dermal disorder or disease) or of one or more symptoms (e.g. MEK-inhibitor responsive disorder or disease, MEK-inhibitor responsive dermal disorder, MEK-mediated disorder or disease, or disease or a MEK-mediated dermal disorder or disease) of the disease or disorder. In yet another embodiment, "treating" or "treatment" includes administering a compound described herein prophylactically.

"Topical" means application of a suitable compound (e.g. active agent) or composition comprising a compound (e.g. active agent) to the skin to treat or prevent a disease or a lesion of the skin. "Transdermal" means application of a suitable compound (e.g. active agent) or composition comprising a compound (e.g. active agent) to the skin such that the active agent may penetrate the layers in the skin to reach beyond the dermal or hypodermal layers, including, for example, systemic delivery. "Subcutaneous" means application of a suitable compound (e.g. active agent) or composition comprising a compound (e.g. active agent) to the layers below the epidermis and dermis. "Intradermal" means application of a suitable compound (e.g. active agent) or composition comprising a compound (e.g. active agent) in the dermal or hypodermal layers. "Intralesional" means injection of a suitable compound (e.g. active agent) or composition comprising a compound (e.g. active agent) at the site of the lesion.

In some embodiments, "topical" means application of a suitable compound (e.g. active agent) or composition comprising a compound (e.g. active agent) to the skin with adequate penetration of the epidermis or dermis to treat or prevent a lesion or a disease of the epidermis and/or dermis. In some embodiments of topical application, the compound or composition penetrates the epidermis or dermis without significant systemic exposure nor intent to treat or prevent a disease of another organ system. In some embodiments, "transdermal" means application of a suitable compound (e.g. active agent) or composition comprising a compound (e.g. active agent) to the skin with the objective of obtaining systemic therapeutic levels. In some embodiments of transdermal application, the active agent will penetrate the layers in the skin to reach beyond the dermal or hypodermal layers, including, for example, systemic delivery. In some embodiments, "subcutaneous" means injection of a suitable compound (e.g. active agent) or composition comprising a compound (e.g. active agent) into the layers below the epidermis and dermis. In some embodiments, "intradermal" means injection of a compound (e.g. active agent) or composition comprising a compound (e.g. active agent) into the dermal layers with the objective of obtaining systemic therapeutic levels. In some embodiments, "intralesional" means injection of a compound (e.g. active agent) or composition comprising a compound (e.g. active agent) directly into a lesion, such as a tumor or diseased tissue, with the objective of treating or preventing a disease or a lesion.

Distinctiveness and Advantages of the Compounds of the Present Application

WO 2008067481 discloses MEK inhibitors having the following motif:

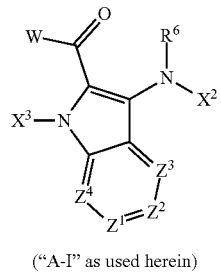

("A-I" as used herein)

where $Z^4$ can be N and $Z^1$ to $Z^3$ can be $CR^1$, among other possibilities. In addition, WO 2008067481 discloses the formula:

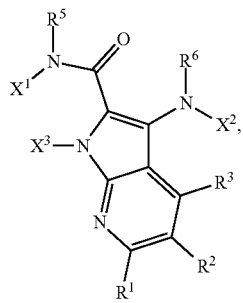

("A-Id" as used herein)

as one of at least twenty-seven sub-genuses.

There are important differences between WO 2008067481 and the present application. The compounds in WO 2008067481 have a different substitution pattern on the pyrrolopyridine core from the compounds of the present application. Notably the —C(O)W group in A-I is at the 2-position of the pyrrolopyridine ring and the —N($R^6$)($X^2$) substituent is at the 3-position of the pyrrolopyridine ring. In Applicant's compounds, these positions are reversed.

While WO 2008067481 discloses compounds such as Compound C8 (as numbered in the present application), no specific compounds in WO 2008067481 fall within the scope of the A-Id genus, i.e. where the nitrogen in the pyridine portion of the pyrrolopyridine ring is at the 7-position. No synthetic schemes are provided in WO 2008067481, showing how to make compounds of the genus (A-Id), much less showing how to make compounds with Applicant's substitution pattern. In fact, Applicant surprisingly found no compounds and no preparation methods in the art with Applicant's substitution pattern, i.e. 1H-pyrrolo[2,3-b]pyridines with an aniline at the 2-position and an acid, amide, or ester at the 3-position.

Other references disclose different pyrrolopyridines, such as WO 2009082687 which provides compounds of the following formulas:

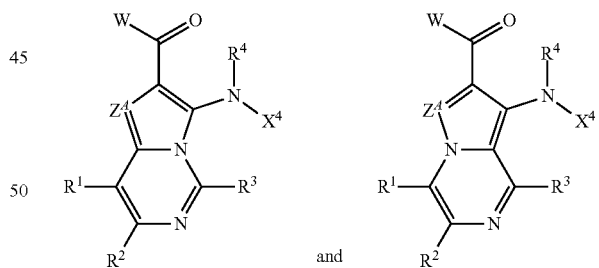

where $Z^A$ can be $CR^A$ or N. Notably, the compounds in WO 2009082687 have a different substitution pattern on the pyrrolopyridine core from the compounds of the present application. The —C(O)W group in in the above formulas is at the 2-position of the pyrrolopyridine ring and the —N($R^4$)($X^4$) substituent is at the 3-position of the pyrrolopyridine ring. In Applicant's compounds, these positions are reversed. In addition, there is no substitutable nitrogen in the pyrrolopyridine ring in the above formulas. Applicant's compounds have been designed to have the nitrogen of the pyrrole of the pyrrolopyridine ring substituted with an alkyl group. Compounds of the invention can undergo a metabolic transformation wherein the alkyl group is removed by metabolizing enzymes ("N-dealkylation"). Compounds of the invention can also undergo a deactivating metabolic transformation, leading to decarboxylation at the 3-position of the pyrrolopyridine core, e.g.,

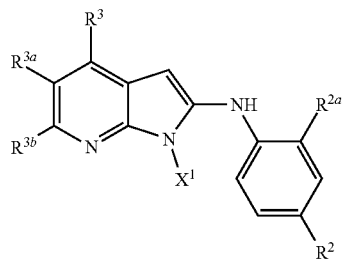

This metabolic transformation is not possible in compounds of WO 2008067481 since the 3-positon does not contain a carboxylate group but rather an aniline moiety. Applicant's compound's therefore have one or more metabolic routes of elimination from peripheral circulation not present in compounds from WO 2009082687. The importance of additional elimination routes of compounds of Applicant's invention is discussed below.

In addition to the structural differences disclosed above, the compounds of the present application are designed to be used in a different and unexpected way compared to compounds in the MEK art. The historical focus of MEK inhibitor discovery and development has been to make orally bioavailable compounds with sufficient in vivo stability to inhibit the MEK1 enzyme in tumors using an acceptable oral dosing regimen, thus favoring the selection of compounds with metabolic stability.

Consistent with the goal in the art to provide stable MEK compounds, the development of CI-1040, a MEK inhibitor formerly in clinical trials, was terminated in part due to its unfavorable stability. A compound of much greater metabolic stability, PD-0325901, was chosen for further development. A published account of this states "CI-1040 suffered however from poor exposure due to its poor solubility and rapid clearance, and as a result, development of the compound was terminated." (Barret et al., *Bioorganic & Medicinal Chemistry Letters* 2008, 18, 6501-6504). Other literature accounts of MEK inhibitor discovery demonstrate that optimization of metabolic stability was a goal of identifying compounds for clinical use. Finally, the FDA-approved trametinib is significantly stable to metabolism leading to a remarkable half-life in humans of 3.9 to 4.8 days (see Infante et al. *The Lancet* 2012, Vol 13(8), 773-78; also drug label, available at accessdata.fda.gov/drugsatfda_docs/label/2013/204114s000lbl.pdf).

It is clear, from the above accounts of MEK inhibitor discovery and development, that high systemic clearance, as measured by microsomal stability (or some other assay routinely used in the art) or rodent in vivo pharmacokinetic experiments, has been an undesired characteristic leading to the discontinuation of certain compounds and the further optimization of such compounds to provide for enhanced metabolic stability. In contrast, Applicant provides compounds which are designed to have significant metabolic lability.

Table 1 below provides half-life in human liver S9 fractions for a number of compounds in the MEK art, as well as a compound of the present application. The data in Table 1 were generated at the Applicant's request using the assay in Biological Example 3 using human liver S9 fraction. As evident from the data, the half-life in human liver S9 fractions varies considerably across the compounds.

TABLE 1

| Compound | Liver S9 t$_{1/2}$ (min) | CLint (μL/min/mg protein) |
|---|---|---|
| CI-1040 | 33 | 10.37 |

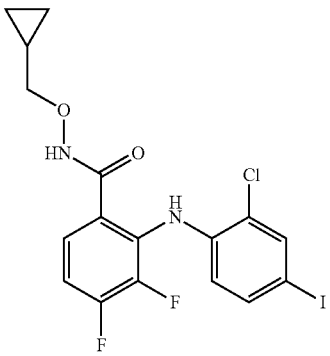 [SMILES: O=C(NOCC1CC1)c1ccc(F)c(F)c1Nc1ccc(I)cc1Cl]

TABLE 1-continued

| Compound | Liver S9 $t_{1/2}$ (min) | CLint (μL/min/mg protein) |
|---|---|---|
| PD-0325901 | 340 | 1.02 |
| Binemetinib | 277 | 1.25 |
| Selumetinib | 138 | 2.50 |
| GDC-0623 | 50 | 6.98 |

TABLE 1-continued

| Compound | Liver S9 $t_{1/2}$ (min) | CLint (μL/min/mg protein) |
| --- | --- | --- |
| Trametinib | 402 | 0.86 |
| Pimasertib | 268 | 1.29 |
| Compound C8 | 66 | 5.27 |
| Compond C9 | 158 | 2.20 |

TABLE 1-continued

| Compound | Liver S9 $t_{1/2}$ (min) | CLint (μL/min/mg protein) |
|---|---|---|
| A compound the present application (Ex. 2) 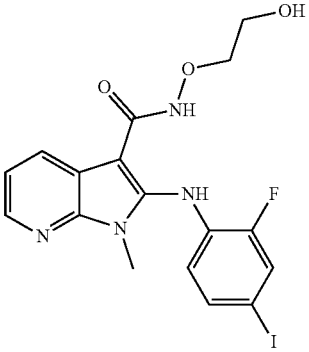 [SMILES: Cn1c(Nc2ccc(I)cc2F)c(C(=O)NOCCO)c2cccnc21] | 16 | 21.45 |
| A compound the present application (Ex. 7) 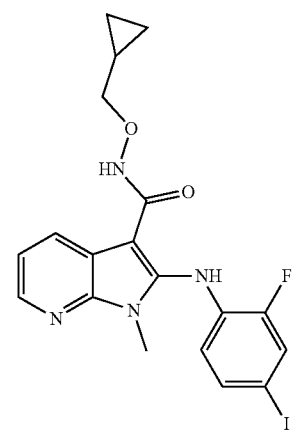 [SMILES: Cn1c(Nc2ccc(I)cc2F)c(C(=O)NOCC2CC2)c2cccnc21] | 8 | 44.80 |

In sharp contrast to the art compounds, the compounds of the present application are designed for topical, subcutaneous, intradermal, or intralesional application, resulting in inhibition of MEK activity in the dermal and epidermal layers (or in the lesion) for treatment of certain dermal disorders. After acting to treat the skin or lesion, in some embodiments, the compound is designed to be metabolically labile in order to limit systemic toxicity after topical, subcutaneous, transdermal, intradermal, or intralesional application by limiting the amount of time the compound remains in the peripheral circulation. The present application provides a solution for the treatment of dermal disorders with compounds which demonstrate the ability to penetrate the skin and suppress phospho-ERK.

In some embodiments, "soft MEK inhibitor" is a compound which inhibits MEK1 and/or 2 and is characterized by a predictable and controllable metabolism/degradation to non-toxic and biologically less active or inactive (i.e. does not inhibit, or inhibits to a lesser degree, MEK1 and/or 2) products after they have achieved their therapeutic role in the skin.

As used herein, "hard MEK inhibitor" refers to a MEK inhibitor known in the art. In an embodiment, a hard MEK inhibitor is designed for oral bioavailability. This is necessary to deliver therapeutically effective levels of MEK inhibitor to peripheral lesions with systemic delivery. In some embodiments, hard MEK inhibitors include, for example, PD0325901; PD184161; SMK-17; AS703026 (Pimasertib, MSC1936369); RO-4987655; Selumetinib (AZD6244, ARRY142886); Binimetinib (MEK162, ARRY-162, ARRY-438162); Refametinib; Cobimetinib (GDC-0973, XL518); GDC-0623; AZD8330 (ARRY-424704); trametinib; PD198306; and PD318088. In some embodiments, hard MEK inhibitors include, for example, PD0325901; AS703026 (Pimasertib, MSC1936369); Selumetinib (AZD6244, ARRY142886); Binimetinib (MEK162, ARRY-162, ARRY-438162); and trametinib.

While not wishing to be bound by theory, it is believed that soft MEK inhibitors, e.g., such as the "soft" MEK inhibitors described herein, are more metabolically labile than known "hard" MEK inhibitors. Due to their inherent metabolic instability, e.g., for degradation upon reaching the systemic circulation, "soft" MEK inhibitors, e.g., such as the "soft" MEK inhibitors described herein, are dermally active but have low systemic exposure upon local or non-systemic administration, e.g., topical, subcutaneous, transdermal, intradermal, or intralesional administration, because they may more rapidly degrade upon exposure to plasma or blood or hepatic metabolic enzymes. Unlike "soft" MEK inhibitors, known MEK inhibitors have been historically designed for good oral bioavailability, which requires good stability in plasma or blood and good stability to hepatic metabolism necessary to permit systemic delivery at therapeutically effective levels, and may be more prone to one or more unwanted side effects and increased toxicity. As a result, "soft" MEK inhibitors, e.g., such as the soft MEK inhibitors described herein, may be less systemically toxic.

In some embodiments, a soft Mek inhibitor has a half-life of less than or equal to about 90 minutes, less than or equal to about 75 minutes, less than or equal to about 60 minutes, less than or equal to about 55 minutes, less than or equal to about 50 minutes, less than or equal to about 45 minutes, less than or equal to about 40 minutes, less than or equal to about 35 minutes, less than or equal to about 30 minutes, less than or equal to about 25 minutes, less than or equal to about 20 minutes, less than or equal to about 15 minutes, or less than or equal to about 10 minutes. In some embodiments, a hard Mek inhibitor has a half-life of greater than or equal to about 90 minutes, greater than or equal to about 105 minutes, greater than or equal to about 2 hours, greater than or equal to about 2.5 hours, greater than or equal to about 3 hours, greater than or equal to about 5 hours, greater than or equal to about 8 hours, greater than or equal to about 10 hours, greater than or equal to about 16 hours, greater than or equal to about 24 hours, greater than or equal to about 36 hours, or greater than or equal to about 48 hours. In some embodiments, the hepatic metabolic half-life is measured using an assay such as substantially as described in Biological Example 3 or 4. In some embodiments, the hepatic metabolic half-life is measured using an assay such as substantially as described in Biological Example 3 using human liver S9 fraction.

In some or any embodiments, the term "dermal neurofibroma" is used interchangeably with "cutaneous neurofibroma." In some or any embodiments, the term "cutaneous neurofibroma" is an embodiment of "dermal neurofibroma."

The disclosure provides "soft" MEK inhibitors, compositions comprising "soft" MEK inhibitors, and methods of treating and/or preventing a dermal disorder (e.g., a MEK-inhibitor responsive dermal disorder or a MEK mediated dermal disorder, e.g., a dermal rasopathy, e.g., a dermal disorder associated with neurofibromatosis type 1 (NF1), e.g., a dermal neurofibroma, a cutaneous neurofibroma, a subdermal neurofibroma, or a superficial plexiform neurofibroma) with MEK inhibitors e.g., "soft" MEK inhibitors. For example, the methods described herein provide administration, e.g., local or non-systemic, e.g., topical, subcutaneous, transdermal, intradermal, or intralesional administration, of MEK inhibitors, e.g., "soft" MEK inhibitors, e.g., "soft" MEK inhibitors described herein, whereby one or more side effects exhibited with systemic exposure, e.g., known one or more side effects exhibited with MEK inhibitors designed for systemic delivery, are significantly reduced.

pKa can affect one or more of the following parameters: potency, selectivity, c log P, c log D, solubility, permeability, metabolism (i.e., ADMET), pharmacokinetics (bioavailability (% F), clearance (Cl), volume of distribution ($V_d$), and plasma protein binding); pharmacodynamics; efflux (e.g., Pgp); central nervous system permeability; blood-brain-barrier penetration; hERG binding; and phospholipidosis. Each of these parameters can be measured using procedures which are well-known to one of ordinary skill in the art, including those disclosed herein.

In some or any embodiments, the basic pKa of the pyridine nitrogen of a compound disclosed herein affects one or more of the following: potency, selectivity, c log P, c log D, solubility, permeability, metabolism (i.e., ADMET), pharmacokinetics (bioavailability (% F), clearance (Cl), volume of distribution ($V_d$), and plasma protein binding); pharmacodynamics; efflux (e.g., Pgp); central nervous system permeability; blood-brain-barrier penetration; hERG binding; and phospholipidosis. In certain embodiments, the pyridine nitrogen of a compound disclosed herein has a pKa value that modulates one or more of the following absorption, distribution, metabolism, excretion, toxicity, and permeability.

In some or any embodiments, the pyridine nitrogen of a compound disclosed herein has a pKa of about 5.5 of less, about 5 or less, about 4.5 or less, about 4 or less, or about 3.5 or less. In some or any embodiments, a compound disclosed herein has a pKa between about 3 and about 5.5, between about 3 and about 5, between about 3 and about 4.5, between about 3 and about 4, or between about 3.5 and about 4.

In some or any embodiments, the basic pKa of the pyridine nitrogen of a compound disclosed herein is calculated using Instant JChem, software available from Chemaxon.

In an embodiment, administering comprises contacting the soft MEK inhibitor with the skin of the subject, e.g., an affected region of the skin, e.g., a region of the skin having a tumor associated with neurofibromatosis type 1 (NF1), e.g., a dermal neurofibroma, a cutaneous neurofibroma, or a superficial plexiform neurofibroma, e.g., by local or non-systemic application, e.g., topical, subcutaneous, transdermal, intradermal or intralesional application, of the soft MEK inhibitor.

In an embodiment, administering comprises contacting the soft MEK inhibitor with the skin, mucous membranes, vagina, penis, larynx, vulva, cervix, or anus of the subject, by local or non-systemic application, e.g., topical, subcutaneous, transdermal, intradermal, or intralesional application or application by suppository, of the soft MEK inhibitor.

In an embodiment, the tumor associated with neurofibromatosis type 1 (NF1), e.g., a dermal neurofibroma, a cutaneous neurofibroma, a subdermal neurofibroma, or a superficial plexiform neurofibroma, is reduced, e.g., the size or the total tumor volume is reduced, by at least about 15% relative to the reference standard (e.g., from about 15% to about 60%), thereby treating the subject. In an embodiment, the reference standard is the size or the total tumor volume in an untreated control, e.g., from the same subject or a different subject.

In an embodiment, the size or total tumor volume of the tumor associated with neurofibromatosis type 1 (NF1), e.g., a dermal neurofibroma, a cutaneous neurofibroma, a subdermal neurofibroma, or a superficial plexiform neurofibroma, is reduced by at least about 15%, by at least about 20%, by at least about 25%, by at least about 30%, by at least about 35%, by at least about 40%, by at least about 45%, by at least about 50%, by at least about 55%, by at least about 60% relative to the reference standard. In an embodiment, the reference standard is the size or the total tumor volume in an untreated control, e.g., from the same subject or a different subject.

In an embodiment, the method comprises evaluating the subject with magnetic resonance imaging (MRI), or optical imaging, or high frequency ultrasound, or silicone mold, or calipers, e.g., evaluating the volume of tumors obtained from the subject, e.g., prior to, during and/or after treatment.

The compound as administered has a first level of MEK inhibition. After metabolism/degradation, a residue of the administered compound has a lower level of MEK inhibition (e.g., of at least about 2-fold lower, at least about 3-fold lower, at least about 4-fold lower, at least about 5-fold lower, at least about 10-fold lower, at least about 15-fold lower, at least about 20-fold lower, at least about 30-fold lower, at least about 40-fold lower, at least about 50 fold lower, at least about 60-fold lower, at least about 70-fold lower, at least about 80-fold lower, at least about 90-fold lower, at least about 100-fold lower, at least about 200-fold lower, at least about 500 fold lower, at least about 1,000-fold lower level of MEK inhibition, as compared to the compound before it is metabolized/degraded).

In an embodiment, after metabolism/degradation any residue of a compound disclosed herein has a lower level of MEK inhibition, e.g., of about 2-fold lower, about 3-fold lower, about 4-fold lower, about 5-fold lower, about 10-fold lower, about 20-fold lower, about 50 fold lower, about 100-fold lower, about 200-fold lower, about 500 fold lower, about 1,000-fold lower level of MEK inhibition, as compared to the compound before it is metabolized/degraded.

In certain such embodiment, after metabolism/degradation any residue of a compound disclosed herein has a lower level of MEK inhibition, e.g., of about 5-fold lower, about 10-fold lower, about 20-fold lower, about 30-fold lower, about 40-fold lower, about 50 fold lower, about 100-fold lower, about 200-fold lower, about 500 fold lower, about 1,000-fold lower level of MEK inhibition, as compared to the compound before it is metabolized/degraded.

In an embodiment, the half-life of the MEK inhibitor may have a half-life after exiting the skin, e.g., after systemic exposure, of less than about 24 hours, less than about 18 hours, less than about 14 hours, less than about 10 hours, less than about 9 hours, less than about 8 hours, less than about 7 hours, less than about 6 hours, less than about 5 hours, less than about 4 hours, less than about 3 hours, less than about 2 hours, less than about 1 hour, less than about 30 minutes, less than about 20 minutes, less than about 10 minutes, less than about 5 minutes, or less than about 1 minute.

In an embodiment, the half-life of the MEK inhibitor may have a half-life after introduction in vitro, e.g., after exposure to blood, serum or plasma in vitro, of less than about 24 hours, less than about 18 hours, less than about 14 hours, less than about 10 hours, less than about 9 hours, less than about 8 hours, less than about 7 hours, less than about 6 hours, less than about 5 hours, less than about 4 hours, less than about 3 hours, less than about 2 hours, less than about 1 hour, less than about 30 minutes, less than about 20 minutes, less than about 10 minutes, less than about 5 minutes, or less than about 1 minute.

In some embodiments, the half-life of the MEK inhibitor has a half-life of less than or equal to about 90 minutes, less than or equal to about 75 minutes, less than or equal to about 60 minutes, less than or equal to about 55 minutes, less than or equal to about 50 minutes, less than or equal to about 45 minutes, less than or equal to about 40 minutes, less than or equal to about 35 minutes, less than or equal to about 30 minutes, less than or equal to about 25 minutes, less than or equal to about 20 minutes, less than or equal to about 15 minutes, or less than or equal to about 10 minutes. In some embodiments, half-life of the MEK inhibitor is measured using Biological Example 3 using human liver S9 fraction.

Compounds

Provided herein are compounds that can modulate the activity of diseases or disorders associated with MEK. The compounds can be formed as described herein and used for the treatment of diseases or disorders in need of inhibition of MEK. In certain embodiments, the disease or disorder is Neurofibromatosis type 1. In certain embodiments, the disease or disorder is selected from the group consisting of a dermal rasopathy, a neurofibromatosis type 1, a dermal neurofibroma, a cutaneous neurofibroma, a subdermal neurofibroma, a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

The embodiments described herein include the recited compounds as well as a pharmaceutically acceptable salt, hydrate, solvate, stereoisomer, tautomer, or mixture thereof.

In some or any embodiments, provided is a Compound of Formula (I) according to Formula (Ia):

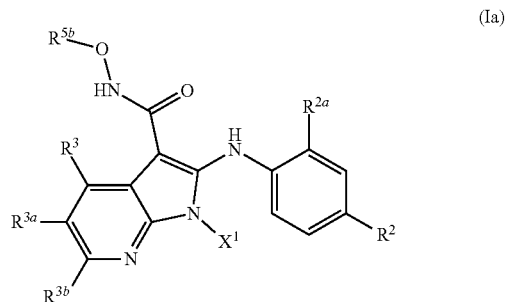

(Ia)

and all groups are as defined herein in any aspect or embodiment described herein.

In some or any embodiments, provided is a Compound of Formula (I) according to Formula (Ib):

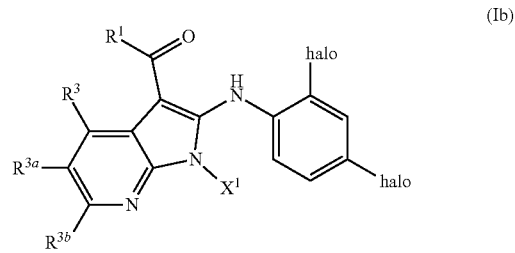

(Ib)

and all groups are as defined herein in any aspect or embodiment described herein.

In some or any embodiments, provided is a Compound of Formula (I) according to Formula (Ic):

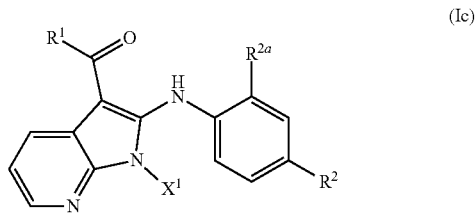

(Ic)

and all groups are as defined herein in any aspect or embodiment described herein.

In some or any embodiments, provided is a Compound of Formula (I), (Ia), (Ib), or (Ic) where $X^1$ is $C_1$-$C_3$ alkyl; and all other groups are as defined herein in any aspect or embodiment described herein. In some or any embodiments, provided is a Compound of Formula (I), (Ia), (Ib), or (Ic) where $X^1$ is $-CH_3$; and all other groups are as defined herein in any aspect or embodiment described herein. In some or any embodiments, provided is a Compound of Formula (I), (Ia), (Ib), or (Ic) where $X^1$ is $C_1$-$C_6$ alkyl) and at least one of $R^3$, $R^{3a}$, and $R^{3b}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; and all other groups are as defined herein in any aspect or embodiment described herein. In some or any embodiments, provided is a Compound of Formula (I), (Ia), (Ib), or (Ic) where $X^1$ is $C_1$-$C_6$ alkyl and at least one of $R^3$, $R^{3a}$, and $R^{3b}$ is $C_1$-$C_6$ alkyl or $C_1$-$C_6$ alkoxy; and all other groups are as defined herein in any aspect or embodiment described herein. In some or any embodiments, provided is a Compound of Formula (I), (Ia), (Ib), or (Ic) where $X^1$ is $C_1$-$C_6$ alkyl and at least one of $R^3$, $R^{3a}$, and $R^{3b}$ is methyl or methoxy; and all other groups are as defined herein in any aspect or embodiment described herein. In some or any embodiments, provided is a Compound of Formula (I), (Ia), (Ib), or (Ic) where $X^1$ is $C_1$-$C_6$ alkyl and at least one of $R^3$, $R^{3a}$, and $R^{3b}$ is $C_1$-$C_6$ alkyl; and all other groups are as defined herein in any aspect or embodiment described herein. In some or any embodiments, provided is a Compound of Formula (I), (Ia), (Ib), or (Ic) where $X^1$ is $C_1$-$C_6$ alkyl and at least one of $R^3$, $R^{3a}$, and $R^{3b}$ is methyl; and all other groups are as defined herein in any aspect or embodiment described herein. In some or any embodiments, provided is a Compound of Formula (I), (Ia), (Ib), or (Ic) where $X^1$ is $C_1$-$C_6$ alkyl and $R^3$, $R^{3a}$, and $R^{3b}$ are each hydrogen; and all other groups are as defined herein in any aspect or embodiment described herein.

In some or any embodiments, provided is a Compound of any one of Formulas (I), (Ia), and (Ic)-(Iu) where $R^2$ is —S—$C_1$-$C_3$ alkyl, $C_1$-$C_3$ alkyl, $C_2$-$C_4$ alkenyl, $C_2$-$C_3$ alkynyl, or halo; and all other groups are as defined herein in any aspect or embodiment described herein.

In some or any embodiments, provided is a Compound of any one of Formulas (I), (Ia), and (Ic)-(Iu) where $R^2$ is —S—$C_1$-$C_6$ alkyl; and all other groups are as defined herein in any aspect or embodiment described herein. In some or any embodiments, provided is a Compound of any one of Formulas (I), (Ia), and (Ic)-(Iu) where $R^2$ is —S—$C_1$-$C_3$ alkyl; and all other groups are as defined herein in any aspect or embodiment described herein. In some or any embodiments, provided is a Compound of any one of Formulas (I), (Ia), and (Ic)-(Iu) where $R^2$ is —S—$CH_3$; and all other groups are as defined herein in any aspect or embodiment described herein.

In some or any embodiments, provided is a Compound of any one of Formulas (I), (Ia), and (Ic)-(Iu) where $R^2$ is $C_1$-$C_6$ alkyl; and all other groups are as defined herein in any aspect or embodiment described herein. In some or any embodiments, provided is a Compound of any one of Formulas (I), (Ia), and (Ic)-(Iu) where $R^2$ is $C_1$-$C_3$ alkyl; and all other groups are as defined herein in any aspect or embodiment described herein. In some or any embodiments, provided is a Compound of any one of Formulas (I), (Ia), and (Ic)-(Iu) where $R^2$ is $CH_3$; and all other groups are as defined herein in any aspect or embodiment described herein.

In some or any embodiments, provided is a Compound of any one of Formulas (I), (Ia), and (Ic)-(Iu) where $R^2$ is $C_2$-$C_6$ alkenyl; and all other groups are as defined herein in any aspect or embodiment described herein. In some or any embodiments, provided is a Compound of any one of Formulas (I), (Ia), and (Ic)-(Iu) where $R^2$ is $C_2$-$C_4$ alkenyl; and all other groups are as defined herein in any aspect or embodiment described herein.

In some or any embodiments, provided is a Compound of any one of Formulas (I), (Ia), and (Ic)-(Iu) where $R^2$ is $C_2$-$C_6$ alkynyl; and all other groups are as defined herein in any aspect or embodiment described herein. In some or any embodiments, provided is a Compound of any one of Formulas (I), (Ia), and (Ic)-(Iu) where $R^2$ is $C_2$-$C_3$ alkynyl; and all other groups are as defined herein in any aspect or embodiment described herein. In some or any embodiments, provided is a Compound of any one of Formulas (I), (Ia), and (Ic)-(Iu) where $R^2$ is $C_2$ alkynyl; and all other groups are as defined herein in any aspect or embodiment described herein.

In some or any embodiments, provided is a Compound of any one of Formulas (I), (Ia), and (Ic)-(Iu) where $R^2$ is halo; and all other groups are as defined herein in any aspect or embodiment described herein. In some or any embodiments, provided is a Compound of any one of Formulas (I), (Ia), and (Ic)-(Iu) where $R^2$ is fluoro; and all other groups are as defined herein in any aspect or embodiment described herein. In some or any embodiments, provided is a Compound of any one of Formulas (I), (Ia), and (Ic)-(Iu) where $R^2$ is iodo; and all other groups are as defined herein in any aspect or embodiment described herein. In some or any embodiments, provided is a Compound of any one of Formulas (I), (Ia), and (Ic)-(Iu) where $R^2$ is chloro; and all other groups are as defined herein in any aspect or embodiment described herein. In some or any embodiments, provided is a Compound of any one of Formulas (I), (Ia), and (Ic)-(Iu) where $R^2$ is bromo; and all other groups are as defined herein in any aspect or embodiment described herein.

In some or any embodiments, provided is a Compound of any one of Formulas (I), (Ia), and (Ic)-(Iu) where $R^{2a}$ is halo or $C_1$-$C_3$ alkyl; and all other groups are as defined herein in any aspect or embodiment described herein. In some or any embodiments, provided is a Compound of any one of Formulas (I), (Ia), and (Ic)-(Iu) where $R^{2a}$ is halo or $CH_3$; and all other groups are as defined herein in any aspect or embodiment described herein. In some or any embodiments, provided is a Compound of any one of Formulas (I), (Ia), and (Ic)-(Iu) where $R^{2a}$ is fluoro or $CH_3$; and all other groups are as defined herein in any aspect or embodiment described herein. In some or any embodiments, provided is a Compound of any one of Formulas (I), (Ia), and (Ic)-(Iu) where $R^{2a}$ is iodo or $CH_3$; and all other groups are as defined herein in any aspect or embodiment described herein. In some or any embodiments, provided is a Compound of any one of Formulas (I), (Ia), and (Ic)-(Iu) where $R^{2a}$ is chloro or $CH_3$; and all other groups are as defined herein in any aspect or embodiment described herein. In some or any embodiments, provided is a Compound of any one of Formulas (I), (Ia), and (Ic)-(Iu) where $R^{2a}$ is bromo or $CH_3$; and all other groups are as defined herein in any aspect or embodiment described herein.

In some or any embodiments, provided is a Compound of any one of Formulas (I), (Ia), and (Ic)-(Iu) where $R^{2a}$ is halo; and all other groups are as defined herein in any aspect or embodiment described herein. In some or any embodiments, provided is a Compound of any one of Formulas (I), (Ia), and (Ic)-(Iu) where $R^{2a}$ is fluoro; and all other groups are as defined herein in any aspect or embodiment described herein. In some or any embodiments, provided is a Compound of any one of Formulas (I), (Ia), and (Ic)-(Iu) where $R^{2a}$ is iodo; and all other groups are as defined herein in any aspect or embodiment described herein. In some or any embodiments, provided is a Compound of any one of Formulas (I), (Ia), and (Ic)-(Iu) where $R^{2a}$ is chloro; and all other groups are as defined herein in any aspect or embodiment described herein. In some or any embodiments, provided is a Compound of any one of Formulas (I), (Ia), and (Ic)-(Iu) where $R^{2a}$ is bromo; and all other groups are as defined herein in any aspect or embodiment described herein.

In some or any embodiments, provided is a Compound of any one of Formulas (I), (Ia), and (Ic)-(Iu) where $R^{2a}$ is $C_1$-$C_6$ alkyl; and all other groups are as defined herein in any aspect or embodiment described herein. In some or any embodiments, provided is a Compound of any one of Formulas (I), (Ia), and (Ic)-(Iu) where $R^{2a}$ is $C_1$-$C_3$ alkyl; and all other groups are as defined herein in any aspect or embodiment described herein. In some or any embodiments, provided is a Compound of any one of Formulas (I), (Ia), and (Ic)-(Iu) where $R^{2a}$ is $CH_3$; and all other groups are as defined herein in any aspect or embodiment described herein.

In some or any embodiments, provided is a Compound of any one of Formulas (I), (Ia), and (Ic)-(Iu) where $R^{2a}$ is $C_1$-$C_6$ alkyl and $R^2$ is halo; and all other groups are as defined herein in any aspect or embodiment described herein. In some or any embodiments, provided is a Compound of any one of Formulas (I), (Ia), and (Ic)-(Iu) where $R^{2a}$ is halo and $R^2$ is halo; and all other groups are as defined herein in any aspect or embodiment described herein. In some or any embodiments, provided is a Compound of any one of Formulas (I), (Ia), and (Ic)-(Iu) where $R^{2a}$ is halo and $R^2$ is $C_2$-$C_6$ alkynyl; and all other groups are as defined herein in any aspect or embodiment described herein. In some or any embodiments, provided is a Compound of any one of Formulas (I), (Ia), and (Ic)-(Iu) where $R^{2a}$ is halo and $R^2$ is —S—$C_1$-$C_6$ alkyl; and all other groups are as defined herein in any aspect or embodiment described herein. In some or any embodiments, provided is a Compound of any one of Formulas (I), (Ia), and (Ic)-(Iu) where $R^{2a}$ is —$CH_3$ and $R^2$ is halo; and all other groups are as defined herein in any aspect or embodiment described herein. In some or any embodiments, provided is a Compound of any one of Formulas (I), (Ia), and (Ic)-(Iu) where $R^{2a}$ is halo and $R^2$ is $C_2$-$C_3$ alkynyl; and all other groups are as defined herein in any aspect or embodiment described herein. In some or any embodiments, provided is a Compound of any one of Formulas (I), (Ia), and (Ic)-(Iu) where $R^{2a}$ is halo and $R^2$ is —S—$C_1$-$C_3$ alkyl; and all other groups are as defined herein in any aspect or embodiment described herein. In some or any embodiments, provided is a Compound of any one of Formulas (I), (Ia), and (Ic)-(Iu) where $R^{2a}$ is halo and $R^2$ is —$SCH_3$; and all other groups are as defined herein in any aspect or embodiment described herein.

In some or any embodiments, provided is a Compound of any one of Formulas (I)-(Ib) where $R^3$, $R^{3a}$, and $R^{3b}$ are hydrogen; and all other groups are as defined herein in any aspect or embodiment described herein. In some or any embodiments, provided is a Compound of any one of Formulas (I)-(Ib) where at least one of $R^3$, $R^{3a}$, and $R^{3b}$ is $C_1$-$C_6$ alkyl or $C_1$-$C_6$ alkoxy; and all other groups are as defined herein in any aspect or embodiment described herein. In some or any embodiments, provided is a Compound of any one of Formulas (I)-(Ib) where at least one of $R^3$, $R^{3a}$, and $R^{3b}$ is methyl or methoxy; and all other groups are as defined herein in any aspect or embodiment described herein. In some or any embodiments, provided is a Compound of any one of Formulas (I)-(Ib) where at least one of $R^3$, $R^{3a}$, and $R^{3b}$ is $C_1$-$C_6$ alkyl; and all other groups are as defined herein in any aspect or embodiment described herein. In some or any embodiments, provided is a Compound of any one of Formulas (I)-(Ib) where at least one of $R^3$, $R^{3a}$, and $R^{3b}$ is methyl; and all other groups are as defined herein in any aspect or embodiment described herein.

In some or any embodiments, provided is a Compound of any one of Formulas (I)-(Ib) where one or two of $R^3$, $R^{3a}$, and $R^{3b}$ is hydrogen; and all other groups are as defined herein in any aspect or embodiment described herein. In some or any embodiments, provided is a Compound of any one of Formulas (I)-(Ib) where two of $R^3$, $R^{3a}$, and $R^{3b}$ are hydrogen; and all other groups are as defined herein in any aspect or embodiment described herein. In some or any embodiments, provided is a Compound of any one of Formulas (I)-(Ib) where one of $R^3$, $R^{3a}$, and $R^{3b}$ is $C_1$-$C_6$ alkyl or $C_1$-$C_6$ alkoxy and the others are hydrogen; and all other groups are as defined herein in any aspect or embodiment described herein. In some or any embodiments, provided is a Compound of any one of Formulas (I)-(Ib) where one of $R^3$, $R^{3a}$, and $R^{3b}$ is methyl or methoxy and the others are hydrogen; and all other groups are as defined herein in any aspect or embodiment described herein.

In some or any embodiments, provided is a Compound of any one of Formulas (I)-(Ib) where at least one of $R^3$, $R^{3a}$, and $R^{3b}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; and all other groups are as defined herein in any aspect or embodiment described herein. In some or any embodiments, provided is a Compound of any one of Formulas (I)-(Ib) where $R^3$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; $R^{3a}$ and $R^{3b}$ are hydrogen; and all other groups are as defined herein in any aspect or embodiment described herein. In some or any embodiments, provided is a Compound of any one of Formulas (I)-(Ib) where $R^{3a}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; $R^3$ and $R^{3b}$ are hydrogen; and all other groups are as defined herein in any aspect or embodiment described herein. In some or any embodiments, provided is a Compound of any one of Formulas (I)-(Ib) where $R^{3b}$ is $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy, $C_3$-$C_8$-cycloalkyloxy, heterocycloalkyloxy, heteroaryloxy, or phenoxy where each phenyl and heteroaryl is independently optionally substituted with 1, 2, or 3 $R^6$; $R^{3a}$ and $R^3$ are hydrogen; and all other groups are as defined herein in any aspect or embodiment described herein. In some or any embodiments, provided is a Compound of any one of Formulas (I)-(Ib) where $R^{3b}$ is $C_1$-$C_6$ alkyl or $C_1$-$C_6$-alkoxy; $R^{3a}$ and $R^3$ are hydrogen; and all other groups are as defined herein in any aspect or embodiment described herein. In some or any embodiments, provided is a Compound of any one of Formulas (I)-(Ib) where $R^{3b}$ is methyl or methoxy; $R^{3a}$ and $R^3$ are hydrogen; and all other groups are as defined herein in any aspect or embodiment described herein.

In some or any embodiments, provided is a Compound of any one of Formulas (I)-(Ib) where $R^3$, $R^{3a}$, and $R^{3b}$ are independently selected from hydrogen, halo, $C_1$-$C_6$ alkyl, $C_1$-$C_6$-alkoxy, $C_3$-$C_8$-cycloalkyloxy, heterocycloalkyloxy, heteroaryloxy where the heteroaryl is optionally substituted with 1, 2, or 3 $R^6$, and phenoxy where the phenyl is optionally substituted with 1, 2, or 3 $R^6$; and all other groups are as defined herein in any aspect or embodiment described herein. In some or any embodiments, provided is a Compound of any one of Formulas (I)-(Ib) where $R^3$, $R^{3a}$, and $R^{3b}$ are independently selected from hydrogen, halo, and $C_1$-$C_6$ alkyl; and all other groups are as defined herein in any aspect or embodiment described herein. In some or any embodiments, provided is a Compound of any one of Formulas (I)-(Ib) where $R^3$, $R^{3a}$, and $R^{3b}$ are independently selected from $C_1$-$C_6$-alkoxy, $C_3$-$C_8$-cycloalkyloxy, heterocycloalkyloxy, heteroaryloxy where the heteroaryl is optionally substituted with 1, 2, or 3 $R^6$, and phenoxy where the phenyl is optionally substituted with 1, 2, or 3 $R^6$; and all other groups are as defined herein in any aspect or embodiment described herein.

In some or any embodiments, provided is a Compound of any one of Formulas (Ia)-(Ic) where $R^1$ is —$OR^4$ or —$NR^5R^{5a}$; and all other groups are as defined herein in any aspect or embodiment described herein. In some or any embodiments, provided is a Compound of any one of Formulas (Ia)-(Ic) where $R^4$ and $R^5$ are unsubstituted $C_1$-$C_6$ alkyl; and all other groups are as defined herein in any aspect or embodiment described herein. In some or any embodiments, provided is a Compound of any one of Formulas (Ia)-(Ic) where $R^4$ and $R^5$ are $C_3$-$C_8$ cycloalkyl; and all other groups are as defined herein in any aspect or embodiment described herein. In some or any embodiments, provided is a Compound of any one of Formulas (Ia)-(Ic) where $R^4$ and $R^5$ are $C_3$-$C_8$ cycloalkyl-$C_1$-$C_6$-alkyl; and all other groups are as defined herein in any aspect or embodiment described herein. In some or any embodiments, provided is a Compound of any one of Formulas (Ia)-(Ic) where $R^4$ and $R^5$ are $C_1$-$C_6$ hydroxyalkyl; and all other groups are as defined herein in any aspect or embodiment described herein. In some or any embodiments, provided is a Compound of any one of Formulas (Ia)-(Ic) where $R^4$ and $R^5$ are $C_1$-$C_6$ alkoxyalkyl; and all other groups are as defined herein in any aspect or embodiment described herein.

In some or any embodiments, provided is a Compound of any one of Formulas (Ia)-(Ic) where $R^1$ is —$OR^4$; and all other groups are as defined herein in any aspect or embodiment described herein. In some or any embodiments, provided is a Compound of any one of Formulas (Ia)-(Ic) where $R^1$ is —$OR^4$ and $R^4$ is $C_1$-$C_6$ alkyl; and all other groups are as defined herein in any aspect or embodiment described herein. In some or any embodiments, provided is a Compound of any one of Formulas (Ia)-(Ic) where $R^1$ is —$OR^4$ and $R^4$ is $C_3$-$C_8$ cycloalkyl; and all other groups are as defined herein in any aspect or embodiment described herein. In some or any embodiments, provided is a Compound of any one of Formulas (Ia)-(Ic) where $R^1$ is —$OR^4$ and $R^4$ is $C_3$-$C_8$ cycloalkyl-$C_1$-$C_6$-alkyl; and all other groups are as defined herein in any aspect or embodiment described herein. In some or any embodiments, provided is a Compound of any one of Formulas (Ia)-(Ic) where $R^1$ is —$OR^4$ and $R^4$ is $C_1$-$C_6$ hydroxyalkyl; and all other groups are as defined herein in any aspect or embodiment described herein. In some or any embodiments, provided is a Compound of any one of Formulas (Ia)-(Ic) where $R^1$ is —$OR^4$ and $R^4$ is $C_1$-$C_6$ alkoxyalkyl; and all other groups are as defined herein in any aspect or embodiment described herein.

In some or any embodiments, provided is a Compound of any one of Formulas (Ia)-(Ic) where $R^1$ is —$NR^5R^{5a}$; and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is hydrogen; and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is unsubstituted $C_1$-$C_6$ alkyl; and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is $C_1$-$C_6$ alkyl substituted with one heterocycloalkyl (which is, in some embodiments, 2,2-dimethyl-1,3-dioxolan-4-yl); and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is $C_3$-$C_8$ cycloalkyl; and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is $C_3$-$C_8$ cycloalkyl-$C_1$-$C_6$-alkyl-; and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is $C_1$-$C_6$ hydroxyalkyl; and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is $C_1$-$C_6$ alkoxy-$C_1$-$C_6$-alkyl; and all other groups are as defined herein in any aspect or embodiment described herein. In some or any embodiments, provided is a Compound of any one of Formulas (Ia)-(Ic) where $R^1$ is —$NR^5R^{5a}$ and $R^5$ is —$OR^{5b}$; and all other groups are as defined herein in any aspect or embodiment described herein. In some or any embodiments, provided is a Compound of any one of Formulas (Ia)-(Ic) where $R^1$ is —$NR^5R^{5a}$, $R^5$ is —$OR^{5b}$, and $R^{5b}$ is hydrogen; and all other groups are as defined herein in any aspect or embodiment described herein. In some or any embodiments, provided is a Compound of any one of Formulas (Ia)-(Ic) where $R^1$ is —$NR^5R^{5a}$, $R^5$ is —$OR^5$b, and $R^{5b}$ is $C_1$-$C_6$ alkyl; and all other groups are as defined herein in any aspect or embodiment described herein. In some or any embodiments, provided is a Compound of any one of Formulas (Ia)-(Ic) where $R^1$ is —$NR^5R^{5a}$, $R^5$ is —$OR^{5b}$, and $R^{5b}$ is $C_3$-$C_8$ cycloalkyl; and all other groups are as defined herein in any aspect or embodiment described herein. In some or any embodiments, provided is a Compound of any one of Formulas (Ia)-(Ic) where $R^1$ is —$NR^5R^{5a}$, $R^5$ is —$OR^{5b}$, and $R^{5b}$ is $C_3$-$C_8$ cycloalkyl-$C_1$-$C_6$-alkyl; and all other groups are as defined herein in any aspect or embodiment described herein. In some or any embodiments, provided is a Compound of any one of Formulas (Ia)-(Ic) where $R^1$ is —$NR^5R^{5a}$, $R^5$ is —$OR^{5b}$, and $R^{5b}$ is $C_1$-$C_6$ hydroxyalkyl; and all other groups are as defined herein in any aspect or embodiment described herein. In some or any embodiments, provided is a Compound of any one of Formulas (Ia)-(Ic) where $R^1$ is —$NR^5R^{5a}$, $R^5$ is —$OR^{5b}$, and $R^{5b}$ is $C_1$-$C_6$ alkoxy-$C_1$-$C_6$-alkyl; and all other groups are as defined herein in any aspect or embodiment described herein. In particular, for any of the embodiments within this paragraph, provided is a Compound of any one of Formulas (Ia)-(Ic) where $R^{5a}$ is hydrogen; and all other groups (other than $R^5$, $R^{5a}$, and $R^{5b}$) are as defined herein in any aspect or embodiment described herein. In particular, for any of the embodiments within this paragraph, provided is a Compound of any one of Formulas (Ia)-(Ic) where $R^{5a}$ is $C_1$-$C_6$ alkyl; and all other groups (other than $R^5$, $R^{5a}$, and $R^{5b}$) are as defined herein in any aspect or embodiment described herein.

In some or any embodiments, provided is a Compound of any one of Formulas (Ia)-(Ic) where $R^{5a}$ is hydrogen; and all other groups are as defined herein in any aspect or embodiment described herein. In some or any embodiments, provided is a Compound of any one of Formulas (Ia)-(Ic) where $R^{5a}$ is $C_1$-$C_6$ alkyl; and all other groups are as defined herein in any aspect or embodiment described herein.

In some or any embodiments, provided is a Compound of any one of Formulas (Ia)-(Ic) where $R^1$ is an N-linked heterocycloalkyl where the N-linked heterocycloalkyl is optionally substituted with one or two $R^{10}$; and all other groups are as defined herein in any aspect or embodiment described herein. In some or any embodiments, provided is a Compound of any one of Formulas (Ia)-(Ic) where $R^1$ is N-linked azetidinyl, N-linked pyrrolidinyl, N-linked piperidinyl, or N-linked morpholinyl, where the N-linked heterocycloalkyl is optionally substituted with one or two $R^{10}$; and all other groups are as defined herein in any aspect or embodiment described herein. In some or any embodiments, provided is a Compound of any one of Formulas (Ia)-(Ic) where $R^1$ is N-linked azetidinyl, where the N-linked heterocycloalkyl is optionally substituted with one or two $R^{10}$; and all other groups are as defined herein in any aspect or embodiment described herein. In some or any embodiments, provided is a Compound of any one of Formulas (Ia)-(Ic) where $R^1$ is N-linked pyrrolidinyl, where the N-linked heterocycloalkyl is optionally substituted with one or two $R^{10}$; and all other groups are as defined herein in any aspect or embodiment described herein. In some or any embodiments, provided is a Compound of any one of Formulas (Ia)-(Ic) where $R^1$ is N-linked piperidinyl, where the N-linked heterocycloalkyl is optionally substituted with one or two $R^{10}$; and all other groups are as defined herein in any aspect or embodiment described herein. In some or any embodiments, provided is a Compound of any one of Formulas (Ia)-(Ic) where $R^1$ is N-linked morpholinyl, where the N-linked heterocycloalkyl is optionally substituted with one or two $R^{10}$; and all other groups are as defined herein in any aspect or embodiment described herein.

In some or any embodiments, provided is a Compound of any one of Formulas (I)-(Ib) where one $R^6$ is —$NR^{8a}S(O)_2R^8$; and all other groups are as defined herein in any aspect or embodiment described herein. In some or any embodiments, provided is a Compound of any one of Formulas (I)-(Ib) where one $R^6$ is —$NR^{5a}C(O)R^8$; and all other groups are as defined herein in any aspect or embodiment described herein. In some or any embodiments, provided is a Compound of any one of Formulas (I)-(Ib) where one $R^6$ is amino; and all other groups are as defined herein in any aspect or embodiment described herein. In some or any embodiments, provided is a Compound of any one of Formulas (I)-(Ib) where one $R^6$ is —$S(O)_2NR^{8a}R^8$; and all other groups are as defined herein in any aspect or embodiment described herein. In some or any embodiments, provided is a Compound of any one of Formulas (I)-(Ib) where one $R^6$ is —$C(O)NR^{5a}R^8$; and all other groups are as defined herein in any aspect or embodiment described herein. In some or any embodiments, provided is a Compound of any one of Formulas (I)-(Ib) where one $R^6$ is carboxy; and all other groups are as defined herein in any aspect or embodiment described herein. In some or any embodiments, provided is a Compound of any one of Formulas (I)-(Ib) where one $R^6$ is $C_1$-$C_6$-alkoxycarbonyl; and all other groups are as defined herein in any aspect or embodiment described herein.

In some or any embodiments, the Compound of Formula (I) is according to any one of the following formula:

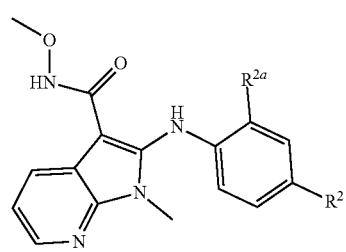

(Id)

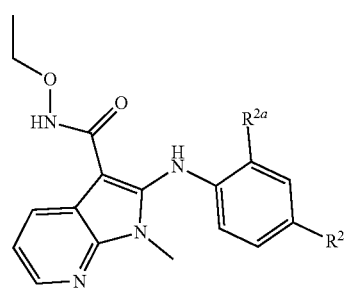

(Ie)

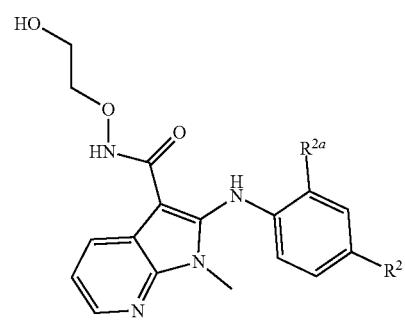

(If)

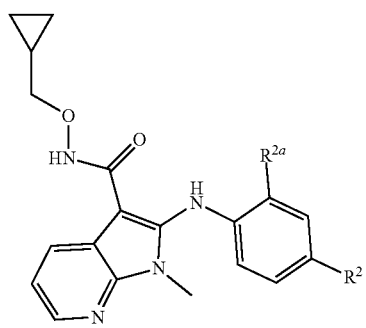

(Ig)

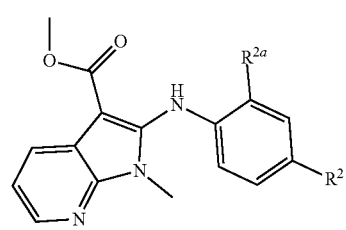

(Ih)

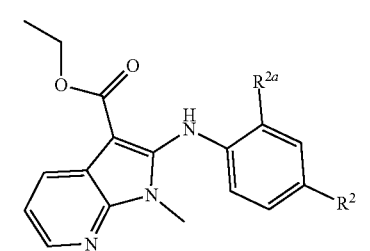
(Ii)
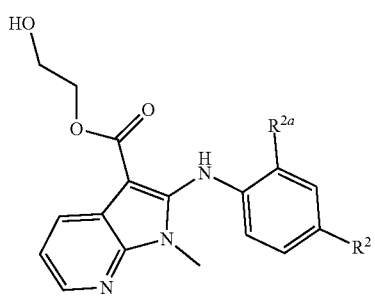
(Ij)
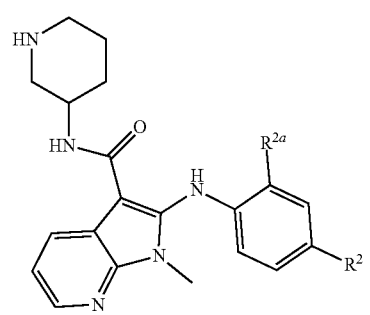
(Ik)
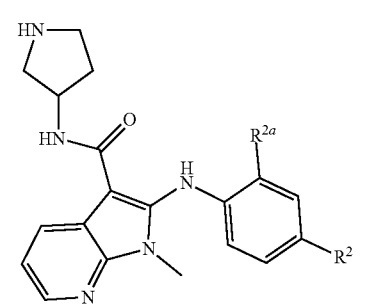
(Im)
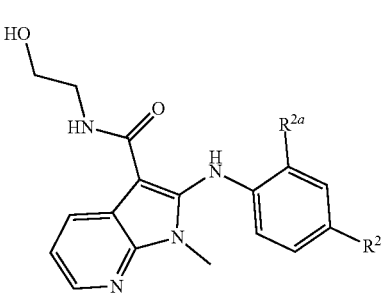
(In)
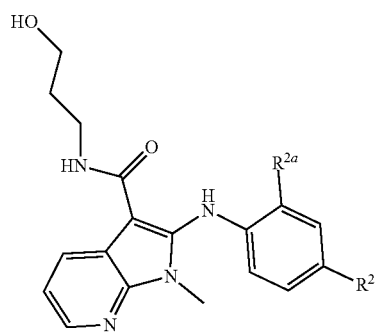
(Io)
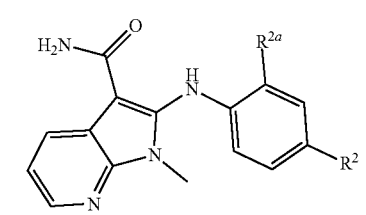
(Ip)
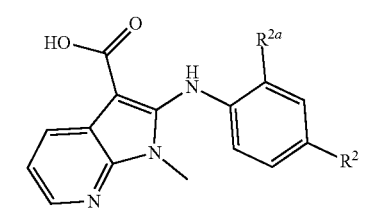
(Iq)
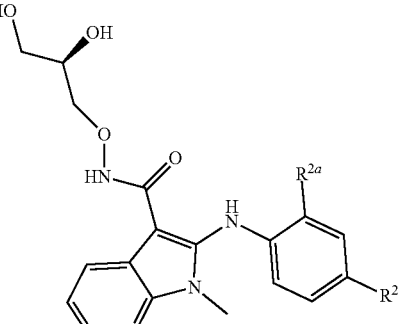
(Ir)
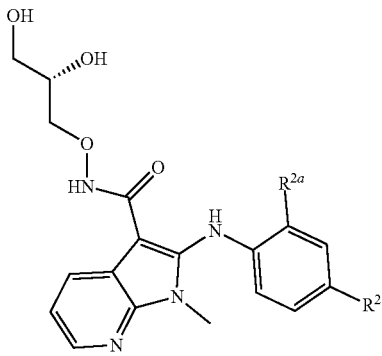
(Is)

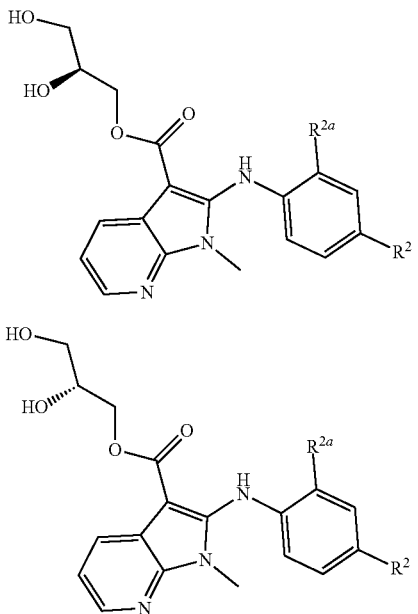

In some or any embodiments of the above structures, $R^{2a}$ is fluoro and $R^2$ is iodo, $R^{2a}$ is methyl and $R^2$ is iodo, $R^{2a}$ is fluoro and $R^2$ is ethynyl, $R^{2a}$ is methyl and $R^2$ is ethynyl, $R^{2a}$ is fluoro and $R^2$ is methylthio, or $R^{2a}$ is methyl and $R^2$ is methylthio; and all other groups are as defined herein in any aspect or embodiment described herein. In some or any embodiments of the above structures, $R^{2a}$ is fluoro and $R^2$ is iodo; and all other groups are as defined herein in any aspect or embodiment described herein. In some or any embodiments of the above structures, $R^{2a}$ is methyl and $R^2$ is iodo; and all other groups are as defined herein in any aspect or embodiment described herein. In some or any embodiments of the above structures, $R^{2a}$ is fluoro and $R^2$ is ethynyl; and all other groups are as defined herein in any aspect or embodiment described herein. In some or any embodiments of the above structures, $R^{2a}$ is methyl and $R^2$ is ethynyl; and all other groups are as defined herein in any aspect or embodiment described herein. In some or any embodiments of the above structures, $R^{2a}$ is fluoro and $R^2$ is methylthio; and all other groups are as defined herein in any aspect or embodiment described herein. In some or any embodiments of the above structures, $R^{2a}$ is methyl and $R^2$ is methylthio; and all other groups are as defined herein in any aspect or embodiment described herein.

In some embodiments, provided herein are:

(a) compounds as described herein, e.g., of any one of Formulas (I)-(Iu), the claims, and compounds in Embodiment A, and pharmaceutically acceptable salts and compositions thereof;

(b) compounds as described herein, e.g., of any one of Formulas (I)-(Iu), the claims, and compounds in Embodiment A, and pharmaceutically acceptable salts and compositions thereof for use in the treatment of MEK-inhibitor responsive disorder, MEK-inhibitor responsive dermal disorder, MEK-mediated disorder or disease, or disease or a MEK-mediated dermal disorder or disease where the subject is in need thereof;

(c) processes for the preparation of compounds as described herein, e.g., of any one of Formulas (I)-(Iu), the claims, and compounds in Embodiment A, as described in more detail elsewhere herein;

(d) pharmaceutical formulations comprising a compound as described herein, e.g., of any one of Formulas (I)-(Iu), the claims, and compounds in Embodiment A, or a pharmaceutically acceptable salt thereof together with a pharmaceutically acceptable carrier or diluent;

(e) a method for the treatment of a condition, where the subject is in need thereof, that includes the administration of a therapeutically or prophylactically effective amount of a compound as described herein, e.g., of any one of Formulas (I)-(Iu), the claims, and compounds in Embodiment A, its pharmaceutically acceptable salt or composition;

(f) a method for the treatment of MEK-inhibitor responsive disorder, MEK-inhibitor responsive dermal disorder or disease, MEK-mediated disorder or disease, or a MEK-mediated dermal disorder or disease in a subject that includes the administration of a therapeutically or prophylactically effective amount of a compound as described herein, e.g., of any one of Formulas (I)-(Iu), the claims, and compounds in Embodiment A, its pharmaceutically acceptable salt or composition;

(g) pharmaceutical formulations comprising a compound as described herein, e.g., of any one of Formulas (I)-(Iu), the claims, and compounds in Embodiment A, or a pharmaceutically acceptable salt thereof together with one or more other effective agents for treating MEK-inhibitor responsive disorder, MEK-inhibitor responsive dermal disorder or disease, MEK-mediated disorder or disease, or a MEK-mediated dermal disorder or disease where the subject is in need thereof, optionally in a pharmaceutically acceptable carrier or diluent;

(h) a method for the treatment of a MEK-inhibitor responsive disorder, MEK-inhibitor responsive dermal disorder or disease, MEK-mediated disorder or disease, or MEK-mediated dermal disorder or disease in a subject that includes the administration of a therapeutically or prophylactically effective amount of a compound as described herein, e.g., of any one of Formulas (I)-(Iu), the claims, and compounds in Embodiment A, its pharmaceutically acceptable salt or composition in combination and/or alternation with one or more agent for the treatment of a MEK-inhibitor responsive disorder, MEK-inhibitor responsive dermal disorder or disease, MEK-mediated disorder or disease, or a MEK-mediated dermal disorder or disease where the subject is in need thereof, and (i) a method for the treatment of a condition, where the subject is in need thereof, that includes the administration of a therapeutically or prophylactically effective amount of a compound as described herein, e.g., of any one of Formulas (I)-(Iu), the claims, and compounds in Embodiment A, or its pharmaceutically acceptable salt or composition in combination and/or alternation with one or more agent for the treatment of a MEK-inhibitor responsive disorder, MEK-inhibitor responsive dermal disorder or disease, MEK-mediated disorder or disease, or a MEK-mediated dermal disorder or disease.

Optically Active Compounds

It is appreciated that compounds provided herein have several chiral centers and may exist in and be isolated in optically active and racemic forms. It is to be understood that any racemic, optically-active, diastereomeric, tautomeric, or stereoisomeric form, or mixtures thereof, of a compound provided herein, which possess the useful properties described herein is within the scope of the invention. It being well known in the art how to prepare optically active forms (in certain embodiments, by resolution of the racemic form by recrystallization techniques, by synthesis from optically-active starting materials, by chiral synthesis, or by chromatographic separation using a chiral stationary phase). In addition, the compounds described herein may epimerize at the C11 position under certain conditions. Such epimers are within the embodiments provided herein.

In certain embodiments, methods to obtain optically active materials are known in the art, and include at least the following.

i) physical separation of crystals—a technique whereby macroscopic crystals of the individual stereoisomers are manually separated. This technique can be used if crystals of the separate stereoisomers exist, i.e., the material is a conglomerate, and the crystals are visually distinct;

ii) simultaneous crystallization—a technique whereby the individual stereoisomers are separately crystallized from a solution of the racemate, possible only if the latter is a conglomerate in the solid state;

iii) enzymatic resolutions—a technique whereby partial or complete separation of a racemate by virtue of differing rates of reaction for the stereoisomers with an enzyme;

iv) enzymatic asymmetric synthesis—a synthetic technique whereby at least one step of the synthesis uses an enzymatic reaction to obtain an stereoisomerically pure or enriched synthetic precursor of the desired stereoisomer;

v) chemical asymmetric synthesis—a synthetic technique whereby the desired stereoisomer is synthesized from an achiral precursor under diseases or disorders that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the stereoisomers with a chiral, non-racemic reagent or catalyst under kinetic conditions;

ix) stereospecific synthesis from non-racemic precursors—a synthetic technique whereby the desired stereoisomer is obtained from non-chiral starting materials and where the stereochemical integrity is not or is only minimally compromised over the course of the synthesis;

x) chiral liquid chromatography—a technique whereby the stereoisomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and stereoisomers are separated by virtue of their differing interactions in the gaseous mobile phase with a column containing a fixed non-racemic chiral adsorbent phase;

xii) extraction with chiral solvents—a technique whereby the stereoisomers are separated by virtue of preferential dissolution of one stereoisomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one stereoisomer of the racemate to pass through.

In some embodiments, provided is a composition of a compound that comprises a substantially pure designated stereoisomer of the compound. In certain embodiments, in the methods and compounds, the compounds are substantially free of other stereoisomers. In some embodiments, provided is a composition of a compound that comprises a substantially pure designated enantiomer of the compound. In certain embodiments, in the methods and compounds, the compounds are substantially free of other enantiomers. In some embodiments, provided is a composition of a compound that comprises a substantially pure designated diastereomer of the compound. In certain embodiments, in the methods and compounds, the compounds are substantially free of other diastereomers. In some embodiments, provided is a composition of a compound that comprises a substantially pure geometric isomer of the compound. In certain embodiments, in the methods and compounds, the compounds are substantially free of other geometric isomers. In some embodiments, a composition includes a compound that is at least 85%, 90%, 95%, 98%, 99% or 100% by weight, of the compound, the remainder comprising other chemical species or stereoisomers.

Isotopically Enriched Compounds

Also provided herein are isotopically enriched compounds. Isotopic enrichment (in certain embodiments, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, in certain embodiments, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al., Adv. Drug Res., vol. 14, pp. 1-36 (1985); Kushner et al., Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. In certain embodiments, such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Pharmaceutical Compositions and Methods of Administration

The compounds provided herein can be formulated into pharmaceutical compositions using methods available in the art and those disclosed herein. Any of the compounds disclosed herein can be provided in the appropriate pharmaceutical composition and be administered by a suitable route of administration.

In some or any embodiments, administration of the compound described herein to a subject may be local or non-systemic, e.g., topical, subcutaneous, transdermal, intradermal, or intralesional. In an embodiment, the compound can be administered by topical administration. In an embodiment, the compound can be administered by intradermal administration. In an embodiment, the compound can be administered by intralesional administration, e.g., by intralesional injection.

The methods provided herein encompass administering pharmaceutical compositions containing at least one compound as described herein, including a compound of Formula (I)-(Ic) and the claims, and compounds in Embodiment A, if appropriate in a salt form, either used alone or in the form of a combination with one or more compatible and pharmaceutically acceptable carriers, such as diluents or adjuvants, or with another agent for the treatment of MEK-inhibitor responsive disorder or disease, MEK-inhibitor responsive dermal disorder or disease, MEK-mediated disorder or disease, or a MEK-mediated dermal disorder or disease where the subject is in need thereof.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular topically, subcutaneously, transdermally, intradermally, intralesionally orally, parenterally, rectally or by inhalation (e.g. in the form of aerosols). In certain embodiments, the compound provided herein is administered topically, subcutaneously, transdermally, intradermally, or intralesionally. In certain embodiments, the compound provided herein is administered topically. In certain embodiments, the compound provided herein is administered intradermally. In certain embodiments, the compound provided herein is administered intralesionally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in certain embodiments, wetting, sweetening or flavoring products.

Use may be made, of compositions for topical administration as lotions, tinctures, creams, emulsions, gels or ointments. In these compositions, the active product is mixed with one or more inert excipients including water, acetone, ethanol, ethylene glycol, propylene glycol, butane 1,3 diol, isopropyl myristate, isopropyl palmitate, mineral oil, and mixtures thereof.

The compositions for parenteral, intralesional, or intradermal administration can be emulsions or sterile solutions. Use may be made, as solvent or vehicle, of propylene glycol, a polyethylene glycol, vegetable oils, in particular olive oil, or injectable organic esters, in certain embodiments, ethyl oleate. These compositions can also contain adjuvants, in particular wetting, isotonizing, emulsifying, dispersing and stabilizing agents. Sterilization can be carried out in several ways, in certain embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in certain embodiments, dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in certain embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in certain embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In certain embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, in certain embodiments, an animal subject, such as a mammalian subject, in certain embodiments, a human subject.

A pharmaceutical composition is formulated to be compatible with its intended route of administration. In certain embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In certain embodiments, the route of administration is intradermal, transdermal, topical, subcutaneous, or intralesional administration. In certain embodiments, the route of administration is non-systemic administration. In a specific embodiment, the composition is formulated in accordance with routine procedures as a pharmaceutical composition adapted for intravenous, subcutaneous, intramuscular, oral, intranasal, transdermal, intradermal, intralesional, or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

In certain embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g, aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In certain embodiments, a dosage form used in the initial treatment of a MEK-inhibitor responsive disorder or disease, MEK-inhibitor responsive dermal disorder or disease, MEK-mediated disorder or disease, or a MEK-mediated dermal disorder or disease may contain larger amounts of one or more of the active ingredients it comprises than a dosage form used in the maintenance treatment of the same disorder or disease. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in certain embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In certain embodiments, the oral dosage forms are solid and prepared under anhydrous diseases or disorders with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In certain embodiments, excipients suitable for use in oral liquid or aerosol dosage forms include, but are not limited to, water, glycols, oils, alcohols, flavoring agents, preservatives, and coloring agents. In certain embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In certain embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In certain embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In certain embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, PA), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in certain embodiments, a syloid silica gel (AEROSIL 200, manufactured by W.R. Grace Co. of Baltimore, MD), a coagulated aerosol of synthetic silica (marketed by Degussa Co. of Plano, TX), CAB O SIL (a pyrogenic silicon dioxide product sold by Cabot Co. of Boston, MA), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In certain embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in certain embodiments, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the disease or disorder in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of one or more side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various diseases or disorders including, but not limited to, pH, temperature, enzymes, water, or other physiological diseases or disorders or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. In certain embodiments, parenteral dosage forms can be administered to subjects by various routes including, but not limited to, subcutaneous, intravenous (including bolus injection), intramuscular, and intra-arterial. In certain embodiments, parenteral dosage forms can be administered to subjects by various routes including, but not limited to, topical, subcutaneous, transdermal, intradermal, or intralesional. Because their administration typically bypasses subjects' natural defenses against contaminants, parenteral dosage forms are typically, sterile or capable of being sterilized prior to administration to a subject. In certain embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In certain embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Suitable carriers (e.g., excipients and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical carriers include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. In some embodiments, materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In certain embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, a doctor will determine the posology which he considers most appropriate according to a preventive or curative treatment and according to the age, weight, stage of the disorder or disease and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating a disease or disorder where the subject is in need thereof and/or MEK-inhibitor responsive disorder or disease, MEK-inhibitor responsive dermal disorder or disease, MEK-mediated disorder or disease, or a MEK-mediated dermal disorder or disease in a subject by administering, to a subject in need thereof, a therapeutically or prophylactically effective amount of a compound provided herein, or a pharmaceutically acceptable salt thereof. The amount of the compound or composition which will be therapeutically or prophylactically effective in the treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, between 0.30 mg/kg and 1.50 mg/kg, between 1 mg/kg and 100 mg/kg, between 5 mg/kg and 50 mg/kg, between 10 mg/kg and 50 mg/kg, between 20 mg/kg and 50 mg/kg, between 15 mg/kg and 40 mg/kg, between 15 mg/kg and 35 mg/kg, between 15 mg/kg and 30 mg/kg, between 25 mg/kg and 35 mg/kg, between 10 mg/kg and 30 mg/kg, between 10 mg/kg and 20 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg of the subject's body weight.

In certain embodiments, the recommended daily dose range of a composition provided herein for the diseases or disorders described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In certain embodiments, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosage may vary within a range depending upon the dosage form employed and the route of administration utilized. For any compound, the therapeutically effective dose can be estimated initially from cell culture assays. A dose may be formulated in animal models to achieve a level in the skin with the lesion, e.g., the dermal neurofibroma, the cutaneous neurofibroma, the subdermal neurofibroma, or the superficial plexiform neurofibroma) that includes the $IC_{50}$ (i.e., the concentration of the test compound that achieves a half-maximal inhibition of symptoms) as determined in cell culture. Such information can be used to more accurately determine useful doses in humans. In addition, levels in plasma may be measured, for example, by high performance liquid chromatography, in order to ascertain systemic exposure.

It should also be understood that a specific dosage and treatment regimen for any particular patient will depend upon a variety of factors, including the activity of the specific compound employed, the age, the size of the lesion, number of lesions, general health, sex, diet, time of administration, drug combination, and the judgment of the treating physician and the severity of the particular disease being treated. The amount of a soft MEK inhibitor, e.g., a soft MEK inhibitor described herein, in the composition will also depend upon the particular soft MEK inhibitor in the composition.

In some embodiments, the topical, subcutaneous, transdermal, intradermal, or intralesional dose is about 0.01 $\mu g/cm^2$, about 0.05 $\mu g/cm^2$, about 0.1 $\mu g/cm^2$, about 0.15 $\mu g/cm^2$, about 0.2 $\mu g/cm^2$, about 0.3 $\mu g/cm^2$, about 0.4 $\mu g/cm^2$, about 0.5 $\mu g/cm^2$, about 0.6 $\mu g/cm^2$, about 0.7 $\mu g/cm^2$, about 0.8 $\mu g/cm^2$, or about 0.9 $\mu g/cm^2$; or is within about 0.01-0.03 $\mu g/cm^2$, about 0.03-0.05 $\mu g/cm^2$, about 0.05-0.1 $\mu g/cm^2$, about 0.1-0.3 $\mu g/cm^2$, about 0.3-0.5 $\mu g/cm^2$, about 0.5-0.8 $\mu g/cm^2$, about 0.8-1.0 $\mu g/cm^2$, about 1-10 $\mu g/cm^2$, about 10-20 $\mu g/cm^2$, about 20-30 $\mu g/cm^2$, about 30-40 $\mu g/cm^2$, about 40-50 $\mu g/cm^2$, about 50-60 $\mu g/cm^2$, about 60-70 $\mu g/cm^2$, about 70-80 $\mu g/cm^2$, about 80-90 $\mu g/cm^2$, about 90-100 $\mu g/cm^2$, about 100-125 $\mu g/cm^2$, about 125-150 $\mu g/cm^2$, about 150-175 $\mu g/cm^2$, about 175-200 $\mu g/cm^2$, about 200-250 $\mu g/cm^2$, about 250-300 $\mu g/cm^2$, about 300-350 $\mu g/cm^2$, about 350-400 $\mu g/cm^2$, about 400-450 $\mu g/cm^2$, about 450-500 $\mu g/cm^2$, about 500-550 $\mu g/cm^2$, about 550-600 $\mu g/cm^2$, about 600-650 $\mu g/cm^2$, about 650-700 $\mu g/cm^2$, about 700-750 $\mu g/cm^2$, about 750-800 $\mu g/cm^2$, about 800-850 $\mu g/cm^2$, about 850-900 $\mu g/cm^2$, about 900-950 $\mu g/cm^2$, or about 950-1000 $\mu g/cm^2$.

In some embodiments, the topical, subcutaneous, transdermal, intradermal, or intralesional dose is within about 0.5-1.0 $mg/cm^2$, 1.0-1.5 $mg/cm^2$, 1.5-2.0 $mg/cm^2$, 2.5-2.5 $mg/cm^2$, 3.0-3.5 $mg/cm^2$, 3.5-5.0 $mg/cm^2$, 5.0-7.5 $mg/cm^2$, 7.5-10 $mg/cm^2$, 1-10 $mg/cm^2$, about 10-20 $mg/cm^2$, about 20-30 $mg/cm^2$, about 30-40 $mg/cm^2$, about 40-50 $mg/cm^2$, about 50-60 $mg/cm^2$, about 60-70 $mg/cm^2$, about 70-80 $mg/cm^2$, about 80-90 $mg/cm^2$, about 90-100 $mg/cm^2$, about 100-125 $mg/cm^2$, about 125-150 $mg/cm^2$, about 150-175 $mg/cm^2$, about 175-200 $mg/cm^2$, about 200-250 $mg/cm^2$, about 250-300 $mg/cm^2$, about 300-350 $mg/cm^2$, about 350-400 $mg/cm^2$, about 400-450 $mg/cm^2$, about 450-500 $mg/cm^2$, about 500-550 $mg/cm^2$, about 550-600 $mg/cm^2$, about 600-650 $mg/cm^2$, about 650-700 $mg/cm^2$, about 700-750 $mg/cm^2$, about 750-800 $mg/cm^2$, about 800-850 $mg/cm^2$, about 850-900 $mg/cm^2$, about 900-950 $mg/cm^2$, or about 950-1000 $mg/cm^2$.

In certain embodiments, dosages of the second agents to be used in a combination therapy are provided herein. In certain embodiments, dosages lower than those which have been or are currently being used to treat MEK-inhibitor responsive disorder or disease, MEK-inhibitor responsive dermal disorder or disease, MEK-mediated disorder or disease, or a MEK-mediated dermal disorder or disease are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics 9$^{th}$ Ed, McGraw-Hill, New York; Physician's Desk Reference (PDR) 57$^{th}$ Ed., 2003, Medical Economics Co., Inc., Montvale, NJ; which are incorporated herein by reference in their entirety.

The disclosure provides combination treatments by administration of a MEK inhibitor, e.g. a soft MEK inhibitor, described herein with one or more additional agent(s). In an embodiment, the one or more additional agent(s) is selected from:

- agents that treat acne (e.g., Accutane, Azelaic acid, Benzoyl Peroxide, Salicylic acid);
- analgesics (e.g., Acetaminophen, Capsaicin), e.g., a Cox2 Inhibitor, e.g. Celecoxib);
- anesthetics (e.g., Benzocaine, Benzocaine/Menthol, Dibucaine, Diperodon, Lidocaine, Lidocaine/Prilocaine, Pramoxine);
- anti-infectives (e.g., Crotamiton);
- anti-pruritus (e.g., Ammonium lactate, Benzocaine, an ascomycin macrolactam, e.g., Pimecrolimus);
- anti-pruritus/5HT3 receptor antagonists (e.g., Ondansetron);
- antibiotics (e.g., clindamycin, doxycycline, erythromycin, tetracycline);
- anticholinergic antiemetics (e.g., diphenhydramine);
- antifibrotics (e.g., Collagenase, Pirfenidone);
- antihistamines (e.g., Triprolidine (Actifed®), Fexofenadine (Allergra®, Allegra® D-12, Allegra®-24), Astepro/Astelin Nasal Spray (Azalastine) (Dymista®), Hydroxyzine hydrochloride (Atarax®), Diphenhydramine Hydrochloride (Benadryl®), Brompheniramine (Dimetapp® Cold and Allergy Elixir), Zyrtec® (Cetirizine), Chlor-Trimeton® (Chlorpheniramine), Descoratadine (Clarinex®, Clarinex® D-12, and Clarinex® D-24), Loratadine (Claritin®, Claritin® D-12, Claritin® D-24, and Alavert®), Dimenhydrinate (Dramamine®), Diphenhydramine (Benadryl® Allergy, Nytol®, Sominex®), Doxylamine (Vicks® NyQuil®, Alka-Seltzer® Plus Night-Time Cold Medicine), Cyproheptadine (Periactin®), Promethazine (Phenergan®), Acrivastine (Semprex®, Semprex®-D), Clemastine (Tavist®), doxylamine (Unisom®), Levocetirizine (Xyzal®);
- mast cell stabilizers (e.g. Beta2-adrenergic agonists, Cromoglicic acid, cromolyn sodium, Gastrocrom®, Ketotifen, Methylxanthines, Omalizumab, Pemirolast, Quercetin, Ketotifen (Zaditen®));
- anti-inflammatory agents (e.g., NSAID (e.g. Aspirin, Choline and magnesium salicylates, Diclofenac potassium (Cataflam®), Diclofenac sodium (Voltaren®, Voltaren® XR), Diclofenac sodium with misoprostol (Arthrotec®), Diflunisal (Dolobid®), Etodolac (Lodine®, Lodine® XL), Fenoprofen calcium (Nalfon®), Flurbiprofen (Ansaid®), Ibuprofen (Advil®, Motrin®, Motrin® IB, Nuprin®), Indomethacin (Indocin®, Indocin® SR), Ketoprofen (Actron®, Orudis®, Orudis® KT, Oruvail®), Magnesium salicylate (Arthritab, Bayer® Select, Doan's Pills, Magan, Mobidin, Mobogesic) Meclofenamate sodium (Meclomen®), Mefenamic acid (Ponstel®), Meloxicam (Mobic®), Nabumetone (Relafen®), Naproxen (Naprosyn®, Naprelan®), Naproxen sodium (Aleve®, Anaprox®), Oxaprozin (Daypro®), Piroxicam (Feldene®), Rofecoxib (Vioxx®), Salsalate (Amigesic, Anaflex 750, Disalcid, Marthritic, Mono-Gesic, Salflex, Salsitab), Sodium salicylate, Sulindac (Clinoril®), Tolmetin sodium (Tolectin®), Valdecoxib (Bextra®));
- Receptor Tyrosine Kinase Inhibitor (e.g. Sunitinib);
- Alkylating Agents (e.g., Dacarbazine, Carboplatin);
- CDK 4/6 Inhibitors (e.g., LEE011);
- PKC Inhibitors (e.g., AEB071);
- MAPK inhibitors (e.g., RAS Inhibitors/Farnesyltransferase inhibitor (e.g. Tipifamib), Raf Kinase Inhibitor (e.g. Sorafenib (BAY 43-9006, Nexavar), Vemurafenib, Dabrafenib, LGX818, TAK-632, MLN2480, PLX-4720), ERK Inhibitors (e.g., SCH772984, VTX11e);
- PI3K Inhibitor (e.g., LY294002);
- AKT Inhibitor (e.g., MK 2206);
- PI3K/AKT Inhibitor (e.g. buparlisib, Cixutumumab);
- mTOR Inhibitors (e.g. Topical Rapamycin, RAD001 (Everolimus/Rapamycin), Temsirolimus, Sirolimus);
- Tyrosine Kinase Inhibitors (e.g. Imatinib (Gleevec®), Cabozantinib (inhibitor of tyrosine kinases c-Met and VEGFR2), Nilotinib (Tasigna®);
- VEGF Inhibitor (e.g. Ranibizumab (Lucentis®), Cediranib);
- Immune Response Modifier (e.g. Topical Imiquimod, Interferon, PEG Interferon);
- Calcium Channel Blocker (e.g. Avocil (Mederma)/15% Verapamil, vitamin D separately, Doxycyline Injections);
- Statin (e.g. Lovastatin, Methotrexate, Vinblastine, Pregabalin, Temozolomide, PLX3397);
- HDAC Inhibitor (e.g. AR-42);
- HSP-90 Inhibitors (e.g. Ganetespib);
- retinoids (e.g. adapalene, Isotretinoin, tazarotene, tretinoin);
- steroids (e.g. Alclometasone, Amcinonide, Betamethasone, Betamethasone dipropionate, Betamethasone dipropionate, augmented, Budesonide, Clobetasol propionate, Cortisone, Desonide, Dexamethasone, Diflorasone diacetate, Fluocinolone acetonide, Fluocinonide, Flurandrenolide, Fluticasone propionate, Halobetasol propionate, Halocinonide, Hydrocortisone, Hydrocortisone butyrate, Hydrocortisone valerate, Methylprednisolone, Mometasone, Mometasone furoate, Prednicarbate, Prednisolone, Prednisone, Triamcinolone, Triamcinolone acetonide);
- topical calcineurin inhibitors (e.g., pimecrolimus (Elidel® Cream 1%, Novartis, tacrolimus (Protopic® Ointment, Astellas)); and
- Non-pharmaceutical Interventions (e.g. photodynamic Therapy (Levulan Kerastick Topical+light), Electrodesication (ED), YAG Laser).

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, in certain embodiments, a mammal, such as a human, in a sequence and within a time interval such that the compound provided herein can act together with the other agent to provide an increased benefit than if they were administered otherwise. In certain embodiments, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce one or more of the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. In certain embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a MEK-inhibitor responsive disorder or disease, MEK-inhibitor responsive dermal disorder or disease, MEK-mediated dermal disorder or disease, or a MEK-mediated dermal disorder or disease where the subject is in need thereof or a MEK-inhibitor responsive disorder or disease, MEK-inhibitor responsive dermal disorder or disease, MEK-mediated disorder or disease, or a MEK-mediated dermal disorder or disease. The kits can include a compound or composition provided herein, a second agent or composition, and instructions providing information to a health care provider regarding usage for treating a MEK-inhibitor responsive disorder or disease, MEK-inhibitor responsive dermal disorder or disease, MEK-mediated disorder or disease, or a MEK-mediated dermal disorder or disease. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 day. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for treating a disease or disorder where the subject is in need thereof and/or MEK-inhibitor responsive disorder or disease, MEK-inhibitor responsive dermal disorder or disease, MEK-mediated disorder or disease, or a MEK-mediated dermal disorder or disease in a subject, which comprises contacting the subject with a therapeutically or prophylactically effective amount of a compound disclosed herein, e.g., a compound of any one of Formulas (I)-(Iu) and the claims, and compounds in Embodiment A, including a single enantiomer, a mixture of an enantiomeric pair, an individual diastereomer, a mixture of diastereomers, an individual stereoisomer, a mixture of stereoisomers, or a tautomeric form thereof; or a pharmaceutically acceptable salt, solvate, prodrug, phosphate, or active metabolite thereof.

In certain embodiments, provided herein are methods for treating a MEK-inhibitor responsive disorder or disease, MEK-inhibitor responsive dermal disorder or disease, MEK-mediated disorder or disease, or a MEK-mediated dermal disorder or disease where the subject is in need thereof. In certain embodiments, the methods encompass the step of administering to the subject in need thereof an amount of a compound effective for the treatment of a MEK-inhibitor responsive disorder or disease, MEK-inhibitor responsive dermal disorder or disease, MEK-mediated disorder or disease, or a MEK-mediated dermal disorder or disease where the subject is in need thereof in combination with a second agent effective for the treatment or prevention of a MEK-inhibitor responsive disorder or disease, MEK-inhibitor responsive dermal disorder or disease, MEK-mediated disorder or disease, or a MEK-mediated dermal disorder or disease where the subject is in need thereof. The compound can be any compound as described herein, and the second agent can be any second agent described in the art or herein. In certain embodiments, the compound is in the form of a pharmaceutical composition or dosage form, as described elsewhere herein.

In certain embodiments, provided herein are methods for treating a disease or disorder where the subject is in need thereof. In certain embodiments, the methods encompass the step of administering to the subject in need thereof a therapeutically or prophylactically effective amount of a compound effective for the treatment of a disease or disorder where the subject is in need thereof in combination with a second agent effective for the treatment of a disease or disorder where the subject is in need thereof. The compound can be any compound as described herein, and the second agent can be any second agent described in the art or herein. In certain embodiments, the compound is in the form of a pharmaceutical composition or dosage form, as described elsewhere herein.

Neurofibromatosis type 1 (NF1): In an embodiment, the dermal disorder is associated with NF1. NF1, also known as von Recklinghausen Neurofibromatosis or Peripheral Neurofibromatosis, occurs in approximately 1:3,000 births, and is one of the most prevalent genetic disorders and the most common neurocutaneous disorders. NF1 is caused by a deficiency in neurofibromin, which leads to hyperactivation of various cell-signaling pathways, e.g., Ras and Rho, is associated with several dermal disorders, including dermal neurofibromas (DFs); cutaneous neurofibromas; subdermal neurofibromas; superficial plexiform neurofibromas (PFs); cutaneous neurofibromas (CFs); café au lait spots; and axillary and inguinal freckling. DFs occur in over 95% of NF1 patients. DFs can appear anywhere on the body, with 88% of NF1 patients over 40 years of age having over 100 DFs. DFs can cause both severe physical pain, disfigurement, as well as social anxiety. Facial DFs can create significant social anxiety issues and pain among affected individuals. DFs (also known as cutaneous neurofibromas or discrete neurofibromas) grow from small nerves in the skin or just under the skin and appear as small bumps typically beginning around the time of puberty. Current treatment options for DF are limited to surgical excisin and $CO_2$ laser removal, both of which cause scarring and neither of which is preventative.

Other Dermal Rasopathies: In an embodiment, the dermal disorder is associated with enhanced activation of Ras. In an embodiment, the dermal disorder is selected from: psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots and Multiple lentigines syndrome (formerly called Leopard syndrome).

In some or any embodiments, the disease to be reduced, ameliorated, treated, or prevented is not cancer (e.g. melanoma). In some or any embodiments, the disease to be reduced, ameliorated, treated, or prevented is cancer (e.g. melanoma).

In certain embodiments, the disease to be reduced, ameliorated, treated, or prevented is cancer, a dermal rasopathy, a dermal disorder associated with neurofibromatosis type 1, a dermal neurofibroma, a cutaneous neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In certain embodiments, the disease to be reduced, ameliorated, treated, or prevented is cancer. In certain embodiments, the disease to be reduced, ameliorated, treated, or prevented is selected from the group consisting of basal cell carcinoma, squamous cell carcinoma, aktinic keratosis, Kaposi's sarcoma, dermal lymphoma, cervical cancer, HPV-related squamous cell carcinoma, and melanoma.

In certain embodiments, the disease to be reduced, ameliorated, treated, or prevented is a dermal rasopathy, a dermal disorder associated with neurofibromatosis type 1, a dermal neurofibroma, a cutaneous neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In some embodiments, the compounds described herein are used for the reduction of MEK-inhibitor responsive disorder or disease, MEK-inhibitor responsive dermal disorder or disease, MEK-mediated disorder or disease or a MEK-mediated dermal disorder or disease or of a where the subject is in need thereof In some embodiments, the compounds described herein are used for the amelioration of MEK-inhibitor responsive disorder or disease, MEK-inhibitor responsive dermal disorder or disease, MEK-mediated disorder or disease, or a MEK-mediated dermal disorder or disease or of a where the subject is in need thereof In some embodiments, the compounds described herein are used for prevention of MEK-inhibitor responsive disorder or disease, MEK-inhibitor responsive dermal disorder or disease, MEK-mediated disorder or disease, or a MEK-mediated dermal disorder or disease where the subject is in need thereof.

In some embodiments, the compounds described herein are used for treatment of MEK-inhibitor responsive disorder or disease, MEK-inhibitor responsive dermal disorder or disease, MEK-mediated disorder or disease, or a MEK-mediated dermal disorder or disease or of a where the subject is in need thereof.

Assay Methods

Compounds can be assayed for efficacy in treating a MEK-inhibitor responsive disorder or disease, MEK-inhibitor responsive dermal disorder or disease, MEK-mediated disorder or disease, or a MEK-mediated dermal disorder or disease where the subject is in need thereof according to any assay known to those of skill in the art. Exemplary assay methods are provided elsewhere herein.

Second Therapeutic Agents

In certain embodiments, the compounds and compositions provided herein are useful in methods of treatment of MEK-inhibitor responsive disorder or disease, MEK-inhibitor responsive dermal disorder or disease, MEK-mediated disorder or disease, or a MEK-mediated dermal disorder or disease where the subject is in need thereof, that comprise further administration of a second agent effective for the treatment of dermal disorders or diseases. The second agent can be any agent known to those of skill in the art to be effective for the treatment of dermal disorders or diseases, including those currently approved by the United States Food and Drug Administration, or other similar body of a country foreign to the United States.

In certain embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce one or more adverse or unwanted side effects associated with the use of either therapy alone.

The active compounds provided herein can be administered in combination or alternation with another therapeutic agent, in particular an agent effective in the treatment of MEK-inhibitor responsive disorder or disease, MEK-inhibitor responsive dermal disorder or disease, MEK-mediated disorder or disease, or a MEK-mediated dermal disorder or disease where the subject is in need thereof. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the MEK-inhibitor responsive disorder or disease, MEK-inhibitor responsive dermal disorder or disease, MEK-mediated disorder or disease, or the MEK-mediated dermal disorder or disease or a disorder to be alleviated. It is to be further understood that for any particular subject, specific dosage regimens and schedules should be adjusted over time according to the individual need and the professional judgment of the person administering or supervising the administration of the compositions.

EXAMPLES

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art. As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: h (hour); g (grams); mg (milligrams); mL (milliliters); L (microliters); mM (millimolar); M (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DIPEA (diisopropylethylamine); DMF (dimethyl formamide); DMSO (dimethylsulfoxide); DMSO-d$_6$ (deuterated dimethylsulfoxide); EtOAc (ethyl acetate); MeOH (methanol); TFAA (trifluoroacetic anhydride); UPLC-MS (ultra performance liquid chromatography-mass spectrometry).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Preparation of Compounds

Scheme 1

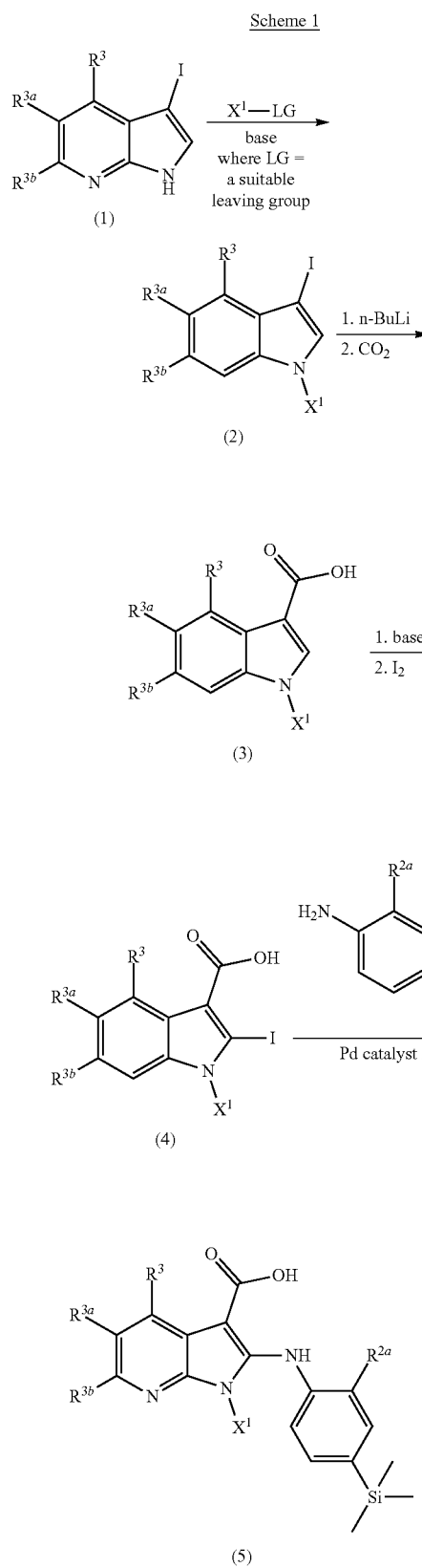

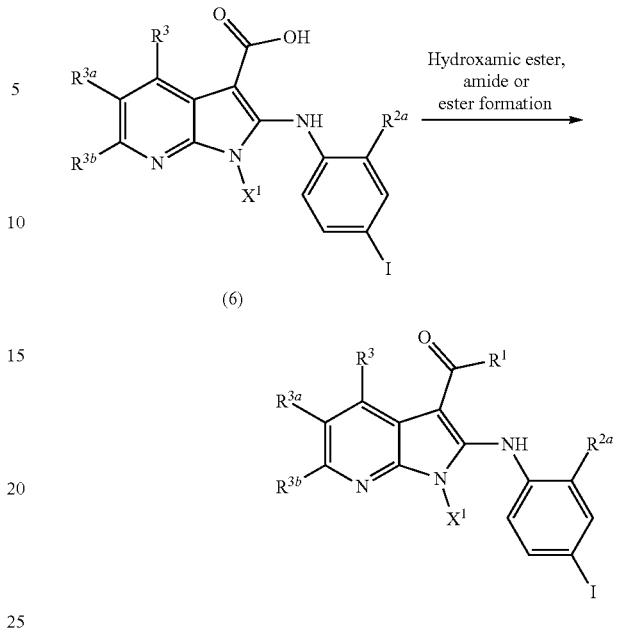

Compounds may be prepared according to Scheme 1 starting from the commercially available intermediate (1) where $X^1$ (which is, in some embodiments, methyl); $R^1$ is —$OR^4$, —$NR^5R^{5a}$, or an N-linked heterocycloalkyl where the N-linked heterocycloalkyl is optionally substituted with one or two $R^{10}$; $R^{2a}$ is halo or $C_1$-$C_6$ alkyl; and $R^3$, $R^{3a}$, and $R^{3b}$ are independently hydrogen, $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy; $C_3$-$C_8$-cycloalkyloxy; heterocycloalkyloxy; heteroaryloxy, or phenoxy where each phenyl and heteroaryl is independently optionally substituted with 1, 2, or 3 $R^6$; $R^3$, $R^{3a}$, and $R^{3b}$ are independently hydrogen, $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy; $C_3$-$C_8$-cycloalkyloxy; heterocycloalkyloxy; heteroaryloxy, or phenoxy where each phenyl and heteroaryl is independently optionally substituted with 1, 2, or 3 $R^6$. Intermediate (6) may be treated with using procedures described herein and below for Scheme 4.

Scheme 2

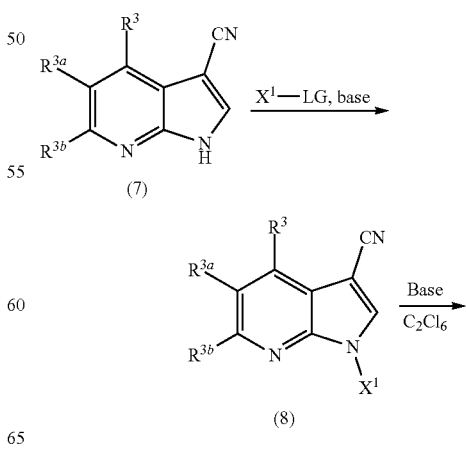

-continued

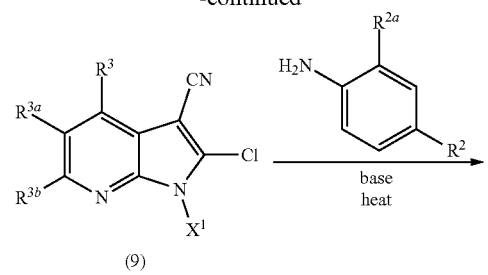

(9)

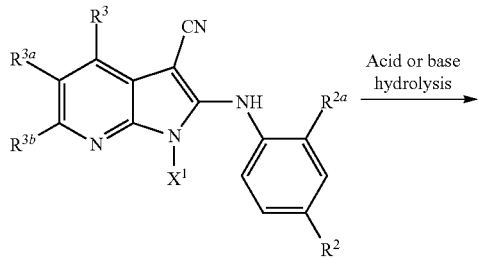

(10)

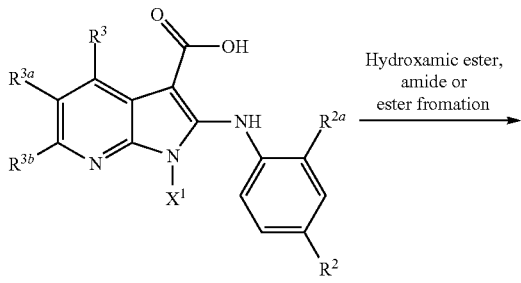

(11)

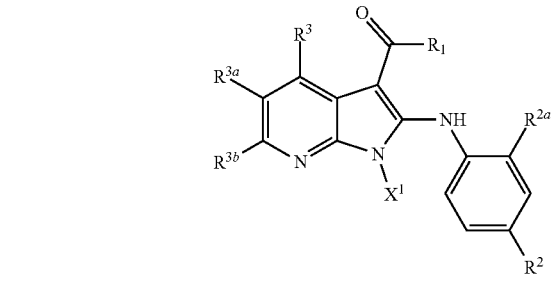

Scheme 3

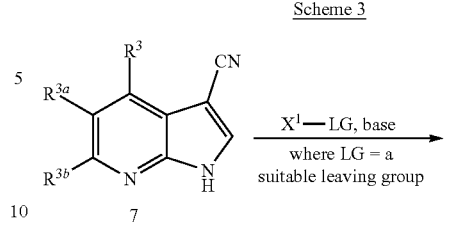

7

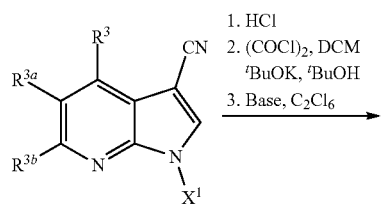

(8)

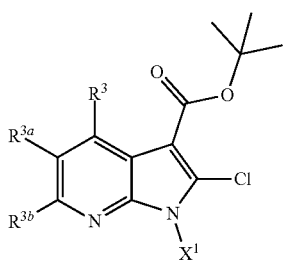

(12)

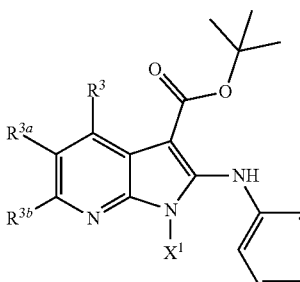

(13)

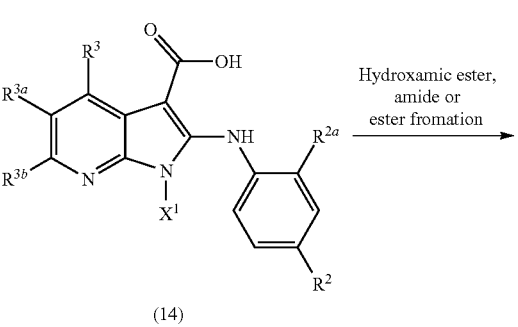

(14)

Compounds may be prepared according to Scheme 2 starting from the commercially available or readily accessible intermediate of formula (7) where $X^1$ (which is, in some embodiments, methyl); $R^1$ is —$OR^4$, —$NR^5R^{5a}$, or an N-linked heterocycloalkyl where the N-linked heterocycloalkyl is optionally substituted with one or two $R^{10}$; $R^2$ is —S—$C_1$-$C_6$ alkyl, $C_1$-$C_6$ alkyl, $C_2$-$C_6$ alkenyl, $C_2$-$C_6$ alkynyl, or halo; $R^{2a}$ is halo or $C_1$-$C_6$ alkyl; and $R^3$, $R^{3a}$, and $R^{3b}$ are independently hydrogen, $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy; $C_3$-$C_8$-cycloalkyloxy; heterocycloalkyloxy; heteroaryloxy, or phenoxy where each phenyl and heteroaryl is independently optionally substituted with 1, 2, or 3 $R^6$; $R^3$, $R^{3a}$, and $R^{3b}$ are independently hydrogen, $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy; $C_3$-$C_8$-cycloalkyloxy; heterocycloalkyloxy; heteroaryloxy, or phenoxy where each phenyl and heteroaryl is independently optionally substituted with 1, 2, or 3 $R^6$. Intermediate (11) of Scheme 2 can be converted using procedures described herein and below for Scheme 4.

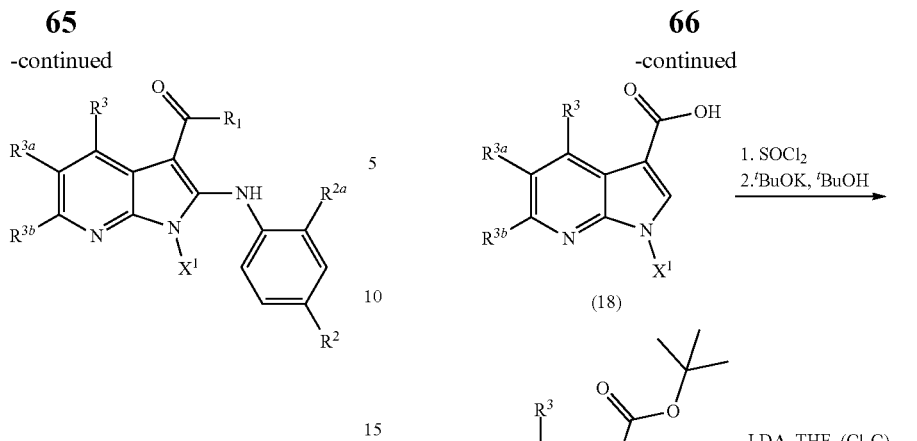

Compounds may be prepared according to Scheme 3 starting from the commercially available or readily accessible intermediate of formula (7) where $X^1$ (which is, in some embodiments, methyl); $R^1$ is —$OR^4$, —$NR^5R^{5a}$, or an N-linked heterocycloalkyl where the N-linked heterocycloalkyl is optionally substituted with one or two $R^{10}$; $R^2$ is —S—$C_1$-$C_6$ alkyl, $C_1$-$C_6$ alkyl, $C_2$-$C_6$ alkenyl, $C_2$-$C_6$ alkynyl, or halo; $R^{2a}$ is halo or $C_1$-$C_6$ alkyl; and $R^3$, $R^{3a}$, and $R^{3b}$ are independently hydrogen, $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy; $C_3$-$C_8$-cycloalkyloxy; heterocycloalkyloxy; heteroaryloxy, or phenoxy where each phenyl and heteroaryl is independently optionally substituted with 1, 2, or 3 $R^6$; $R^3$, $R^{3a}$, and $R^{3b}$ are independently hydrogen, $C_1$-$C_6$ alkyl, $C_2$-$C_6$ alkenyl, $C_2$-$C_6$ alkynyl, —S—$C_1$-$C_6$ alkyl, halo, $C_1$-$C_6$-alkoxy; $C_3$-$C_8$-cycloalkyloxy; heterocycloalkyloxy; heteroaryloxy, or phenoxy where each phenyl and heteroaryl is independently optionally substituted with 1, 2, or 3 $R^6$. Intermediate (14) of Scheme 3 can be converted using procedures described herein and below for Scheme 4.

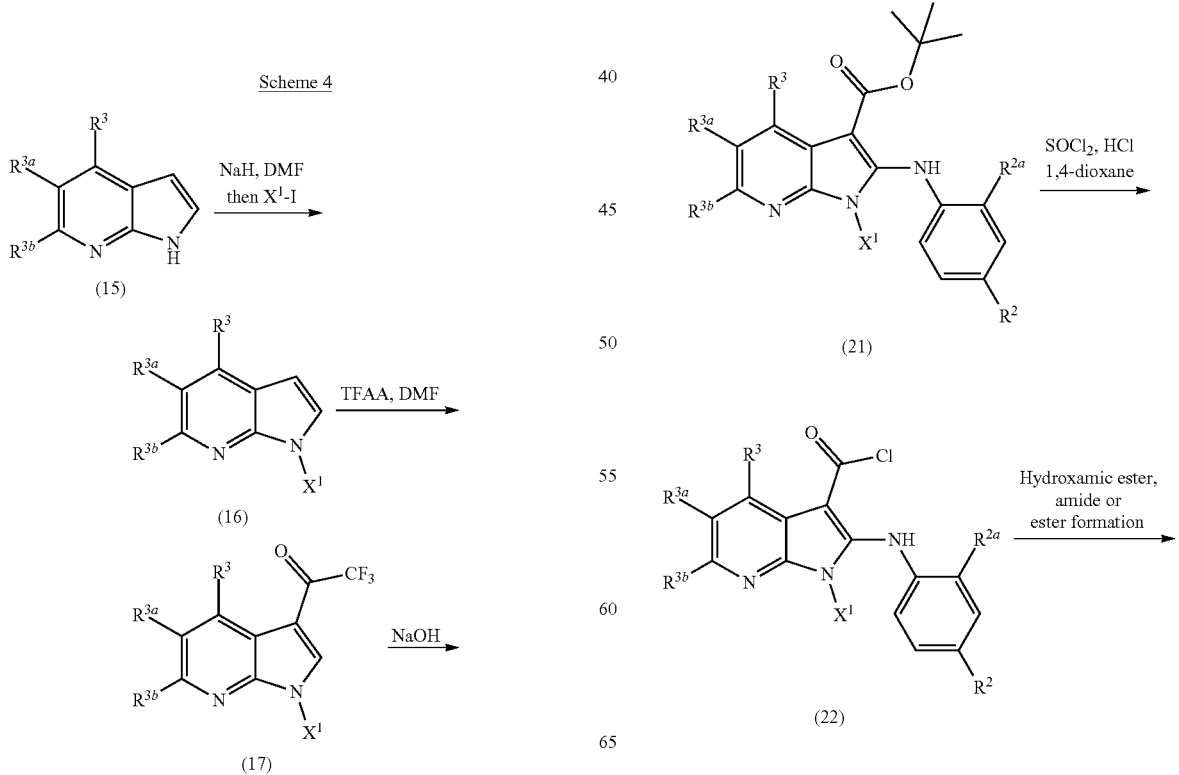

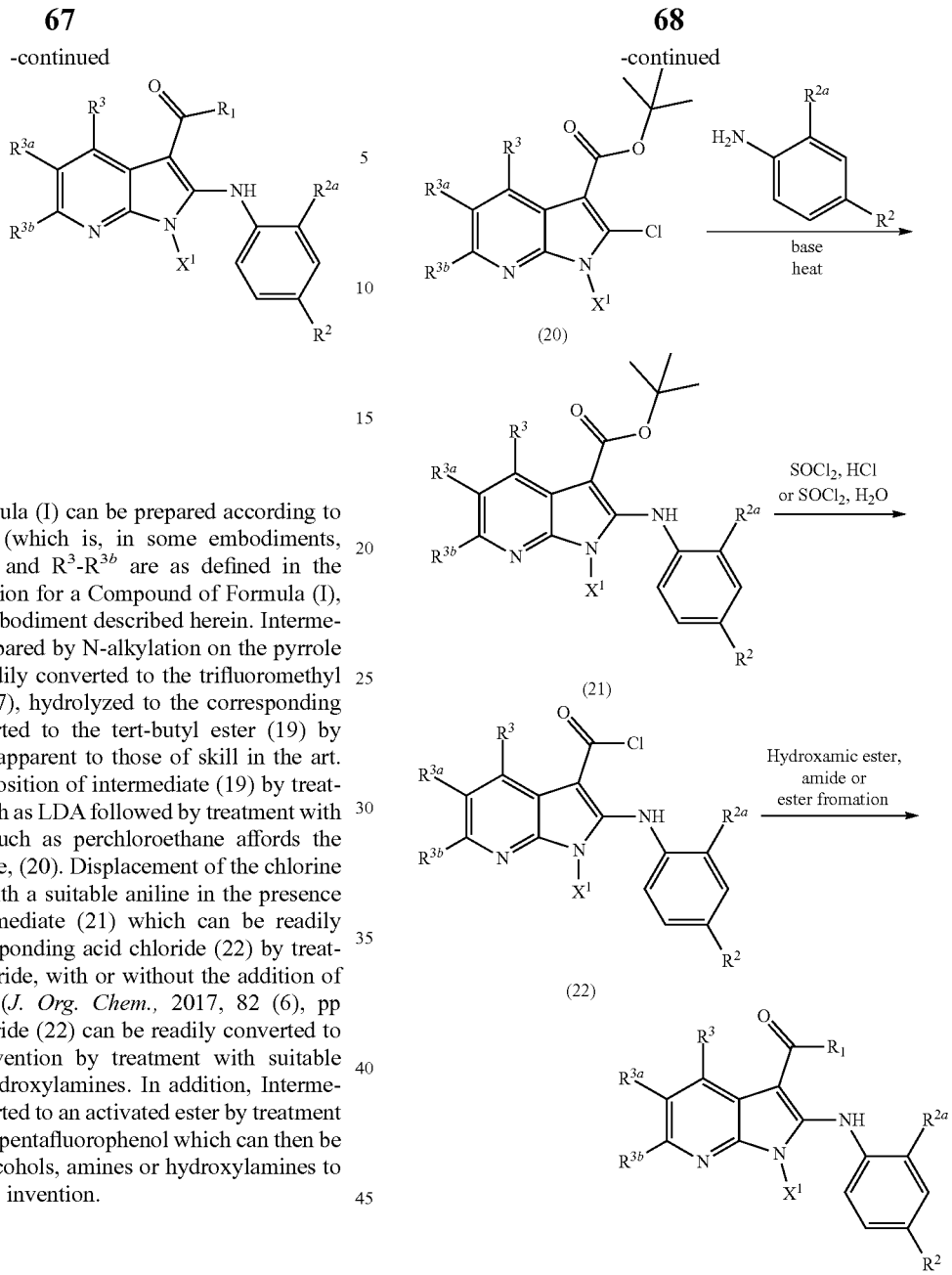

Compounds of Formula (I) can be prepared according to Scheme 4, where $X^1$ (which is, in some embodiments, methyl), $R^1$, $R^2$, $R^{2a}$, and $R^3$-$R^{3b}$ are as defined in the Summary of the Invention for a Compound of Formula (I), or as defined in any embodiment described herein. Intermediate (16) which is prepared by N-alkylation on the pyrrole nitrogen of (15) is readily converted to the trifluoromethyl ketone intermediate (17), hydrolyzed to the corresponding acid, (18), and converted to the tert-butyl ester (19) by esterification methods apparent to those of skill in the art. Chlorination in the 2-position of intermediate (19) by treating (19) with a base such as LDA followed by treatment with a chlorinating agent such as perchloroethane affords the chlorinated intermediate, (20). Displacement of the chlorine of intermediate (20) with a suitable aniline in the presence of a base gives intermediate (21) which can be readily converted to the corresponding acid chloride (22) by treatment with thionyl chloride, with or without the addition of 4 N HCl in dioxane (*J. Org. Chem.*, 2017, 82 (6), pp 3245-3251). Acid chloride (22) can be readily converted to compounds of the invention by treatment with suitable alcohols, amines or hydroxylamines. In addition, Intermediate (22) can be converted to an activated ester by treatment with an alcohol such as pentafluorophenol which can then be treated with suitable alcohols, amines or hydroxylamines to give compounds of the invention.

Scheme 5

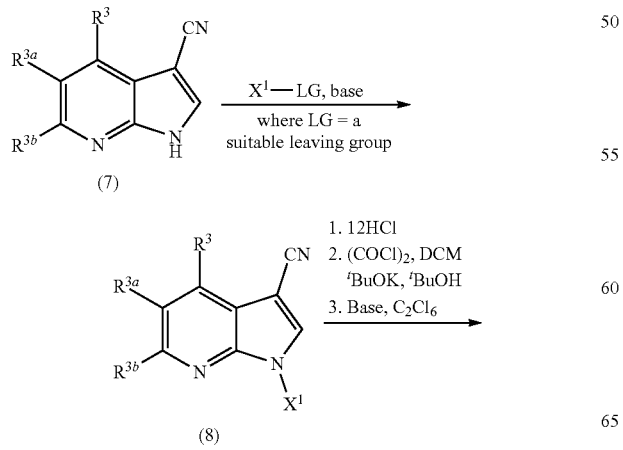

In addition, Compounds of Formula (I) may be prepared by the synthetic route given in Scheme 5 where $X^1$ (which is, in some embodiments, methyl), $R^1$, $R^2$, $R^{2a}$, and $R^3$-$R^{3b}$ are as defined in the Summary of the Invention for a Compound of Formula (I), or as defined in any embodiment described herein. Nitriles (8) which are prepared by N-alkylation on the pyrrole nitrogen of (7) can be hydrolyzed to the corresponding acids and esterified to form t-butyl esters (20). Then, following the sequence of Scheme 4, compounds of the invention may be prepared. Utilizing the Exemplary Preparation Schemes provided above and procedures known to one of ordinary skill in the art, the following compounds in Embodiment A can be prepared.

69
Embodiment A
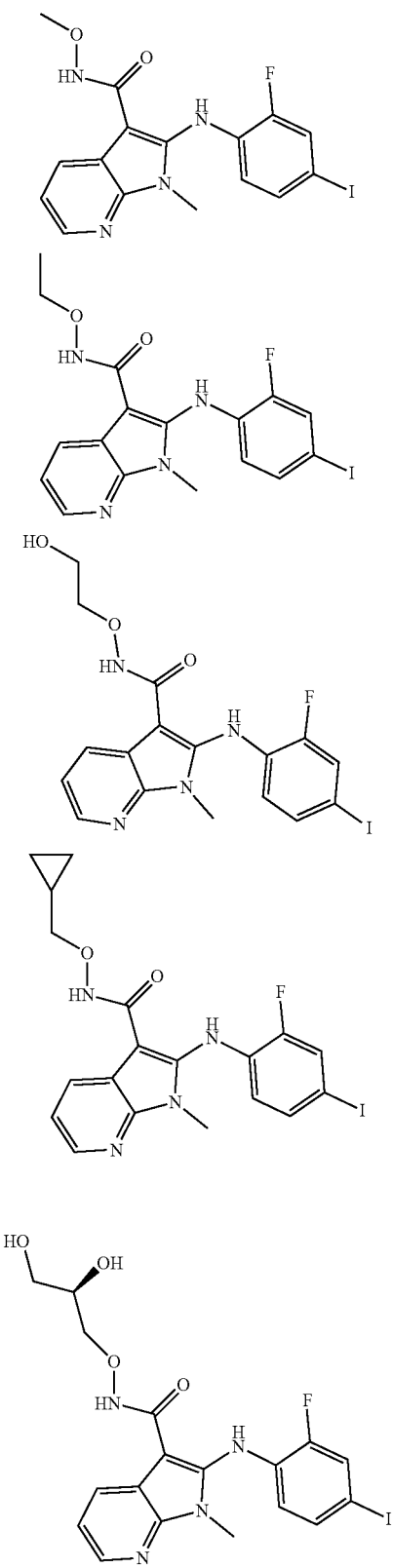
70
-continued
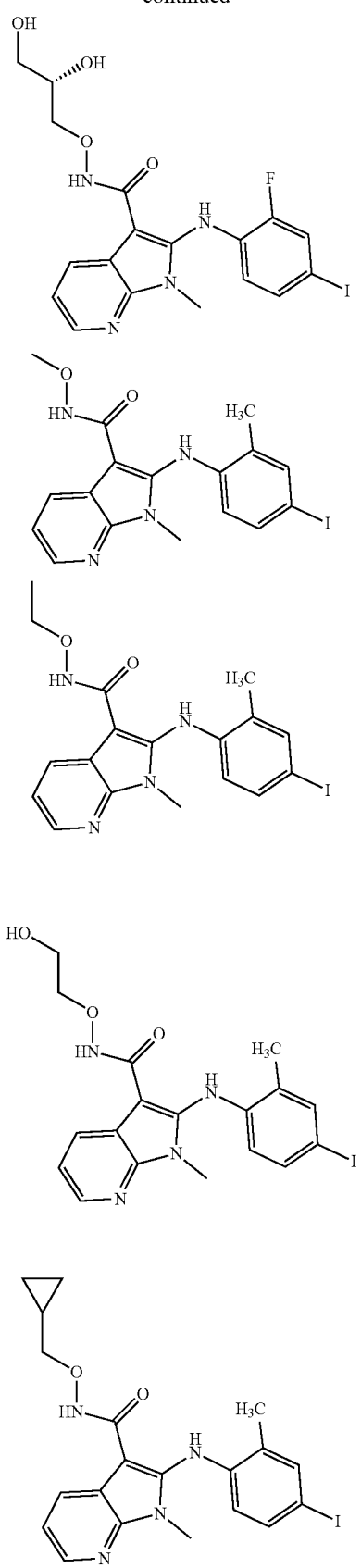

71
-continued
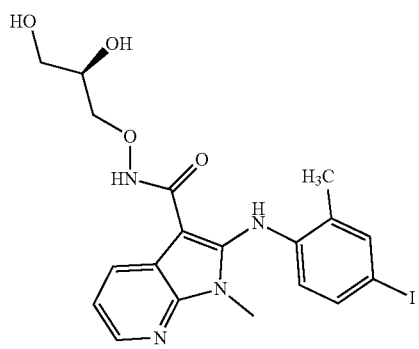
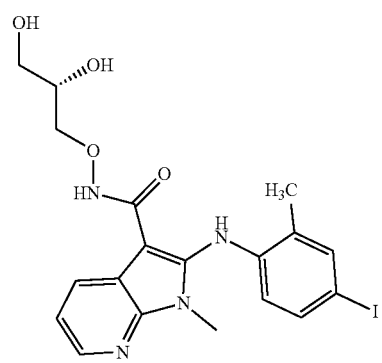
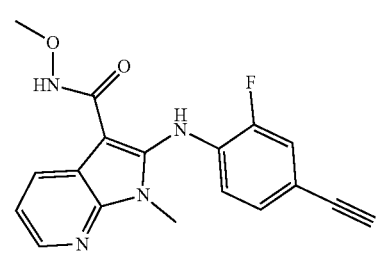
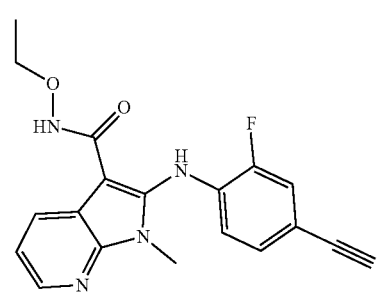
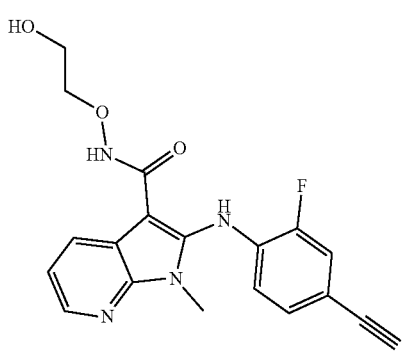
72
-continued
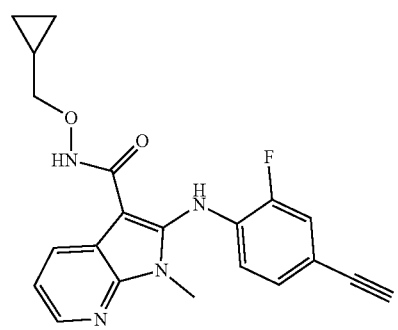
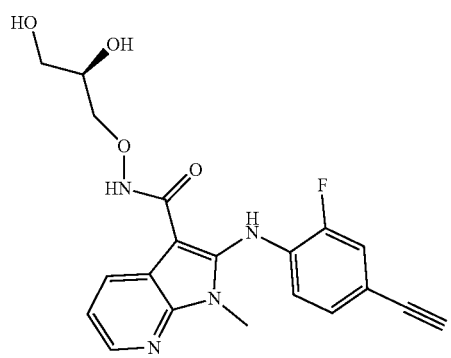
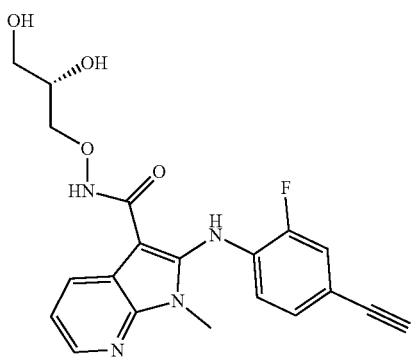
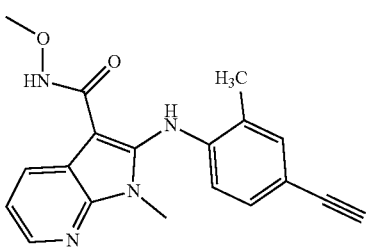
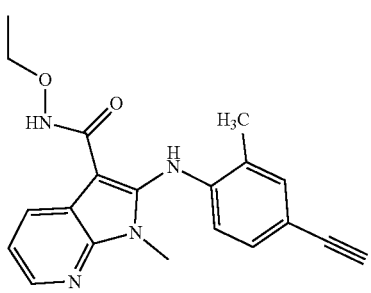

73
-continued
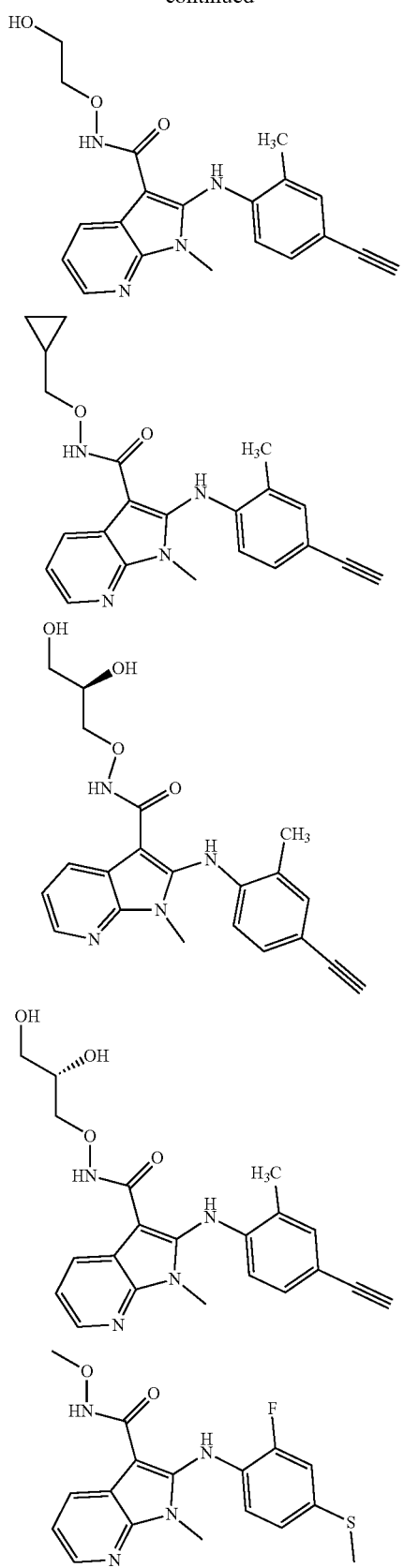
74
-continued
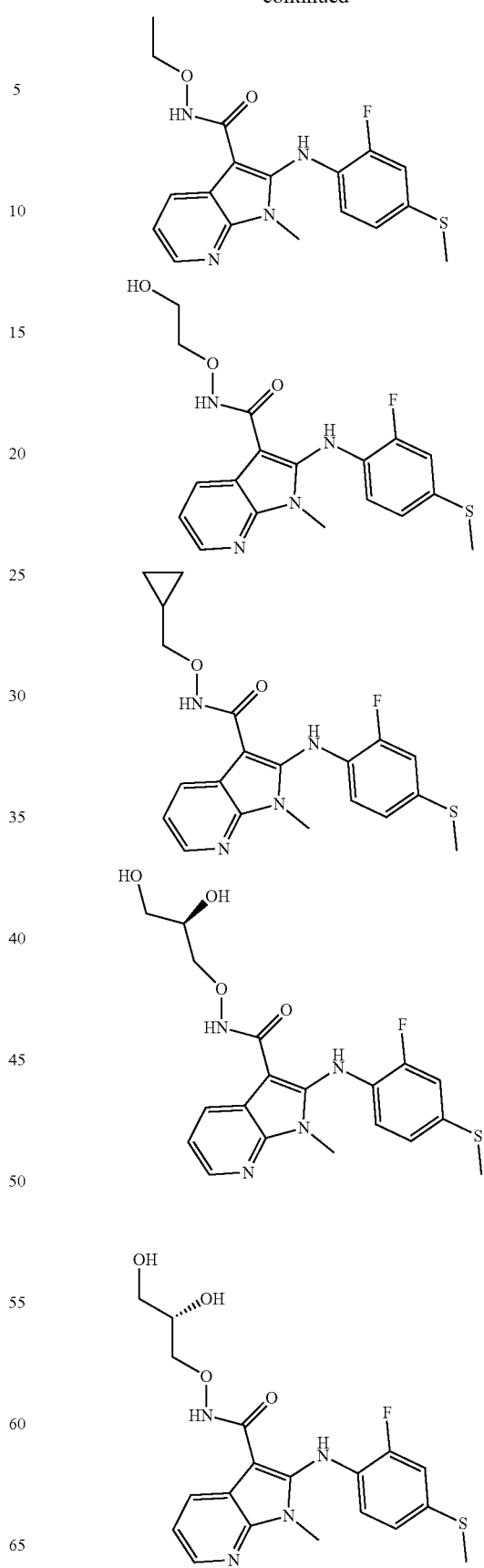

-continued
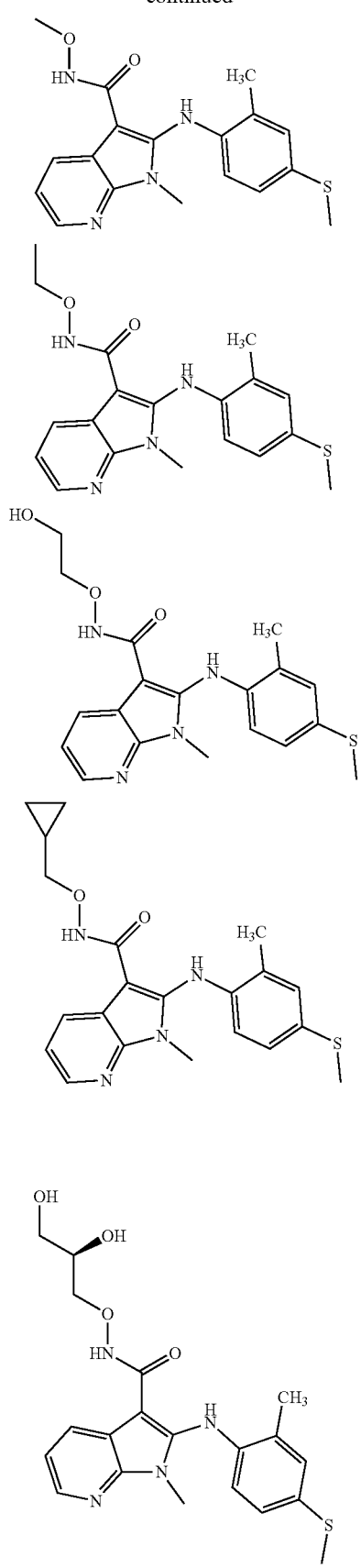
-continued
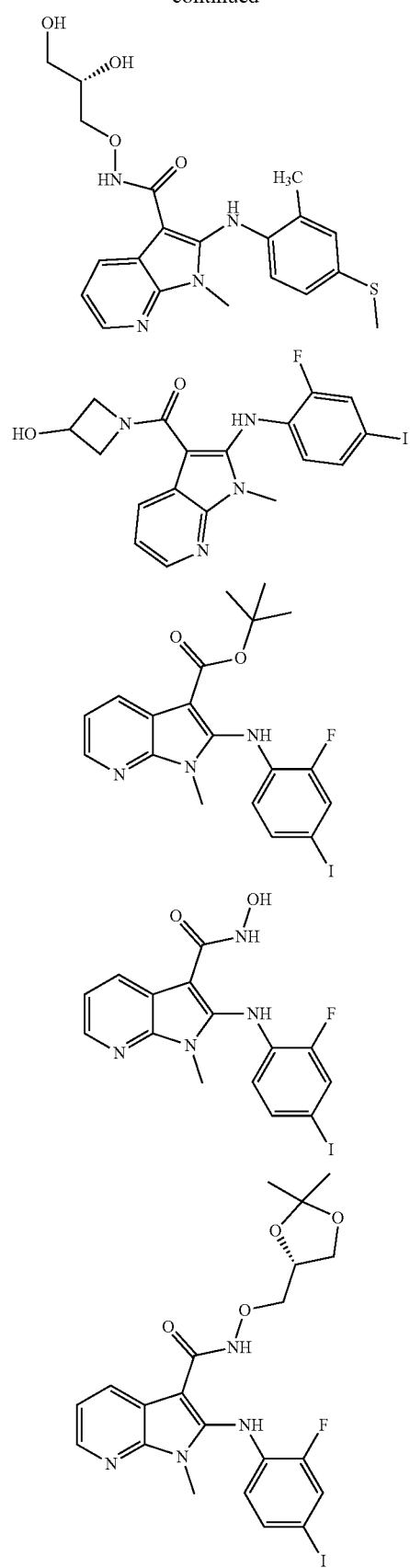

77

-continued

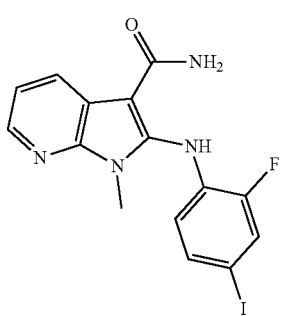

78

-continued

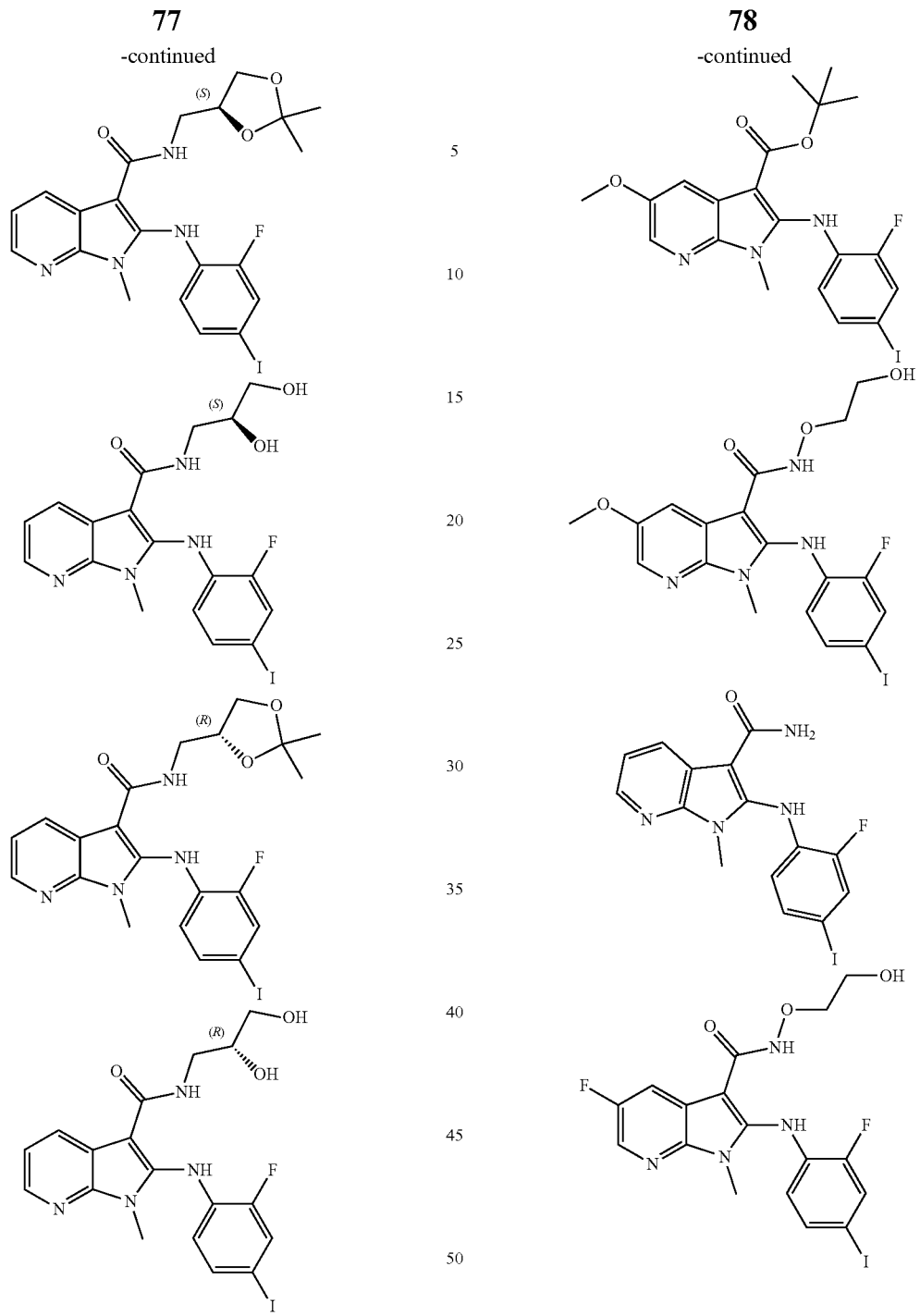

SYNTHETIC EXAMPLES

General Methods

NMR Spectroscopy $^1$H NMR spectra were recorded at 400 MHz on a Bruker Avance III NMR spectrometer. Samples were prepared in deuterated chloroform (CDCl$_3$) or dimethylsulphoxide (DMSO-d$_6$) and the raw data were processed using the ACD NMR software.

UPLC-MS Analysis

LCMS analysis was conducted on a Waters Acquity UPLC system consist of an Acquity i-Class Sample Manager-FL, Acquity i-Class Binary Solvent Manager and Acquity i-Class UPLC Column Manager. UV detection was achieved using an Acquity i-Class UPLC PDA detector (scanning from 210 to 400 nm), whereas mass detection was achieved using an Acquity QDa detector (mass scanning from 100-1250 Da; positive and negative modes simultaneously). A Waters Acquity UPLC BEH C18 column (2.1×50 mm, 1.7 m) was used to achieve the separation of the analytes.

Samples were prepared by dissolving (with or without sonication) into 1 mL of a 1:1 (v/v) mixture of MeCN in $H_2O$. The resulting solutions were filtered through a 0.2 μm syringe filter before being submitted for analysis. All of the solvents (including formic acid and 36% ammonia solution) used were used as the HPLC grade.

Four different analytical methods were used for this work, the details of which are presented below.

Acidic run (2 min): 0.1% v/v Formic acid in water [Eluent A]; 0.1% v/v Formic acid in MeCN [Eluent B]; Flow rate 0.8 mL/min; injection volume 2 μL and 1.5 min equilibration time between samples.

| Time (min) | Eluent A (%) | Eluent B (%) |
|---|---|---|
| 0.00 | 95 | 5 |
| 0.25 | 95 | 5 |
| 1.25 | 5 | 95 |

| Time (min) | Eluent A (%) | Eluent B (%) |
|---|---|---|
| 1.55 | 5 | 95 |
| 1.65 | 95 | 5 |
| 2.00 | 95 | 5 |

Acidic run (4 mini): 0.100 v/v formic acid in water [Eluent A]; 0.10% v/v formic acid in MeCN [Eluent B]; Flow rate 0.8 mL/min; injection volume 2 μL and 1.5 min equilibration time between samples.

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Basic run (2 mini): 0.10% ammonia in water [Eluent A]; 0.100 ammonia in MeCN [Eluent B]; Flow rate 0.8 mL/min; injection volume 2 μL and 1.5 min equilibration time between samples.

| Time (min) | Eluent A (%) | Eluent B (%) |
|---|---|---|
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Basic run (4 min): 0.10% ammonia in water [Eluent A]; 0.100 ammonia in MeCN [Eluent B]; Flow rate 0.8 mL/min; injection volume 2 μL and 1.5 min equilibration time between samples.

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Example 1: tert-Butyl 2-((2-fluoro-4-iodophenyl) amino)-1-methyl-1H-pyrrolo[2,3-b]pyridine-3-carboxylate Alternative A for Preparation of 1-Methyl-1H-pyrrolo[2,3-b]pyridine-3-carboxylic Acid Step 1 of Alternative A: 1-Methyl-1H-pyrrolo[2,3-b]pyridine-3-carbonitrile

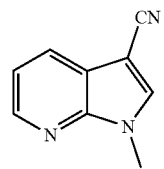

A solution of 7-azaindole-3-carbonitrile (9.0 g, 62.8 mmol) in dry DMF (80 mL) was cooled to 0° C. in an ice bath and treated with sodium hydride (5.0 g, 125.7 mmol, 60% in mineral oil) in a portion-wise manner. The resulting mixture was stirred for 45 min at 0° C., then treated with iodomethane (7.8 mL, 125.7 mmol) and gradually warmed up to a room temperature over 1 h. The mixture was then cautiously poured into $H_2O$ (450 mL) and extracted with EtOAc (3×50 mL). The combined organic phases were washed sequentially with water (3×50 mL) and brine, dried over $Na_2SO_4$, filtered, and concentrated in vacuo. The crude was purified by flash column chromatography (Silica 120 g, 10-50% EtOAC in hexane) to give the product (7.3 g, 74%) as an off-white solid. UPLC-MS (Acidic Method, 4 min): rt 2.30 min, m z 158.2 [M+H]$^+$. $^1$H NMR (400 MHz, CDCl$_3$) δ ppm 8.48 (dd, J=4.7, 1.5 Hz, 1H), 8.09 (dd, J=7.9, 1.6 Hz, 1H), 7.75 (s, 1H), 7.25-7.30 (m, 1H), 3.98 (s, 3H).

Step 2 of Alternative A: 1-Methyl-1H-pyrrolo[2,3-b]pyridine-3-carboxylic Acid

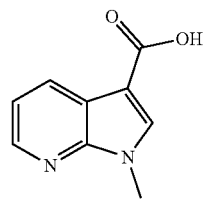

A suspension of 1-methyl-1H-pyrrolo[2,3-b]pyridine-3-carbonitrile (7.3 g, 46.5 mmol) in concentrated hydrochloric acid (12 M, 73 mL, 876 mmol) was heated at 100° C. with stirring for 10 h, resulting in a clear solution. The reaction mixture was then cooled to 5° C. (ice bath) and cautiously treated with 40% NaOH aqueous solution until the pH reached 2 leading to a formation of a white precipitate. The resulting mixture was stirred for 1 h, filtered, and the solid was washed with $H_2O$ until the filtrate became pH neutral before being dried in vacuo to give the product (6.9 g, 84%) as a white solid. UPLC-MS (Basic Method, 2 min): rt 0.17 min, m z 175.2 [M+H]⁺. ¹H NMR (400 MHz, DMSO-$d_6$) δ ppm 8.28-8.37 (m, 2H), 8.22 (s, 1H), 7.25 (dd, J=7.8, 4.7 Hz, 1H), 3.86 (s, 3H).

Alternative B for Preparation of 1-Methyl-1H-pyrrolo[2,3-b]pyridine-3-carboxylic Acid Step 1 of Alternative B:
1-methyl-1H-pyrrolo[2,3-b]pyridine

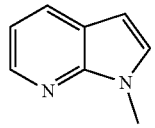

To a suspension of sodium hydride, 60% dispersion in mineral oil (36.5 g, 914 mmol), in anhydrous DMF (300 mL) cooled in an ice bath was added a solution of 7-azaindole (90.0 g, 762 mmol) in DMF (200 mL) via addition funnel over 3 h. The reaction mixture was stirred for 30 minutes and cooled in an ice bath before methyl iodide (52 mL, 838 mmol) was added via dropping funnel over 30 minutes. After stirring the reaction mixture at r.t. over the weekend, UPLC analysis showed the reaction was incomplete. Additional methyl iodide (5 mL, 80.3 mmol) was added and the reaction monitored by UPLC until completion. The reaction mixture was cooled in an ice bath and quenched with $H_2O$, extracted into EtOAc (3×800 mL) and the combined organic layers were washed with brine, dried over $Na_2SO_4$, and the solvent removed in vacuo to give the desired product (130.7 g (89.4 g, 89% active compound)) as a dark brown biphasic oil. UPLC-MS (Acidic Method, 2 min): rt 0.75 min, m z 133.1 [M+H]⁺. ¹H NMR (400 MHz, DMSO-$d_6$) δ ppm 8.25 (dd, J=4.6, 1.5 Hz, 1H), 7.94 (dd, J=7.8, 1.5 Hz, 1H), 7.50 (d, J=3.4 Hz, 1H), 7.07 (dd, J=7.8, 4.7 Hz, 1H), 6.45 (d, J=3.4 Hz, 1H), 3.82 (s, 3H).

Step 2 of Alternative B: 2,2,2-trifluoro-1-(1-methyl-1H-pyrrolo[2,3-b]pyridin-3-yl)ethanone

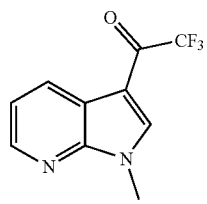 [SMILES: Cn1cc(C(=O)C(F)(F)F)c2cccnc21]

To a solution of 1-methyl-1H-pyrrolo[2,3-b]pyridine (89.4 g, 676 mmol) in DMF (450 mL) cooled in an ice bath, was added TFAA (141 mL, 1.01 mol) dropwise via addition funnel over 3 h. The reaction was stirred at r.t. overnight before dilution with $H_2O$ (1 L) over 1 h. Addition of $H_2O$ resulted in precipitate formation, which was stirred for 30 minutes before filtration. The solid was washed with $H_2O$ and dried to give the desired product (121 g, 79%) as a white solid. UPLC-MS (Acidic Method, 2 min): rt 1.05 min, m z 229.1 [M+H]⁺. ¹H NMR (400 MHz, DMSO-$d_6$) δ ppm: 8.80 (d, J=1.5 Hz, 1H), 8.52 (q, J=1.5 Hz, 1H), 8.50 (s, 1H), 7.40-7.49 (m, 1H), 3.97 (s, 3H); ¹⁹F NMR (376 MHz, DMSO-$d_6$) δ ppm: −71.6 (s, 1F).

Step 3 of Alternative B: 1-methyl-1H-pyrrolo[2,3-b]pyridine-3-carboxylic Acid

To a flask containing solid 2,2,2-trifluoro-1-(1-methyl-1H-pyrrolo[2,3-b]pyridin-3-yl)ethenone (89.9 g, 394 mmol) was added 5 M NaOH (788 mL, 3.94 mol), the resultant mixture was heated to 50° C. overnight. The reaction mixture was diluted by 50% with $H_2O$ and washed with TBME (800 mL). The resultant aqueous layer was acidified to pH 1 with concentrated HCl (330 mL), resulting in formation of a white precipitate. The precipitate was filtered, washed with $H_2O$ (1.2 L) and dried under vacuum at 40° C., to a constant weight giving the desired product (69.9 g, 99%) as a white solid. UPLC-MS (Basic Method, 2 min): rt 0.17 min, m z 175.2 [M+H]⁺. ¹H NMR (400 MHz, DMSO-$d_6$) δ ppm 8.28-8.37 (m, 2H), 8.22 (s, 1H), 7.25 (dd, J=7.8, 4.7 Hz, 1H), 3.86 (s, 3H Alternative 1 for the Preparation of tert-Butyl 1-methyl-1H-pyrrolo[2,3-b]pyridine-3-carboxylate

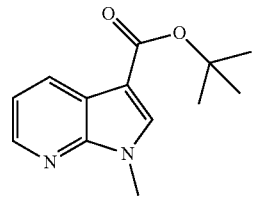 [SMILES: Cn1cc(C(=O)OC(C)(C)C)c2cccnc21]

To a suspension of 1-methyl-1H-pyrrolo[2,3-b]pyridine-3-carboxylic acid (10.0 g, 56.8 mmol), prepared as described above in Alternative A or B, in anhydrous DCM (390 mL) cooled on ice, oxalyl chloride (14.4 mL, 170.4 mmol) was added dropwise over 15 min and the mixture was stirred at room temperature for 2 h. The mixture was then concentrated in vacuo to give a yellow solid, which was treated with tert-butanol (300 mL, 3.14 mol), followed by an addition of potassium tert-butoxide (10.2 g, 91 mmol). The resulting mixture was stirred at room temperature for 16 h and then concentrated in vacuo. The crude was purified by flash column chromatography (Silica 120 g, 0-10% MeOH in DCM) to give the product (12.6 g, 86%) as a light brown solid. UPLC-MS (Acidic Method, 2 min): rt 1.10 min, m z 233.1 [M+H]⁺. ¹H NMR (400 MHz, DMSO-$d_6$) δ ppm 8.35 (dd, J=4.6, 1.6 Hz, 1H), 8.27 (dd, J=7.8, 1.6 Hz, 1H), 8.20 (s, 1H), 7.27 (dd, J=7.9, 4.6 Hz, 1H), 3.86 (s, 3H), 1.56 (s, 9H).

Alternative 2 for the Preparation of tert-Butyl 1-methyl-1H-pyrrolo[2,3-b]pyridine-3-carboxylate 1-Methyl-1H-pyrrolo[2,3-b]pyridine-3-carboxylic acid (68.7 g, 390 mmol), prepared as described above in Alternative A or B, was added to thionyl chloride (700 mL, 9.67 mol) under stirring at room temperature, and the resulting mixture was stirred overnight. The thionyl chloride was then removed under vacuum to give a thick suspension, which was co-distilled from toluene (3×200 mL) to give an off-white solid. This material was subsequently suspended in tert-butanol (500 mL). Solid potassium tert-butoxide (70 g, 624 mmol) was added to the suspension in a portion-wise manner, and the resulting mixture was stirred overnight. The solvent was removed under vacuum to give a thick solid, which was partitioned between EtOAc (1.5 L) and a saturated solution of aqueous NaHCO$_3$ (1 L). The organic phase was collected and washed with a saturated solution of aqueous NaHCO$_3$ (1 L), before being dried over Na$_2$SO$_4$, filtered and evaporated to dryness to give the desired product (66.7 g, 74%) as a green solid.

tert-Butyl 2-chloro-1-methyl-1H-pyrrolo[2,3-b]pyridine-3-carboxylate

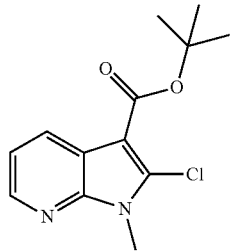 [SMILES: Cn1c(Cl)c(C(=O)OC(C)(C)C)c2cccnc21]

A solution of tert-butyl 1-methyl-1H-pyrrolo[2,3-b]pyridine-3-carboxylate (4.8 g, 21.0 mmol) in dry THF (90 mL), prepared as described in Alternative 1 or Alternative 2 above, was flushed with N$_2$, cooled to −78° C. and then treated with a solution of LDA (2 M in THF, 21 mL, 42 mmol). The mixture was stirred at −78° C. for 0.5 h. A solution of hexachloroethane (9.9 g, 42.0 mmol) in dry THF (30 mL) was added and the mixture was gradually warmed up to a room temperature and stirred for 1.5 h. The mixture was treated with saturated NH$_4$Cl aqueous solution and extracted with EtOAc (3×50 mL). The combined organic phases were dried over Na$_2$SO$_4$, filtered and concentrated in vacuo. The crude was purified by flash column chromatography (Silica 80 g, 0-12% EtOAc in hexanes) to give the product (4.5 g, 81%) as a pale-yellow solid. UPLC-MS (Acidic Method, 2 min): rt 1.21 min, m z 267.1/269.0 [M+H]$^+$. $^1$H NMR (400 MHz, DMSO-d$_6$) δ ppm 8.37 (dd, J=4.8, 1.6 Hz, 1H), 8.27 (dd, J=7.9, 1.6 Hz, 1H), 7.32 (dd, J=7.9, 4.7 Hz, 1H), 3.83 (s, 3H), 1.58 (s, 9H)

tert-Butyl 2-((2-fluoro-4-iodophenyl)amino)-1-methyl-1H-pyrrolo[2,3-b]pyridine-3-carboxylate

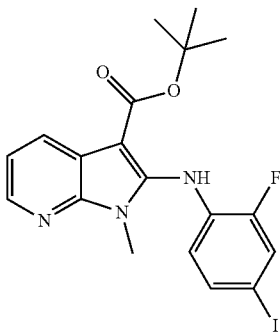 [SMILES: Cn1c(Nc2ccc(I)cc2F)c(C(=O)OC(C)(C)C)c2cccnc21]

A suspension of tert-butyl 2-chloro-1-methyl-1H-pyrrolo[2,3-b]pyridine-3-carboxylate (1.0 g, 3.8 mmol) and 2-fluoro-4-iodoaniline (0.8 g, 3.6 mmol) in dry THF (20 mL) was flushed with N$_2$, cooled to −78° C. and treated with a solution of LiHMDS (1 M in THF, 7.5 mL, 7.5 mmol). The mixture was gradually warmed up to room temperature and stirred for 3 h. The mixture was quenched with saturated NH$_4$Cl aqueous solution and then extracted with EtOAc (3×50 mL). The combined organic phases were dried over Na$_2$SO$_4$, filtered, and concentrated in vacuo. The crude was purified by flash column chromatography (Silica 40 g, 0-12% EtOAc in hexanes) to give the product (1.5 g, 87%) as a yellow solid. UPLC-MS (Acidic Method, 2 min): rt 1.42 min, m z 468.1 [M+H]$^+$. $^1$H NMR (400 MHz, DMSO-d$_6$) δ ppm 8.57 (s, 1H), 8.24 (dd, J=4.8, 1.6 Hz, 1H), 8.16 (dd, J=7.8, 1.6 Hz, 1H), 7.63 (dd, J=10.8, 2.0 Hz, 1H), 7.37 (dt, J=8.5, 0.9 Hz, 1H), 7.23 (dd, J=7.8, 4.8 Hz, 1H), 6.68 (t, J=8.8 Hz, 1H), 3.55 (s, 3H), 1.41 (s, 9H)

Example 2: 2-((2-Fluoro-4-iodophenyl)amino)-N-(2-hydroxyethoxy)-1-methyl-1H-pyrrolo[2,3-b]pyridine-3-carboxamide 2-((2-Fluoro-4-iodophenyl)amino)-1-methyl-1H-pyrrolo[2,3-b]pyridine-3-carbonyl Chloride

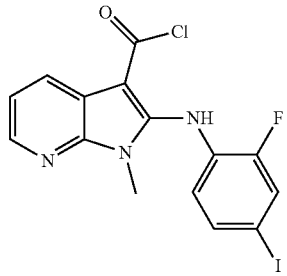 [SMILES: Cn1c(Nc2ccc(I)cc2F)c(C(=O)Cl)c2cccnc21]

To tert-butyl 2-((2-fluoro-4-iodophenyl)amino)-1-methyl-1H-pyrrolo[2,3-b]pyridine-3-carboxylate (0.6 g, 1.3 mmol), thionyl chloride (0.9 mL, 12.8 mmol) was added followed by H$_2$O (23 µL). The flask was sealed with a rubber septum and the mixture was stirred at room temperature for 18 h. The mixture was concentrated to dryness in vacuo to give the product (0.5 g, 94%) as a beige solid. UPLC-MS (Acidic Method, 2 min): rt 1.28 min, m z 426.0 [M+H]$^+$ (detected as the corresponding methyl ester after quenching an aliquot of the mixture with MeOH).

Alternative preparation: A stirred solution of tert-butyl 2-((2-fluoro-4-iodophenyl)amino)-1-methyl-1H-pyrrolo[2,3-b]pyridine-3-carboxylate (5.00 g, 10.7 mmol) in anhydrous 1,4-dioxane (28 mL) was treated with thionyl chloride (7.7 mL, 107 mmol) at ambient temperature, followed by a 4 N solution of hydrogen chloride in 1,4-dioxane (14 mL, 5.35 mmol), and the resulting mixture was heated to 50° C. for 48 h. The reaction mixture was cooled to 40° C. and subjected to a continuous distillation process under vacuum from anhydrous toluene (maintaining the total volume of the batch around 30 mL) to remove the thionyl chloride and 1,4-dioxane. The resulting dark grey suspension of 2-((2-fluoro-4-iodophenyl)amino)-1-methyl-1H-pyrrolo[2,3-b]pyridine-3-carbonyl chloride was used in subsequent steps without further purification. UPLC-MS (Acidic Method, 2 min): rt 1.29 min, m/z 426.0 [M+H]+ (following the quenching of an aliquot of the batch into methanol to give the corresponding methyl ester).

Alternative 1 for the preparation of 2-((2-Fluoro-4-iodophenyl)amino)-N-(2-hydroxyethoxy)-1-methyl-1H-pyrrolo[2,3-b]pyridine-3-carboxamide

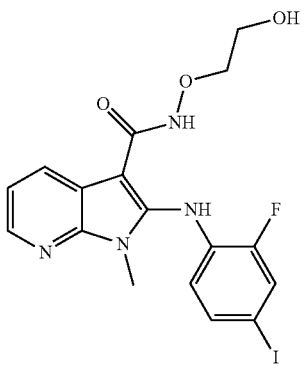 [SMILES: Cn1c(Nc2ccc(I)cc2F)c(C(=O)NOCCO)c2cccnc21]

A solution of 2-((2-fluoro-4-iodophenyl)amino)-1-methyl-1H-pyrrolo[2,3-b]pyridine-3-carbonyl chloride (460 mg, 1.07 mmol) in dry DCM (27 mL) was cooled to 0° C. in an ice bath and then treated with dry pyridine (970 µL, 11.98 mmol) and the mixture was stirred for 15 min followed by an addition of (2-aminooxy)ethanol (124 mg, 1.61 mmol) in dry DCM (2 mL). The mixture was stirred for 15 min, then diluted with DCM and acidified with 1 M citric acid aqueous solution to pH 3. The organic phase was washed with H$_2$O, brine, dried over Na$_2$SO$_4$ and concentrated in vacuo. The crude was purified by preparative HPLC to give the product (181 mg, 36%) as a white solid. UPLC-MS (Acidic Method, 4 min): rt 2.67 min, m z 471.2 [M+H]+. $^1$H NMR (400 MHz, DMSO-d$_6$) δ ppm 10.84 (br s, 1H), 8.69 (br s, 1H), 8.25 (dd, J=4.8, 1.4 Hz, 1H), 8.13 (dd, J=7.9, 1.5 Hz, 1H), 7.63 (dd, J=10.8, 1.9 Hz, 1H), 7.33 (dd, J=8.5, 1.1 Hz, 1H), 7.21 (dd, J=7.8, 4.8 Hz, 1H), 6.52 (t, J=8.8 Hz, 1H), 4.74 (br s, 1H), 3.79 (t, J=4.9 Hz, 2H), 3.48-3.54 (m, 5H)

Alternative 2 for the Preparation of 2-((2-Fluoro-4-iodophenyl)amino)-N-(2-hydroxyethoxy)-1-methyl-1H-pyrrolo[2,3-b]pyridine-3-carboxamide To a solution of 2-(aminooxy)ethanol (8.41 g, 109 mmol) in anhydrous THF (20 mL) at 0° C. was added a suspension of 2-((2-fluoro-4-iodophenyl)amino)-1-methyl-1H-pyrrolo[2,3-b]pyridine-3-carbonyl chloride (9.37 g, 21.8 mmol) in anhydrous THF (80 mL) and residual toluene via syringe. After 40 minutes UPLC analysis showed complete conversion. The reaction mixture was partitioned between EtOAc (300 mL) and H$_2$O (300 mL), the biphasic mixture was filtered and the organic layer separated. The aqueous layer was extracted with EtOAc (200 mL) and the organics combined, washed with brine, dried over Na$_2$SO$_4$ and the solvent removed in vacuo. The crude solid was suspended in EtOAc (40 mL, 4 volumes), stirred over the weekend and filtered to give the desired product (7.45 g, 73%) as a dark beige solid which can be recrystallized from anisole. UPLC-MS (Acidic Method, 2 min): rt 1.01 min, m z 471.2 [M+H]+. $^1$H NMR (400 MHz, DMSO-d$_6$) δ ppm 10.84 (br s, 1H), 8.69 (br s, 1H), 8.25 (dd, J=4.8, 1.4 Hz, 1H), 8.13 (dd, J=7.9, 1.5 Hz, 1H), 7.63 (dd, J=10.8, 1.9 Hz, 1H), 7.33 (dd, J=8.5, 1.1 Hz, 1H), 7.21 (dd, J=7.8, 4.8 Hz, 1H), 6.52 (t, J=8.8 Hz, 1H), 4.74 (br s, 1H), 3.79 (t, J=4.9 Hz, 2H), 3.48-3.54 (m, 5H).

Example 3: 2-((4-Ethynyl-2-fluorophenyl)amino)-N-(2-hydroxyethoxy)-1-methyl-1H-pyrrolo[2,3-b]pyridine-3-carboxamide 2-((2-Fluoro-4-((trimethylsilyl)ethynyl)phenyl)amino)-N-(2-hydroxyethoxy)-1-methyl-1H-pyrrolo[2,3-b]pyridine-3-carboxamide

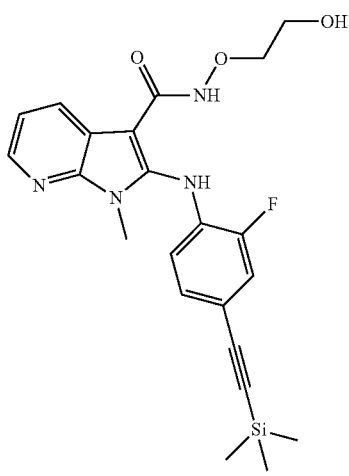 [SMILES: Cn1c(Nc2ccc(C#C[Si](C)(C)C)cc2F)c(C(=O)NOCCO)c2cccnc21]

A solution of 2-((2-fluoro-4-iodophenyl)amino)-N-(2-hydroxyethoxy)-1-methyl-1H-pyrrolo[2,3-b]pyridine-3-carboxamide (100 mg, 0.21 mmol, 71% pure by UPLC-MS), copper(I) iodide (1 mg, 0.004 mmol), PdCl$_2$(PPh$_3$)$_2$ (3 mg, 0.004 mmol) in dry THF (0.5 mL) flushed with N$_2$, trimethylsilylacetylene (32 µL, 0.23 mmol) in Et$_3$N (21 µL, 1.49 mmol) was added. The mixture was stirred at room temperature for 3 h. The mixture was diluted with Et$_2$O, filtered through a pad of Celite® and the filtrate was concentrated in vacuo. The crude was purified by flash column chromatography (Silica 4 g, 20-70% EtOAc in hexanes) to give the product (25 mg, 38%) as a colorless oil. UPLC-MS (Acidic Method, 2 min): rt 1.20 min, m z 441.1 [M+H]+. $^1$H NMR (400 MHz, DMSO-d$_6$) δ ppm 10.83 (s, 1H), 8.75 (s, 1H), 8.27 (dd, J=4.7, 1.6 Hz, 1H), 8.15 (dd, J=7.9, 1.5 Hz, 1H), 7.51-7.63 (m, 1H), 7.33 (dd, J=12.1, 1.8 Hz, 1H), 7.22 (dd, J=7.9, 4.8 Hz, 1H), 7.09 (dd, J=8.3, 1.6 Hz, 1H), 6.60 (t, J=8.7 Hz, 1H), 4.70 (t, J=5.8 Hz, 1H), 3.78 (t, J=4.9 Hz, 2H), 3.47-3.57 (m, 5H), 0.19 (s, 9H)

2-((4-Ethynyl-2-fluorophenyl)amino)-N-(2-hydroxyethoxy)-1-methyl-1H-pyrrolo[2,3-b]pyridine-3-carboxamide

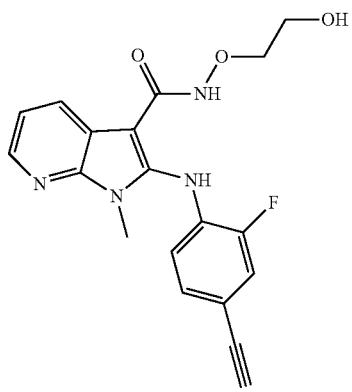 [SMILES: C#Cc1ccc(Nc2c(C(=O)NOCCO)c3cccnc3n2C)c(F)c1]

A solution of 2-((2-fluoro-4-((trimethylsilyl)ethynyl)phenyl)amino)-N-(2-hydroxyethoxy)-1-methyl-1H-pyrrolo[2,3-b]pyridine-3-carboxamide (100 mg, 0.23 mmol, 80% pure by UPLC-MS) in MeOH (2.1 mL) was treated with K$_2$CO$_3$ (35 mg, 0.25 mmol). The mixture was stirred for 18 h at room temperature. The mixture was purified by preparative HPLC to give the product (15 mg, 22%) as a white solid. UPLC-MS (Acidic Method, 2 min): rt 0.93 min, m z 369.1 [M+H]$^+$. $^1$H NMR (400 MHz, DMSO-d$_6$) δ ppm 8.25 (br d, J=3.5 Hz, 1H), 8.14 (d, J=7.8 Hz, 1H), 7.35 (br d, J=11.8 Hz, 1H), 7.21 (dd, J=7.7, 4.8 Hz, 1H), 7.11 (dd, J=8.3, 1.4 Hz, 1H), 6.63 (t, J=8.7 Hz, 1H), 4.09 (s, 1H), 3.78 (t, J=4.7 Hz, 2H), 3.37-3.55 (m, 5H)

Example 4: 2-((2-Fluoro-4-iodophenyl)amino)-N-hydroxy-1-methyl-1H-pyrrolo[2,3-b]pyridine-3-carboxamide Perfluorophenyl 2-((2-fluoro-4-iodophenyl)amino)-1-methyl-1H-pyrrolo[2,3-b]pyridine-3-carboxylate

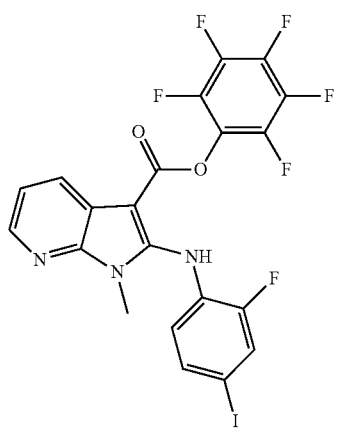 [SMILES: Cn1c(Nc2ccc(I)cc2F)c(C(=O)Oc2c(F)c(F)c(F)c(F)c2F)c2cccnc21]

A solution of 2-((2-fluoro-4-iodophenyl)amino)-1-methyl-1H-pyrrolo[2,3-b]pyridine-3-carbonyl chloride (0.9 g, 2.1 mmol) in dry DCM (50 mL) was cooled to 0° C. in an ice bath and then treated with Et$_3$N (0.8 mL, 5.4 mmol) and pentafluorophenol (0.6 g, 3.2 mmol) and stirred for 1 h.

The mixture was diluted with 1:1 DCM/H$_2$O solution. The organic phase was washed with brine, dried over Na$_2$SO$_4$, and concentrated in vacuo to give the product (1.56 g, quantitative) that was used in the next step without further purification. UPLC-MS (Acidic Method, 2 min): rt 1.43 min, m z 577.8 [M+H]$^+$. $^1$H NMR (400 MHz, DMSO-d$_6$) δ ppm 9.13 (s, 1H), 8.29 (dd, J=4.8, 1.6 Hz, 1H), 8.13-8.17 (m, 1H), 7.59-7.64 (m, 1H), 7.42 (dt, J=8.4, 1.0 Hz, 1H), 7.20-7.31 (m, 1H), 6.95 (t, J=8.7 Hz, 1H), 3.65 (s, 3H).

2-((2-Fluoro-4-iodophenyl)amino)-N-hydroxy-1-methyl-1H-pyrrolo[2,3-b]pyridine-3-carboxamide

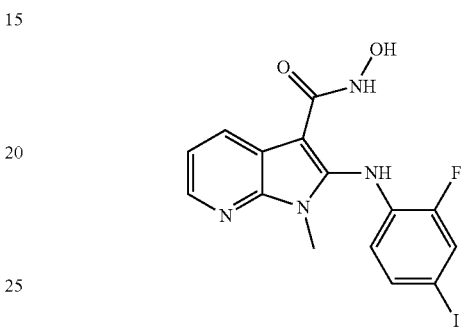

A suspension of perfluorophenyl 2-((2-fluoro-4-iodophenyl)amino)-1-methyl-1H-pyrrolo[2,3-b]-pyridine-3-carboxylate (400 mg, 0.69 mmol, 85% pure by UPLC-MS) in dry DMF (2.4 mL) was treated with hydroxylamine hydrochloride (58 mg, 0.83 mmol) and DIPEA (43 μL, 2.43 mmol). The mixture was stirred for 1 h at room temperature. The mixture was concentrated in vacuo, then the residue was diluted with 1:1 EtOAc/H$_2$O solution. The organic phase was washed with water, brine, dried over Na$_2$SO$_4$, and concentrated in vacuo. The crude was purified by preparative HPLC to give the product (104 mg, 39%) as an off-white solid. UPLC-MS (Acidic Method, 2 min): rt 1.03 min, m z 427.0 [M+H]$^+$. $^1$H NMR (400 MHz, DMSO-d$_6$) δ ppm 10.34 (br s, 1H), 8.83 (br s, 1H), 8.72 (br s, 1H), 8.26 (dd, J=4.8, 1.5 Hz, 1H), 8.18 (dd, J=7.8, 1.6 Hz, 1H), 7.64 (dd, J=10.8, 2.0 Hz, 1H), 7.34 (dt, J=8.4, 0.9 Hz, 1H), 7.21 (dd, J=7.9, 4.8 Hz, 1H), 6.45 (t, J=8.9 Hz, 1H), 3.52 (s, 3H)

Example 5: (R)—N-(2,3-Dihydroxypropoxy)-2-((2-fluoro-4-iodophenyl)amino)-1-methyl-1H-pyrrolo[2,3-b]pyridine-3-carboxamide (R)-2-((2,2-Dimethyl-1,3-dioxolan-4-yl)methoxy)isoindoline-1,3-dione

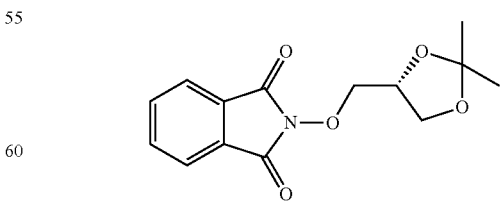

To a suspension of N-hydroxyphthalimide (6.6 g, 40.5 mmol) in THF (135 mL) at 0° C. was added triphenylphosphine (10.6 g, 40.5 mmol) and (S)-(2,2-dimethyl-[1,3]dioxolan-4-yl)-methanol (5 mL, 40.5 mmol). Diisopropyl azodicarboxylate (10.3 mL, 52.7 mmol) was added dropwise whilst keeping the internal temperature below 15° C. Upon completion of the addition, the mixture was warmed to room temperature and stirred under $N_2$ for 2 h. The solvent was removed in vacuo and the residue was diluted with DCM (50 mL). The resulting precipitate was filtered and the filtrate was concentrated in vacuo. The crude was purified by flash column chromatography (Silica 340 g, 10-100% EtOAc in hexane) to give the product (11.1 g, 99%) as a white solid. UPLC-MS (Acidic Method, 2 min): rt 1.06 min, m z 278.1 $[M+H]^+$. $^1$H NMR (400 MHz, $CDCl_3$) δ ppm 7.85-7.82 (m, 2H), 7.76-7.75 (m, 2H), 4.52-4.46 (m, 1H), 4.31 (dd, J=10.0, 5.5 Hz, 1H), 4.17 (dd, J=8.5, 6.0 Hz, 1H), 4.13 (dd, J=10.0, 6.0 Hz, 1H), 3.96 (dd, J=8.5, 5.5 Hz, 1H), 1.39 (s, 3H), 1.33 (s, 3H)

(R)—O-((2,2-Dimethyl-1,3-dioxolan-4-yl)methyl) hydroxylamine

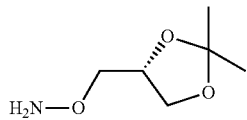

To a suspension of (R)-2-((2,2-dimethyl-1,3-dioxolan-4-yl)methoxy)isoindoline-1,3-dione (3.0 g, 10.8 mmol) in DCM (22 mL) at 0° C. was added methyl hydrazine (0.62 mL, 11.9 mmol) dropwise. The resultant mixture was warmed to room temperature and stirred under $N_2$ for 1 h. The solvent was removed in vacuo and the residue was diluted with diethyl ether (20 mL). The mixture was stirred for 0.5 h before filtering and washing with diethyl ether (2×20 mL). The filtrate was concentrated to dryness in vacuo to give the product (0.85 g, 46%) as a pale-yellow oil. $^1$H NMR (400 MHz, $CDCl_3$) δ ppm 5.00-4.94 (m, 1H), 4.38-4.32 (m, 1H), 4.06 (dd, J=8.5, 6.5 Hz, 1H), 3.74 (dd, J=6.0, 5.0 Hz, 1H), 3.69 (dd, J=8.5, 6.5 Hz, 1H), 1.43 (s, 3H), 1.37 (s, 3H).

(R)—N-((2,2-Dimethyl-1,3-dioxolan-4-yl)methoxy)-2-((2-fluoro-4-iodophenyl)amino)-1-methyl-1H-pyrrolo[2,3-b]pyridine-3-carboxamide

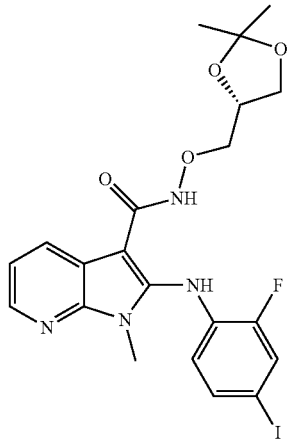 [SMILES: Cn1c(Nc2ccc(I)cc2F)c(C(=O)NOC[C@H]2COC(C)(C)O2)c2cccnc21]

To a solution of perfluorophenyl 2-((2-fluoro-4-iodophenyl)amino)-1-methyl-1H-pyrrolo[2,3-b]pyridine-3-carboxylate, prepared as described in Example 4, (390 mg, 0.676 mmol) in DMF (2 mL) was added a solution of (R)—O-((2,2-dimethyl-1,3-dioxolan-4-yl)methyl)hydroxylamine (149 mg, 1.010 mmol) in DMF (0.5 mL) and DIPEA (24 μL, 1.350 mmol). The resultant mixture was stirred at room temperature under $N_2$ for 18 h. The reaction mixture was diluted with ice-cold $H_2O$ (50 mL) and then extracted with EtOAc (2×25 mL). The combined organic phases were washed with brine (2×100 mL), dried over $Na_2SO_4$, and concentrated in vacuo to give the product (300 mg, 82%) as a dark red solid that was used in the next step without further purification. UPLC-MS (Acidic Method, 2 min): rt 1.15 min, m z 541.1 $[M+H]^+$. $^1$H NMR (400 MHz, $CDCl_3$) δ ppm 8.82 (s, 1H), 8.75 (s, 1H), 8.26 (dd, J=5.0, 1.5 Hz, 1H), 7.87 (d, J=7.5 Hz, 1H), 7.50 (dd, J=10.0, 1.5 Hz, 1H), 7.40-7.37 (m, 1H), 7.20 (dd, J=7.5, 5.0 Hz, 1H), 6.66 (app t, J=8.5 Hz, 1H), 5.00-4.95 (m, 1H), 4.51-4.45 (m, 1H), 4.18-4.05 (m, 2H), 3.85 (dd, J=9.0, 6.5 Hz, 1H), 3.52 (s, 3H), 1.46 (s, 3H), 1.40 (s, 3H)

Example 6: (R)—N-(2,3-Dihydroxypropoxy)-2-((2-fluoro-4-iodophenyl)amino)-1-methyl-1H-pyrrolo[2,3-b]pyridine-3-carboxamide

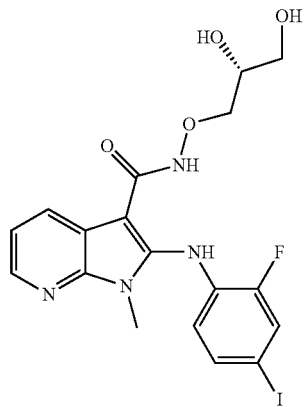 [SMILES: Cn1c(Nc2ccc(I)cc2F)c(C(=O)NOC[C@H](O)CO)c2cccnc21]

To a solution of (R)—N-((2,2-dimethyl-1,3-dioxolan-4-yl)methoxy)-2-((2-fluoro-4-iodophenyl)amino)-1-methyl-1H-pyrrolo[2,3-b]pyridine-3-carboxamide (220 mg, 0.40 mmol) in MeOH (5 mL) was added p-toluene sulfonic acid monohydrate (39 mg, 0.20 mmol) and ethylene glycol (13 μL, 2.40 mmol). The resultant mixture was stirred at room temperature under $N_2$ for 0.5 h. A few drops of $Et_3N$ were added to the reaction mixture and the solvent was removed in vacuo. The crude product was purified by preparatory HPLC to give the product (47 mg, 24%) as an off-white solid. UPLC-MS (Acidic Method, 2 min): rt 0.96 min, m z 501.0 $[M+H]^+$. $^1$H NMR (400 MHz, DMSO-$d_6$) δ ppm 10.89 (s, 1H), 8.71 (s, 1H), 8.27 (dd, J=5.0, 1.5 Hz, 1H), 8.16 (dd, J=7.5, 1.5 Hz, 1H), 7.64 (dd, J=10.5, 1.5 Hz, 1H), 7.37-7.35 (m, 1H), 7.23 (dd, J=7.5, 5.0 Hz, 1H), 6.55 (app t, J=8.5 Hz, 1H), 4.93 (s, 1H), 4.60 (s, 1H), 3.87-3.82 (m, 1H), 3.72-3.66 (m, 2H), 3.54 (s, 3H), 3.39-3.35 (m, 2H).

Example 7: N-(Cyclopropylmethoxy)-2-((2-fluoro-4-iodophenyl)amino)-1-methyl-1H-pyrrolo[2,3-b]pyridine-3-carboxamide

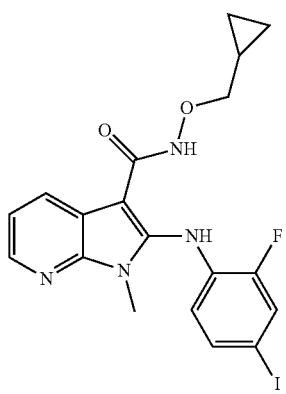 [SMILES: Cn1c(Nc2ccc(I)cc2F)c(C(=O)NOCC2CC2)c2cccnc21]

To a solution of perfluorophenyl 2-((2-fluoro-4-iodophenyl)amino)-1-methyl-1H-pyrrolo[2,3-b]pyridine-3-carboxylate, prepared as described in Example 4, (400 mg, 0.69 mmol) in DMF (2.5 mL) was added a solution of O-(cyclopropylmethyl)hydroxylamine hydrochloride (100 mg, 0.83 mmol) in DMF (0.5 mL) and DIPEA (24 µL, 1.35 mmol). The resultant mixture was stirred at room temperature under $N_2$ for 18 h. The reaction mixture was diluted with ice-cold $H_2O$ (50 mL) and then extracted with EtOAc (2×25 mL). The combined organic phases were washed with brine (2×100 mL), dried over $Na_2SO_4$, and concentrated in vacuo. The crude product was purified by preparative HPLC (Reach Separations, UK) to give the product (135 mg, 36%) as a white solid. UPLC-MS (Acidic Method, 4 min): rt 1.95 min, m z 481.0 [M+H]$^+$. $^1$H NMR (400 MHz, CDCl$_3$) δ ppm 11.42 (s, 1H), 10.75 (s, 1H), 8.67 (s, 1H), 8.25 (dd, J=5.0, 1.5 Hz, 1H), 8.14 (dd, J=8.0, 1.5 Hz, 1H), 7.63 (dd, J=10.5, 2.0 Hz, 1H), 7.36-7.33 (m, 1H), 7.22 (dd, J=7.5, 5.0 Hz, 1H), 3.56 (d, J=7.0 Hz, 1H), 3.55 (s, 3H), 1.04-0.97 (m, 1H), 0.50-0.45 (m, 2H), 0.22-0.18 (m, 2H).

Example 8: 2-((2-Fluoro-4-iodophenyl)amino)-N-(2-hydroxyethoxy)-5-methoxy-1-methyl-1H-pyrrolo[2,3-b]pyridine-3-carboxamide 5-Methoxy-1-methyl-1H-pyrrolo[2,3-b]pyridine

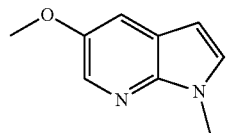

A solution of 5-methoxy-7-azaindole (5.0 g, 33.7 mmol) in dry DMF (25 mL) was cooled to 0° C. in an ice bath and treated with sodium hydride (1.6 g, 40.5 mmol, 60% in mineral oil) in a portion-wise manner. The resulting mixture was stirred for 1 h at 0° C., then treated with iodomethane (2.3 mL, 37.1 mmol) and was stirred at 0° C. for 1 h. The mixture was then cautiously poured into H$_2$O (200 mL) and extracted with EtOAc (3×30 mL). The combined organic phases were washed sequentially with water (3×30 mL) and brine, dried over Na$_2$SO$_4$, filtered, and concentrated under vacuum to give the product (5.8 g, quantitative) as a light-brown solid. UPLC-MS (Acidic Method, 4 min): rt 0.91 min, m z 161.1 [M+H]$^+$. $^1$H NMR (400 MHz, CDCl$_3$) δ ppm 8.12 (d, J=2.6 Hz, 1H), 7.42 (d, J=2.8 Hz, 1H), 7.27 (s, 1H), 7.16 (d, J=3.4 Hz, 1H), 6.37 (d, J=3.4 Hz, 1H), 3.88 (s, 3H), 3.87 (s, 3H).

5-Methoxy-1-methyl-1H-pyrrolo[2,3-b]pyridine-3-carboxylic Acid

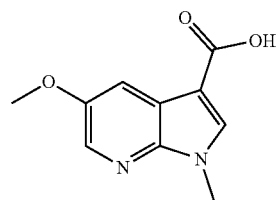

A solution of 5-methoxy-1-methyl-1H-pyrrolo[2,3-b]pyridine (5.5 g, 46.5 mmol) in dry DMF (7 mL) was cooled to 0° C. in an ice bath and treated with trifluoroacetic anhydride (10.6 g, 50.7 mmol). The reaction mixture was then gradually warmed up to room temperature and left stirring for 1 h. The resulting mixture was cooled to 0° C. in an ice bath and treated with water (200 mL) and extracted with DCM (3×30 mL). The combined organic phases were dried over Na$_2$SO$_4$, filtered, and concentrated under vacuum. The residue was suspended in 5M NaOH aqueous solution (68 mL) and heated at 50° C. for 18 h. The reaction mixture was washed with Et$_2$O (1×30 mL) and cautiously treated with 1M HCl aqueous solution until pH=1 leading to a formation of a beige precipitate. The solid was collected by filtration, washed with H$_2$O until the filtrate became pH neutral, and dried to give the product (5.9 g, 85%) as a beige solid. UPLC-MS (Acidic Method, 2 min): rt 0.80 min, m/z 207.1 [M+H]$^+$. $^1$H NMR (400 MHz, DMSO-d$_6$) δ ppm 8.18 (s, 1H), 8.10 (d, J=2.9 Hz, 1H), 7.81 (d, J=2.9 Hz, 1H), 3.86 (s, 3H), 3.84 (s, 3H).

tert-Butyl 5-methoxy-1-methyl-1H-pyrrolo[2,3-b]pyridine-3-carboxylate

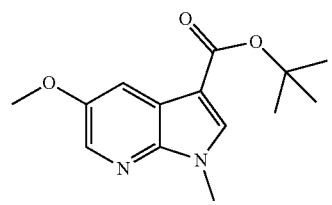 [SMILES: COc1cnc2c(c1)c(C(=O)OC(C)(C)C)cn2C]

To a suspension of 5-methoxy-1-methyl-1H-pyrrolo[2,3-b]pyridine-3-carboxylic acid (5.9 g, 28.6 mmol) in anhydrous DCM (200 mL) cooled on ice, oxalyl chloride (7.3 mL, 85.8 mmol) was added dropwise over 15 min and the mixture was stirred at room temperature for 1.5 h. The mixture was then concentrated under vacuum to give a yellow solid, which was cooled on ice, then treated with tert-butanol (150 mL, 1.6 mol), followed by an addition of potassium tert-butoxide (5.1 g, 45.8 mmol). The resulting mixture was gradually warmed up to room temperature and left stirring for 18 h. The reaction mixture was concentrated under vacuum, distributed between EtOAc (50 mL) and H$_2$O (50 mL) and extracted with EtOAc (3×50 mL). The combined organic phases were dried over Na$_2$SO$_4$, filtered, and concentrated under vacuum. The crude material was purified by flash column chromatography (Silica 120 g, 0-3% MeOH in DCM) to give the product (3.9 g, 53%) as a yellow solid. UPLC-MS (Acidic Method, 2 min): rt 1.15 min, m z 263.2 [M+H]$^+$. $^1$H NMR (400 MHz, DMSO-d$_6$) δ ppm 8.08-8.14 (m, 2H), 7.76-7.81 (m, 1H), 3.86 (s, 3H), 3.83 (s, 3H), 1.57 (s, 9H)

tert-Butyl 2-chloro-5-methoxy-1-methyl-1H-pyrrolo[2,3-b]pyridine-3-carboxylate

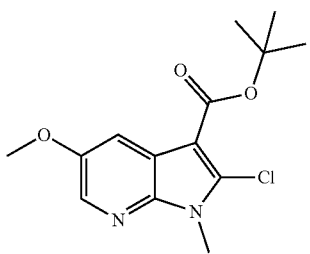 [SMILES: COc1cnc2c(c1)c(C(=O)OC(C)(C)C)c(Cl)n2C]

A solution of tert-butyl 5-methoxy-1-methyl-1H-pyrrolo[2,3-b]pyridine-3-carboxylate (2.2 g, 8.6 mmol) in dry THF (36 mL) was flushed with N$_2$, cooled to −78° C. and then treated with a solution of LDA (2M in THF, 8.55 mL, 17.1 mmol). The mixture was stirred at −78° C. for 30 min. A solution of hexachloroethane (4.1 g, 17.1 mmol) in dry THF (12 mL) was added and the mixture was gradually warmed up to a room temperature and stirred for 2 h. The mixture was treated with saturated NH$_4$Cl aqueous solution and extracted with EtOAc (3×30 mL). The combined organic phases were dried over Na$_2$SO$_4$, filtered and concentrated under vacuum. The crude was purified by flash column chromatography (Silica 120 g, 0-10% EtOAc in hexanes) to give the product (2.4 g, 95%) as a beige solid. UPLC-MS (Acidic Method, 2 min): rt 1.27 min, m z 297.1/299.0 [M+H]*. $^1$H NMR (400 MHz, DMSO-d$_6$) δ ppm 8.12 (br d, J=2.6 Hz, 1H), 7.78 (br d, J=2.5 Hz, 1H), 3.86 (s, 3H), 3.79 (s, 3H), 1.59 (s, 9H)

tert-Butyl 2-((2-fluoro-4-iodophenyl)amino)-5-methoxy-1-methyl-1H-pyrrolo[2,3-b]pyridine-3-carboxylate

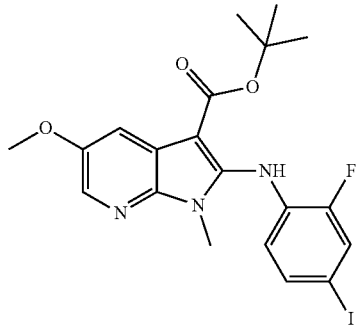 [SMILES: COc1cnc2c(c1)c(C(=O)OC(C)(C)C)c(Nc1ccc(I)cc1F)n2C]

A suspension of tert-butyl 2-chloro-5-methoxy-1-methyl-1H-pyrrolo[2,3-b]pyridine-3-carboxylate (2.4 g, 8.1 mmol) and 2-fluoro-4-iodoaniline (1.8 g, 7.7 mmol) in dry THF (44 mL) was flushed with N$_2$, cooled to −78° C. and treated with a solution of LiHMDS (1M in THF, 16.2 mL, 16.2 mmol). The mixture was gradually warmed up to room temperature and stirred for 1.5 h. The mixture was quenched with saturated NH$_4$Cl aqueous solution and then extracted with EtOAc (3×25 mL). The combined organic phases were dried over Na$_2$SO$_4$, filtered, and concentrated under vacuum. The crude material was purified by flash column chromatography (Silica 120 g, 0-10% EtOAc in hexanes) to give the product (3.5 g, 91%) as a pale yellow solid. UPLC-MS (Acidic Method, 4 min): rt 2.59 min, m z 498.0 [M+H]. $^1$H NMR (400 MHz, DMSO-d$_6$) δ ppm 8.56 (s, 1H), 7.98-8.03 (m, 1H), 7.74 (d, J=2.8 Hz, 1H), 7.64 (dd, J=10.8, 1.9 Hz, 1H), 7.37 (d, J=8.5 Hz, 1H), 6.65 (t, J=8.8 Hz, 1H), 3.86 (s, 3H), 3.56 (s, 3H), 1.41 (s, 9H)

2-((2-Fluoro-4-iodophenyl)amino)-5-methoxy-1-methyl-1H-pyrrolo[2,3-b]pyridine-3-carbonyl Chloride

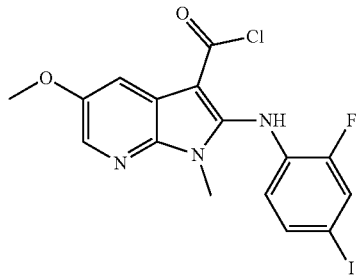 [SMILES: COc1cnc2c(c1)c(C(=O)Cl)c(Nc1ccc(I)cc1F)n2C]

Thionyl chloride (5.1 mL, 69.8 mmol) was added to tert-butyl 2-((2-fluoro-4-iodophenyl)amino)-5-ethoxy-1-methyl-1H-pyrrolo[2,3-b]pyridine-3-carboxylate (3.5 g, 7.0 mmol) followed by H$_2$O (130 μL, 7.0 mmol). The flask was sealed with a rubber septum and the mixture was stirred at room temperature for 1.5 h. The mixture was concentrated to dryness under vacuum to give the product (3.6 g, 55%) as a beige solid and was used in the next step without further purification. UPLC-MS (Acidic Method, 2 min): rt 1.31 min, m z 456.0 [M+H]$^+$ (detected as the corresponding methyl ester after quenching an aliquot of the mixture with MeOH).

2-((2-Fluoro-4-iodophenyl)amino)-N-(2-hydroxyethoxy)-5-methoxy-1-methyl-1H-pyrrolo[2,3-b]pyridine-3-carboxamide

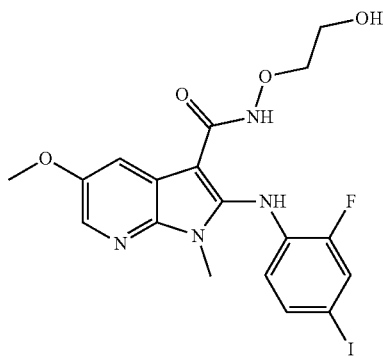 [SMILES: COc1cnc2c(c1)c(C(=O)NOCCO)c(Nc1ccc(I)cc1F)n2C]

A solution of 2-((2-fluoro-4-iodophenyl)amino)-5-methoxy-1-methyl-1H-pyrrolo[2,3-b]pyridine-3-carbonyl chloride (1.0 g, 2.2 mmol) in dry DCM (57 mL) was cooled to 0° C. in an ice bath and then treated with dry pyridine (2 mL, 24.4 mmol) and the mixture was stirred for 5 min followed by an addition of (2-aminooxy)ethanol (0.4 g, 5.4 mmol) in dry DCM (5 mL). The mixture was stirred for 15 min, then concentrated under vacuum. The crude material was purified by preparative HPLC to give the product (85 mg, 13%) as a beige-yellow solid. UPLC-MS (Acidic Method, 2 min): rt 1.07 min, m z 501.0 [M+H]$^+$. $^1$H NMR (400 MHz, DMSO-d$_6$) δ ppm 10.79 (s, 1H), 8.70 (br s, 1H), 8.02 (d, J=2.6 Hz, 1H), 7.75 (d, J=2.6 Hz, 1H), 7.64 (dd, J=10.9, 1.8 Hz, 1H), 7.35 (d, J=8.6 Hz, 1H), 6.52 (t, J=8.8 Hz, 1H), 4.75 (br t, J=5.8 Hz, 1H), 3.80-3.89 (m, 5H), 3.48-3.56 (m, 5H).

Example 9: (S)—N-((2,2-dimethyl-1,3-dioxolan-4-yl)methyl)-2-((2-fluoro-4-iodophenyl)amino)-1-methyl-1H-pyrrolo[2,3-b]pyridine-3-carboxamide

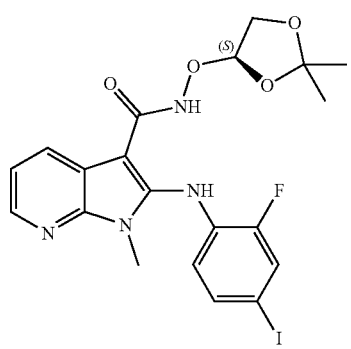

A solution of 2-((2-fluoro-4-iodophenyl)amino)-1-methyl-1H-pyrrolo[2,3-b]pyridine-3-carbonyl chloride (See Example 2, 937 mg, 2.18 mmol) in dry THF (4 mL) under N$_2$ was cooled in an ice-water bath while stirring. The reaction mixture was treated with a solution of (S)-(+)-(2,2-dimethyl-1,3-dioxolan-4-yl)methanamine (256 mg, 1.95 mmol) and diisopropylethylamine (0.33 mL, 1.95 mmol) in dry THF (5 mL) and stirred for 18 h. Reaction mixture was concentrated in vacuo and the crude residue was purified by flash column chromatography (Silica 40 g, 20-80% EtOAc in hexane) to give the product (512 mg, 44.4%) as an off-white solid which was used in subsequent steps without further purification. UPLC-MS (Acidic Method, 2 min): rt 1.10 min, m z 525.0 [M+H]$^+$. $^1$H NMR (400 MHz, DMSO-d$_6$) δ ppm 8.84 (s, 1H), 8.34 (dd, J=7.9, 1.6 Hz, 1H), 8.29 (dd, J=4.8, 1.6 Hz, 1H), 7.65 (dd, J=10.7, 1.9 Hz, 1H), 7.59 (s, 1H), 7.32-7.36 (m, 1H), 7.24 (dd, J=7.8, 4.8 Hz, 1H), 6.44 (t, J=8.8 Hz, 1H), 4.05-4.10 (m, 1H), 3.86 (dd, J=8.3, 6.27 Hz, 1H), 3.56-3.62 (m, 1H), 3.54 (s, 3H), 3.36 (td, J=5.8, 2.0 Hz, 2H), 1.26 (s, 3H), 1.22 (s, 3H).

Example 10: (S)—N-(2,3-dihydroxypropyl)-2-((2-fluoro-4-iodophenyl)amino)-1-methyl-1H-pyrrolo[2,3-b]pyridine-3-carboxamide

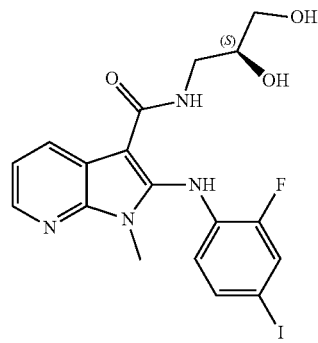

A solution of (S)—N-((2,2-dimethyl-1,3-dioxolan-4-yl)methyl)-2-((2-fluoro-4-iodophenyl)-amino)-1-methyl-1H-pyrrolo[2,3-b]pyridine-3-carboxamide (512 mg, 0.97 mmol) in 1,4-dioxane (5.1 mL) was treated with 4 N HCl in 1,4-dioxane (0.61 mL, 2.42 mmol) and stirred at room temperature for 72 h. The reaction mixture was concentrated, the residue was re-suspended in 1,4-dioxane (5.1 mL) with addition of 4 N HCl in 1,4-dioxane (0.61 mL, 2.42 mmol) and stirred for 16 h until completion. The reaction mixture was concentrated and the crude residue was purified by preparatory HPLC to give the product (172 mg, 36.6%) as a flocculant white solid. UPLC-MS (Acidic Method, 2 min): rt 0.89 min, m z 485.0 [M+H]$^+$. $^1$H NMR (400 MHz, DMSO-d$_6$) δ ppm 8.89 (s, 1H), 8.33 (dd, J=7.9, 1.5 Hz, 1H), 8.29 (dd, J=4.8, 1.5 Hz, 1H), 7.65 (dd, J=10.7, 1.9 Hz, 1H), 7.52 (t, J=5.5 Hz, 1H), 7.35 (d, J=8.6 Hz, 1H), 7.24 (dd, J=7.9, 4.8 Hz, 1H), 6.46 (t, J=8.8 Hz, 1H), 4.79 (d, J=4.8 Hz, 1H), 4.57 (t, J=5.8 Hz, 1H), 3.52 (m, 4H), 3.39 (m, 1H), 3.15-3.31 (m, 3H).

Example 11: ((R)—N-((2,2-dimethyl-1,3-dioxolan-4-yl)methyl)-2-((2-fluoro-4-iodophenyl)amino)-1-methyl-1H-pyrrolo[2,3-b]pyridine-3-carboxamide

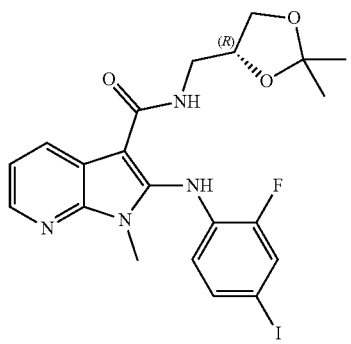

A solution of 2-((2-fluoro-4-iodophenyl)amino)-1-methyl-1H-pyrrolo[2,3-b]pyridine-3-carbonyl chloride (See Example 2, 937 mg, 2.18 mmol) in dry THF (4 mL) under N$_2$ was cooled in an ice-water bath while stirring. The reaction mixture was treated with a solution of (R)-(−)-(2,2-dimethyl-1,3-dioxolan-4-yl)methanamine (256 mg, 1.95 mmol) and diisopropylethylamine (0.33 mL, 1.95 mmol) in dry THF (5 mL) and stirred for 18 h. Reaction mixture was concentrated in vacuo and the crude residue was purified by flash column chromatography (Silica 40 g, 20-80% EtOAc in hexane) to give the product (442 mg, 38.5%) as an off-white solid which was used in subsequent steps without further purification. UPLC-MS (Acidic Method, 2 min): rt 1.10 min, m z 525.0 [M+H]+. 1H NMR (400 MHz, DMSO-d6) δ ppm 8.83 (s, 1H), 8.32-8.36 (m, 1H), 8.27-8.32 (m, 1H), 7.62-7.68 (m, 1H), 7.55-7.62 (m, 1H), 7.31-7.37 (m, 1H), 7.21-7.27 (m, 1H), 6.40-6.47 (m, 1H), 4.05-4.09 (m, 1H), 3.84-3.89 (m, 1H), 3.57-3.62 (m, 1H), 3.54 (s, 3H), 3.37-3.38 (m, 2H), 1.26 (s, 3H), 1.22 (s, 3H).

Example 12: (R)—N-(2,3-dihydroxypropyl)-2-((2-fluoro-4-iodophenyl)amino)-1-methyl-1H-pyrrolo[2,3-b]pyridine-3-carboxamide

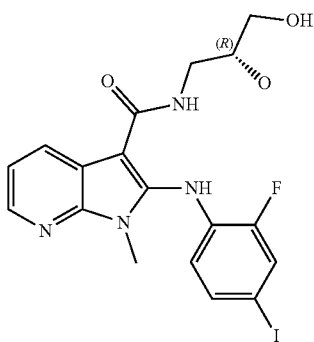

A solution of (R)—N-((2,2-dimethyl-1,3-dioxolan-4-yl)methyl)-2-((2-fluoro-4-iodophenyl)-amino)-1-methyl-1H-pyrrolo[2,3-b]pyridine-3-carboxamide (442 mg, 0.84 mmol) in 1,4-dioxane (4.4 mL) was treated with 4 N HCl in 1,4-dioxane (0.52 mL, 2.1 mmol) and stirred at room temperature for 72 h. The reaction mixture was concentrated, the residue was re-suspended in 1,4-dioxane (4.4 mL) with addition of 4 N HCl in 1,4-dioxane (0.52 mL, 2.1 mmol) and stirred for 16 h until completion. The reaction mixture was concentrated and the crude residue was purified by preparatory HPLC to give the product (156 mg, 38%) as a flocculant white solid. UPLC-MS (Acidic Method, 2 min): rt 0.89 min, m z 485.0 [M+H]+. 1H NMR: (400 MHz, DMSO-d6) δ ppm 8.89 (s, 1H), 8.33 (dd, J=7.9, 1.5 Hz, 1H), 8.29 (dd, J=4.8, 1.5 Hz, 1H), 7.64 (dd, J=10.8, 1.9 Hz, 1H), 7.48-7.56 (m, 1H), 7.35 (dd, J=8.5, 1.1 Hz, 1H), 7.24 (dd, J=7.8, 4.8 Hz, 1H), 6.46 (t, J=8.8 Hz, 1H), 4.79 (d, J=4.8 Hz, 1H), 4.57 (t, J=5.8 Hz, 1H), 3.50-3.57 (m, 4H), 3.41 (dt, J=13.2, 5.6 Hz, 1H), 3.14-3.31 (m, 3H).

Example 13: 2-(2-Fluoro-4-iodoanilino)-1-methyl-1H-pyrrolo[2,3-b]pyridine-3-carboxamide

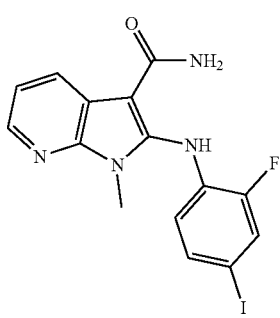 [SMILES: Cn1c(Nc2ccc(I)cc2F)c(C(N)=O)c2cccnc21]

A suspension of 2-((2-fluoro-4-iodophenyl)amino)-1-methyl-1H-pyrrolo[2,3-b]pyridine-3-carbonyl chloride (0.50 g, 1.16 mmol) in 1,4-dioxane (2.3 mL) was stirred under N2 on an ice/water bath and 0.5 M NH3 in 1,4-dioxane (2.7 mL, 1.33 mmol) was added dropwise over 5 min. An additional portion of 1,4-dioxane (2.3 mL) was added and the reaction mixture was stirred for the next 18 h while warming up to room temperature. Then the reaction mixture was concentrated to dryness in vacuo and the crude was purified by flash column chromatography (Silica 20 g, 20-100% EtOAC in hexane) to give the product (39.1 mg, 9%) as an off-white solid.

UPLC-MS (Acidic Method, 2 min): rt 0.97 min, m z 411.0 [M+H]+ 1H NMR (400 MHz, DMSO-d6) δ ppm 9.07 (s, 1H), 8.34 (dd, J=7.9, 1.5 Hz, 1H), 8.27 (dd, J=4.8, 1.5 Hz, 1H), 7.67 (dd, J=10.7, 1.9 Hz, 1H), 7.38 (dd, J=8.4, 1.1 Hz, 1H), 7.22 (dd, J=7.9, 4.8 Hz, 1H), 7.13 (br s, 2H), 6.52 (t, J=8.8 Hz, 1H), 3.50 (s, 3H)

Biological Example 1a

MEK Inhibition Assay

MEK1 inhibitory activity of compounds were tested using the following procedure. (See Anastassiadis T, et al. *Comprehensive assay of kinase catalytic activity reveals features of kinase inhibitor selectivity. Nat Biotechnol.* 2011, 29(11), 1039-45.) Reagents:

Reaction buffer: 20 mM Hepes (pH 7.5), 10 mM MgCl2, 1 mM EGTA, 0.02% Brij35, 0.02 mg/mL bovine serum albumin, 0.1 mM Na3VO4, 2 mM DTT, 1% DMSO Enzyme: MEK1, Invitrogen cat #PV3303

N-terminal His-tagged recombinant human full length protein, expressed in insect cells. Activated in vitro by RAFI. MW=49.2 kDa, GenBank Accession No. NP_002746.

Substrate: 5 μM ERK2 (K52R),

Kinase-dead mutant, (GenBank Accession No. NM_0011949), aa2-358 with N-terminal His6 tag, MW=43.63 kDa, expressed in *E. coli*.

The substrate was prepared in freshly prepared Reaction Buffer. The kinase was delivered into the substrate solution and gently mixed. Test compounds were delivered in 100% DMSO into the kinase reaction mixture by Acoustic technology (Echo550; nanoliter range), and incubated for 20 min at room temperature. 33P-ATP was delivered into the reaction mixture to initiate the reaction. The reaction mixture was incubated for 2 hours at room temperature. Kinase activity was detected by P81 filter-binding method.

Biological Example 1b

MEK Inhibition Assay

MEK1 inhibitory activity of compounds were tested using the following procedure (protocol available at thermofisher.com/content/dam/LifeTech/migration/files/drug-discovery/pdfs.par.60256.file.dat/20130430%20ssbk%20customer%20protocol%20and%20assay%20conditions.pdf). The Z'-LYTE biochemical assay (ThermoFisher) employs a fluorescence-based, coupled-enzyme format and is based on the differential sensitivity of phosphorylated and non-phosphorylated peptides to proteolytic cleavage.

Test compounds in 100% DMSO were screened in 1% DMSO (final) in the well. For 10 point titrations, 3-fold serial dilutions are conducted from the starting concentration of 30 μM.

The peptide/kinase, MAP2K1 (MEK1)/inactive MAPK1 (ERK2)/Ser/Thr 03, mixture ("Peptide/kinase Mixture") was diluted to a 2× working concentration in the following buffer ("Kinase Buffer"): 50 mM HEPES pH 7.5, 0.01% BRIJ-35, 10 mM MgCl2, 1 mM EGTA. The final 10 µL kinase reaction consisted of 0.06-0.25 ng MAP2K1 (MEK1), 105 ng inactive MAPK1 (ERK2), and 2 µM Ser/Thr 03 in 50 mM HEPES pH 7.5, 0.01% BRIJ-35, 10 mM MgCl$_2$, 1 mM EGTA. After the 1 hour incubation, 5 µL of a 1:1024 dilution of Development Reagent A (available from Invitrogen, catalog no. PV3295) was added.

ATP solutions were diluted to a 4× working concentration in Kinase Buffer (50 mM HEPES pH 7.5, 0.01% BRIJ-35, 10 mM MgCl2, 1 mM EGTA). ATP Km apparent was previously determined using a Z'-LYTE assay. The Development Reagent was diluted in Development Buffer (available from Invitrogen, catalog no. P3127).

Assay Protocol: 2.5 µL of 4× test compound or 100 µL of 100× Test Compound plus 2.4 µL Kinase Buffer, 5 µL of the 2× Peptide/Kinase Mixture, 2.5 µL of 4×ATP Solution were added to the plates and placed on a shake plate for 30-seconds. The kinase reaction was allowed to proceed for 60-minute at room temperature, before 5 µL of Development Reagent Solution was added, and the mixture agitated for 30-seconds on a shake plate. The mixture was incubated for 60-minute at room temperature. Fluorescence was measured using a plate reader and the data were analyzed.

The maximum emission ratio was established by the 0% Phosphorylation Control (100% Inhibition Control), which contained no ATP and therefore exhibited no kinase activity. This control yielded 100% cleaved peptide in the Development Reaction. The 100% Phosphorylation Control, which consisted of a synthetically phosphorylated peptide of the same sequence as the peptide substrate, was designed to allow for the calculation of percent phosphorylation. This control yielded a very low percentage of cleaved peptide in the Development Reaction. The 0% Phosphorylation and 100% Phosphorylation Controls allow for the calculation of the percent phosphorylation achieved in a specific reaction well. Control wells did not include any kinase inhibitors.

The minimum emission ratio in a screen was established by the 0% Inhibition Control, which contained active kinase. This control was designed to produce a 10-50% phosphorylated peptide in the Kinase Reaction. Cascade assays may produce up to 70% phosphorylated peptide.

A known inhibitor control standard curve, 10 point titration, was run for each individual kinase on the same plate as the kinase to ensure the kinase was inhibited within an expected IC$_{50}$ range previously determined.

The following controls are prepared for each concentration of Test Compound assayed. The Development Reaction Interference was established by comparing the Test Compound Control wells that did not contain ATP versus the 0% Phosphorylation Control (which did not contain the Test Compound). The expected value for a non-interfering compound should be 100%. Any value outside of 90% to 110% was flagged. The Test Compound Fluorescence Interference was determined by comparing the Test Compound Control wells that did not contain the Kinase/Peptide Mixture (zero peptide control) versus the 0% Inhibition Control. The expected value for a non-fluorescence compound should be 0%. Any value >20% was flagged.

The data in Table A was calculated. XLfit from IDBS was used. The dose response curve was curve fit to model number 205 (sigmoidal dose-response model). If the bottom of the curve did not fit between −20% & 20% inhibition, it was set to 0% inhibition. If the top of the curve did not fit between 70% and 130% inhibition, it was set to 100% inhibition.

TABLE A

| | Equation |
|---|---|
| Correction for Background Fluorescence | $FI_{Sample} - FI_{TCFI\ Ctrl}$ |
| Emission Ratio (using values corrected for background fluorescence) | $\dfrac{\text{Coumarin Emission}(445\ nm)}{\text{Fluorescein Emission}(520\ nm)}$ |
| % Phosphorylation (% Phos) | $\left\{1 - \dfrac{(\text{Emission Ration} \times F_{100\%}) - C_{100\%}}{(C_{0\%} - C_{100\%}) + [\text{Emission Ration} \times F_{100\%} - F_{0\%})]}\right\} * 100$ |
| % Inhibition | $\left\{1 - \dfrac{\%\ Phos_{Sample}}{\%\ Phos_{0\%\ Inhibition\ Ctrl}}\right\} * 100$ |
| Z' (using Emission Ratio values) | $1 - \dfrac{3 * Stdev_{0\%\ Pho\ Ctrl} + 3 + Stdev_{0\%\ Inhibition}}{\text{Mean}_{0\%\ Pho\ Ctrl} - \text{Mean}_{0\%\ Inhibition}}$ |
| Difference Between Data Points (single point only) | $\lvert \%\ \text{Inhibition}_{Point\ 1} - \%\ \text{Inhibition}_{Point\ 2} \rvert$ |
| Development Reaction Interference (DRI) (no ATP control) | $\dfrac{\text{Emission Ratio}_{DRI\ Ctrl}}{\text{Emission Ratio}_{0\%\ Phos\ Ctrl}}$ |

TABLE A-continued

| | Equation |
|---|---|
| Test Compound Fluorescence Interference (TCFI) (check both Coumarin and Fluorescein emissions) | $\dfrac{FI_{TCFI\ Ctrl}}{FI_{0\%\ Inhibition\ Ctrl}}$ |

FI = Fluorescence Intensity
$C_{100\%}$ = Average Coumarin emission signal of the 100% Phos. Control
$C_{0\%}$ = Average Coumarin emission signal of the 0% Phos. Control
$F_{100\%}$ = Average Fluorescein emission signal of the 100% Phos. Control
$F_{0\%}$ = Average Fluorescein emission signal of the 0% Phos. Control
DRI = Development Reaction Interference
TCFI = Test Compound Fluorescence Interference Biological Example 2a Cell-Based Assay Preparation of cell lines useful for testing the soft MEK inhibitors in NF1 related cell-proliferation assays can be found in Basu et al. Nature 356: 713-715, 1992; and DeClue et al. Cell 69: 265-273, 1992. In addition, exemplary in vitro and in vivo models to determine efficacy of the soft MEK inhibitors described herein can be found in U.S. Pat. Nos. 8,211,875 and 8,487,004, which are incorporated by reference in their entireties.

Biological Example 2b

Cell-Based Assay

Alternatively, the following procedure can be used to measure cell-based activity. Test compounds were dissolved in DMSO in 10 mM stock. Cell Titer-Glo® 2.0 Luminescent cell viability assay reagent was purchased from Promega (Madison, WI). A375 and HCT116 cell lines were purchased from American Type Culture Collection (Manassas, VA). For A375 cells, cell culture media was DMEM+10% FBS. Cell culture media are listed in the following table. For HCT116 cells, cell culture media was McCoy's 5A+10% FBS. All media were supplemented with 100 μg/mL of penicillin, and 100 μg/mL of streptomycin. Cultures were maintained at 37° C. in a humidified atmosphere of 5% $CO_2$ and 95% air.

Test compounds were diluted in DMSO solution with 10-dose and 3-fold dilutions in a source plate starting at 10 mM. 25 nL of each test compound was delivered from the source plate to each well of the 384-well cell culture plates (T=Final) by Echo 550. 25 μL of culture medium containing 2000 of A375 or HCT116 cells was added to each of the wells in duplicates of the cell culture plates (T=0 and T=Final). 25 μL of Cell Titer Glo 2.0 reagent was added to each well of cell culture plate (T=0). The contents were mixed on an orbital shaker for 2 min and incubated at room temperature for 15 min to stabilize luminescent signal. Luminescence was recorded by Envision 2104 Multilabel Reader (PerkinElmer, Santa Clara, CA). The number of viable cells in culture was determined based on quantitation of the ATP present in each culture well. The cells in cell culture plate (T=Final) were incubated with the compounds at 37° C., 5% $CO_2$ for 72 hours. 25 μL of Cell Titer Glo 2.0 reagent was added to each well. The contents were mixed on an orbital shaker for 2 min and incubated at room temperature for 15 min to stabilize luminescent signal. Luminescence was recorded by Envision 2104 Multilabel Reader (PerkinElmer, Santa Clara, CA). The number of viable cells in culture was determined based on quantitation of the ATP present in each culture well. The GI50 curves were plotted using the GraphPad Prism 4 program based on a sigmoidal dose-response equation Y=Bottom+(Top−Bottom)/(1+10^((Log EC50−X)*HillSlope)). All parameters in the equation were calculated by GraphPad Prism 4 program. $GI_{50}$ is the concentration of the compound calculated according to $[(T_i-T_z)/(C-T_z)]*100=50$ where $T_i$ is the row data of cells with test compounds at T=Final; $T_z$ is the row data of cells without compounds at T=0 h; C is the row data of cells with control compound staurosporine (Sigma-Aldrich) at T=72 h. Accordingly, $GI_{50}$ is the value of $10^X$, where X was calculated by the Curve Fitting Equation when Y=50 using Excel.

Biological Example 3

S9 Stability Assays

Compounds were assessed for metabolic stability in human skin by assessing their rate of disappearance from human S9 skin fraction. Similarly, compounds were assessed for metabolic stability in human liver by assessing their rate of disappearance from human S9 liver fraction. The protocol below can be used to assess the difference between skin and hepatic metabolism.

The assay was carried out in 96-well microtiter plates at 37° C. Reaction mixtures (25 μL) contained a final concentration of 1 μM test compound, 2 mg/mL liver or skin S9 protein, and 1 mM NADPH in buffer (100 mM potassium phosphate, pH 7.4 buffer with 1 mM EDTA, 3 mM $MgCl_2$). At each of the time points (0, 15, 30, and 60 minutes), 150 μL of quench solution (100% acetonitrile with 0.1% formic acid) with internal standard was transferred to each well. Besides the zero minute controls, mixtures containing the same components except the NADPH were also prepared as the negative control. Verapamil or testosterone was included as a positive control to verify assay performance. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

The extent of metabolism was calculated as the disappearance of the test compound, compared to the 0-min control reaction incubations. Initial rates were calculated for the compound concentration and used to determine $t_{1/2}$ values and subsequently, the intrinsic clearance, $CL_{int}$= (0.693) ($1/t_{1/2}$ (min)) (mL incubation/mg of S9 protein).

Data for known, clinical MEK1 compounds ($C_1$-$C_7$) in this assay are provided below. Data for compounds within the scope of Formula (I) are provided in the Results section below.

| | Compound | Liver S9 $t_{1/2}$ (min) | CLint (μL/min/mg protein) |
|---|---|---|---|
| C1 | CI-1040 | 33 | 10.37 |
| C2 | PD-0325901 | 340 | 1.02 |
| C3 | Binemetinib | 277 | 1.25 |
| C4 | Selumetinib | 138 | 2.50 |

-continued

| | Compound | Liver S9 $t_{1/2}$ (min) | CLint (μL/min/mg protein) |
|---|---|---|---|
| C5 | GDC-0623 | 50 | 6.98 |
| C6 | Trametinib | 402 | 0.86 |
| C7 | Pimasertib | 268 | 1.29 |
| C8 | | 66 | 5.27 |
| C9 | | 158 | 2.20 |

Biological Example 4

Microsomal Stability Assay

Metabolic stability of testing compound can be evaluated using human liver microsomes to predict intrinsic clearance. Human liver microsomes are obtained from Corning Gentest.

The assay is carried out in 96-well microtiter plates at 37° C. Reaction mixtures (25 µL) contain a final concentration of 1 µM test compound, 0.5 mg/mL liver microsomes protein, and 1 mM NADPH in buffer (100 mM potassium phosphate, pH 7.4 buffer with 3 mM $MgCl_2$). At each of the time points (0, 15, 30, and 60 minutes), 150 µL of quench solution (100% acetonitrile with 0.1% formic acid) with internal standard is transferred to each well. Verapamil is included as a positive control to verify assay performance. Plates are sealed and centrifuged at 4° C. for 15 minutes at 4000 rpm. The supernatant is transferred to fresh plates for LC/MS/MS analysis.

All samples are analyzed on LC/MS/MS using an AB Sciex API 4000 instrument, coupled to a Shimadzu LC-20AD LC Pump system. Analytical samples are separated using a Waters Atlantis T3 dC18 reverse phase HPLC column (20 mm×2.1 mm) at a flow rate of 0.5 mL/min. The mobile phase consists of 0.1% formic acid in water (solvent A) and 0.1% formic acid in 100% acetonitrile (solvent B).

The extent of metabolism is calculated as the disappearance of the test compound, compared to the 0-min time incubation. Initial rates are calculated for the compound concentration and used to determine $t_1/2$ values and subsequently, the intrinsic clearance, $CL_{int}=(0.693)(1/t_{1/2} (min))$(g of liver/kg of body weight)(mL incubation/mg of microsomal protein)(45 mg of microsomal protein/g of liver weight).

Results for Biological Examples 1a, 2b, 2c, and 3

The following applies to the table below. NT indicates that the compound was not tested in a particular assay. Assay 1 is the biochemical MEK $IC_{50}$ (nM) assay as described in Biological Example 1a and as used for all tested compounds except compounds 8, 10, 12 and 13 which were tested using Biological Example 1b. Assay 2 is the A375 (BRAF) $GI_{50}$ (nM) cell-based assay as described in Biological Example 2c. Assay 3 is the HCT116 (Kras) $GI_{50}$ (nM) assay as described in Biological Example 2b. Assay 4 is the human liver S9 half-life stability assay as described in Biological Example 3. Assay 5 is the human liver S9 intrinsic clearance value (µL/min/mg protein) as described in Biological Example 3.

TABLE 2

| Ex. No. | Compound | Assay 1 | 2 | 3 | 4 | 5 |
|---|---|---|---|---|---|---|
| 2 | 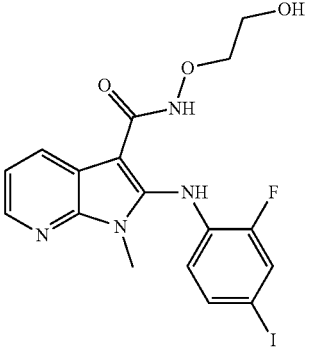 [SMILES: Cn1c(Nc2ccc(I)cc2F)c(C(=O)NOCCO)c2cccnc21] | 246 | 63 | 196 | 16 | 21.45 |
| 3 | 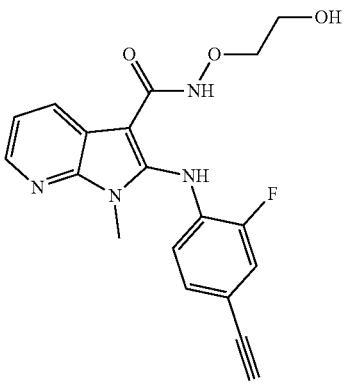 [SMILES: C#Cc1ccc(Nc2c(C(=O)NOCCO)c3cccnc3n2C)c(F)c1] | 2450 | NT | NT | NT | NT |

TABLE 2-continued

| Ex. No. | Compound | Assay 1 | 2 | 3 | 4 | 5 |
|---|---|---|---|---|---|---|
| 4 | | 671 | 809 | 5006 | 21 | 16.50 |
| 6 | | 371 | 81 | 448 | 90 | 3.85 |
| 7 | | 260 | 346 | 346 | 8 | 44.80 |
| 8 | | 243 | NT | NT | 34 | 10.27 |

TABLE 2-continued

| Ex. No. | Compound | Assay 1 | 2 | 3 | 4 | 5 |
|---|---|---|---|---|---|---|
| 10 | (S)-stereoisomer: 7-azaindole-3-carboxamide with N-O-CH(CH2OH)(CH2OH) side chain; 2-NH-(2-fluoro-4-iodophenyl); N1-methyl | 1770 | NT | NT | 96 | 3.59 |
| 12 | (R)-stereoisomer: 7-azaindole-3-carboxamide with N-O-CH(CH2OH)(CH2OH) side chain; 2-NH-(2-fluoro-4-iodophenyl); N1-methyl | 1780 | NT | NT | 105 | 3.29 |
| 13 | 7-azaindole-3-carboxamide (—NH2); 2-NH-(2-fluoro-4-iodophenyl); N1-methyl | 9610 | NT | NT | 23 | 15.37 |

Biological Example 5

In Vivo Model

Study Procedures: A topical formulation of a compound described herein along with a topical formulation of vehicle are applied to the skin of nude mice in duplicate. Skin is biopsied at discrete time intervals and bisected with half snap frozen in liquid nitrogen and half formalin fixed and paraffin embedded. Protein is isolated for Western blot analysis for p-ERK levels. p-ERK immunostaining is performed of FFPE sections for cell-specific analysis of p-ERK levels. Additional analysis includes H&E staining to investigate skin integrity.

A compound is assessed in suppressing p-ERK, a downstream biomarker of RAS/MAPK signaling in murine skin. In addition, proliferation of murine skin, apoptosis in murine skin, and histologic integrity of murine skin are also assessed.

Mice: 8 week old 129 mice obtained from Jackson laboratories are shaved prior to start of study. Approximately 21 mice were used for study. A compound is applied to the hairless dorsal skin of the mouse and at 12 hour intervals and skin biopsies are obtained prior to treatment, 24 hours, 72 hours and at 96 hours using 6 mm punch biopsies.

Western Blot analysis: For immunoblotting, epidermal skin is snap frozen in liquid nitrogen immediately after biopsy. The epidermis is lysed in lysis buffer and run on Western blots. Antibodies used for immunoblotting include rabbit anti-phospho-p44/42 MAPK (1:3000, Cell Signaling) and rabbit anti-p44/42 MAPK (1:3000, Cell Signaling), mouse anti-actin (1:5,000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry: Immunohistochemistry is performed on 5 µm paraffin sections. Antigen retrieval with enzyme treatment (1:1000) using standard protocols. Antibodies used were rabbit p-ERK (Cell Signaling, 4307S, 1:100). Bond Polymer Refine anti-rabbit HRP Detection (Leica Biosystems) was used according to manufacturer's protocol. Sections were then counterstained with hematoxylin, dehydrated and film coverslipped using a TissueTek-Prisma and Coverslipper (Sakura).

Histologic analysis: H&E is performed on 5 μM paraffin sections and tissue is examined to assess for cellular toxicity, inflammation or other changes in the integrity of murine skin.

Exogenous RAS activation in murine skin: The experiments are to be conducted in untreated murine skin. Alternatively, skin is pre-treated with TPA to enhance p-ERK levels. TPA-induced RAS/MAPK activation is performed with 96 hours of 12.5 uG TPA in 100 μL acetone to the skin of nude mice. Studies are performed 48 hours after TPA exposure.

T-test will be used to assess differences in p-ERK and Ki-67 in samples treated with topical MEK1 inhibitors compared to vehicle control.

Biological Example 6a

In Vivo Mouse Model

Compounds described herein are tested in a mouse model of NF1, e.g., genetically modified mouse model of NF1, a human dermal neurofibroma (or a cutaneous neurofibroma) xenograft to nude mouse model or both. For example, methods using the $Nf1^{flow/flox}$; Dhh-Cre mouse model described in Jousma et al. Pediatr. Blood Cancer 62: 1709-1716, 2015 can be used in this study. Magnetic resonance imaging (MRI) and volumetric measurements is used to measure tumor volumes.

Biological Example 6b

In Vivo Mouse Model

This study was designed to assess the skin toxicity and gross systemic toxicity of twice daily topical administration of a compound disclosed herein, as well as to evaluate the effect of metabolic lability on systemic toxicity.

Study Objective: The primary objective of this study was to characterize the skin and systemic toxicity of twice daily topical application of a compound disclosed herein, applied for 25 days in mice. Secondary objectives included determination of the 25-day skin and plasma compound levels of formulations containing three dosages of compound of Ex. 2 after application to 10% body surface area (BSA) murine skin; assessment of gross systemic toxicity from the application of compound of Ex. 2 after twice daily application to 10% BSA murine skin for 25 days; and determination of the correlation of skin and plasma compound levels with associated toxicity.

Duration: 25 days

Mice: 8 week old male $C_{57}BL/6J$ mice (Jackson Laboratories) were shaved prior to start of study and weekly. All experiments were approved by the Stanford University Animal Care and Use Committee.

Intervention Arms:

Compound application: Compounds were dissolved in a 50% DMSO/50% propylene glycol vehicle. 0.125 mL of the following compounds were applied to the shaved dorsal back of mice (10% BSA) twice daily for 5 days per week for a total of 24 days. The second dose was applied 8 hours after first morning dose. All mice were shaved once per week at application site.

Oral trametinib was dissolved in 0.5% hydroxypropyl methylcellulose (Sigma-Aldrich) and 0.2% Tween-80 (Sigma-Aldrich) and administered by oral gavage (0.2 mL bolus or 10 mg/kg) once daily 5 days per week. These mice were also shaved weekly.

Weekly (Weeks 0-4): body weight measurements weekly, starting week 0 until experiment end; photographs of dorsal back and face of each mouse weekly, starting week 0 until experiment end; skin; and gross stool analysis assessed weekly for heme color, starting week 0 until experiment end.

Week 4 (Experiment end): Skin and blood were collected right before the last morning dose (N=3), 1 hour (N=3 mice), and 2 hours (N=3 mice) after final application; Blood draw: Plasma compound levels (LCMS); Skin biopsy: formalin fixed for histology and p-ERK staining, flash frozen for Western analysis and skin compound levels (LCMS)

Oversight: The study was conducted with oversight from Stanford IACUC committee.

Skin biopsy and GI tract sampling: Skin was wiped down with 100% ethanol and a 1 cm² biopsy was obtained from compound application site each mouse at the 25 day end of experiment (except as noted below). The skin was biopsied prior to final dose from 3 mice, 1 hour after last compound application from 3 mice, 2 hours after last compound application from 3 mice. Half of the specimen were immediately flash frozen for LCMS analysis and Western Blot Analysis. Half of the specimen was fixed for 24 hours in 10% formalin and then transferred to ethanol for immunohistochemistry. Gastrointestinal tract was also formalin fixed overnight then transferred to 70% ETOH for storage.

Western Blot analysis: For immunoblotting, total skin biopsies were lysed in lysis buffer and run on Western blots. Antibodies used for immunoblotting included rabbit anti-phospho-p44/42 MAPK (1:3000, Cell Signaling) and rabbit anti-p44/42 MAPK (1:3000, Cell Signaling), rabbit anti-phospho-Mek1/2 (1:3000, Cell Signaling), mouse anti-actin (1:5000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry: Immunohistochemistry was performed on 5 μm paraffin sections.

Antigen retrieval was accomplished with enzymatic treatment. Sections were blocked with 10% normal goat serum and subsequently incubated in phospho-p44/42 MAPK (Erk1/2) rabbit monoclonal antibody (Cell Signaling) or mouse anti-Ki-67 (Pharmingen) at 1:100 dilution for 60

| Concentration | Cmpd | No. of mice | % BSA | Application |
| --- | --- | --- | --- | --- |
| 0 | Topical vehicle | 10 | 10 | Twice daily 5 days per week |
| 0 | Oral vehicle | 4 | N/A | Daily oral gavage 5x/week |
| 1% | trametinib | 10 | 10 | Twice daily 5 days per week |
| 0.1% | Cmpd of Ex. 2 | 9 | 10 | Twice daily 5 days per week |
| 0.5% | Cmpd of Ex. 2 | 9 | 10 | Twice daily 5 days per week |
| 1% | Cmpd of Ex. 2 | 9 | 10 | Twice daily 5 days per week |
| 0.75 mg/kg | trametinib | 10 | N/A | Daily oral gavage 5 x/week | minutes at room temperature. Detection was achieved with a peroxidase-conjugated anti-rabbit system (Leica Biosystem).

Histologic analysis: H&E was performed on 5 μM paraffin sections and tissue was examined to assess for cellular toxicity, inflammation or other changes in the integrity of murine skin.

Compound level analysis: Liquid chromatography with mass spectrometry method (LCMS) was used to detect compound levels in the skin and plasma. Tissues were preprocessed prior to LCMS as follows. Tissues were minced and incubated with collagenase and then finally homogenized using the stainless steel beads prior to LCMS analysis. Calibration curves and a QC test were run with each assay.

The study planned for the mice to be sacrificed at Day 25. However, at Day 18, several mice which were treated with topically-applied, 1% Trametinib were found dead, or had to be sacrificed due to unacceptable weight loss. The study was allowed to continue for the mice treated with Compound of Example 2 and for the mice treated with oral trametinib.

Results

Kaplan Meier curves were analyzed to determine progression to skin toxicity for each arm as compared with vehicle. T-test were used to compare compound levels at each dosage. Ki-67+ cells and p-ERK expression were also assessed on a cellular level via immunostaining. Western blots informed semi-quantitative changes in p-ERK expression.

See Table 3 which shows that topical application of compound of Example 2 demonstrated less systemic toxicity when compared to a topical application of Trametinib. All mice survived in the oral vehicle and skin vehicle arms. All mice survived in the following arms: topically applied 0.1%, 0.5%, and 1% formulations of compound of Example 2.

TABLE 3

Survival Rates

| | Day | | | | | | | | | |
|---|---|---|---|---|---|---|---|---|---|---|
| | 0 | 3 | 6 | 9 | 12 | 15 | 18 | 21 | 24 | 25 |
| oral vehicle | 100% | 100% | 100% | 100% | 100% | 100% | 100% | 100% | 100% | 100% |
| oral Trametinib | 100% | 90% | 70% | 70% | 70% | 70% | 70% | 70% | 70% | 70% |
| topical vehicle | 100% | 100% | 100% | 100% | 100% | 100% | 100% | 100% | 100% | 100% |
| topical - Cmpd of Ex. 2 (0.1%) | 100% | 100% | 100% | 100% | 100% | 100% | 100% | 100% | 100% | 100% |
| topical - Cmpd of Ex. 2 (0.5%) | 100% | 100% | 100% | 100% | 100% | 100% | 100% | 100% | 100% | 100% |
| topical - Cmpd of Ex 2. (1%) | 100% | 100% | 100% | 100% | 100% | 100% | 100% | 100% | 100% | 100% |
| topical Trametinib (1%) | 100% | 100% | 100% | 100% | 100% | 80% | 0% | 0% | 0% | 0% |

Provided below are plasma and skin levels of the compounds administered in this example. In the table below h refers to hours.

TABLE 4

Plasma LCMS Compound Levels (ng/mL)

| | Compound Levels | | | | |
|---|---|---|---|---|---|
| | 0.1% Cmpd of Ex. 2 | 0.5% Cmpd of Ex. 2 | 1% Cmpd of Ex. 2 | 1% trametinib | oral trametinib |
| pre-dose (16 h) | 1.18 | 4.78 | 24.98 | 1339.33 | 39.93 |
| 1 h | 173.65 | 1043.00 | 1020.33 | 2806.67 | 75.07 |
| 2 h | 37.93 | 102.17 | 262.33 | — | — |

TABLE 5

Compound Levels (μg/mL) in Neck/Back Skin

| | Compound levels (neck/back) | | | | |
|---|---|---|---|---|---|
| | 0.1% Cmpd of Ex. 2 | 0.5% Cmpd of Ex. 2 | 1% Cmpd of Ex. 2 | 1% trametinib | oral trametinib |
| pre-dose (16 h) | 5.62 | 49.17 | 14.73 | 4520.39 | — |
| 1 h | 13.98 | 288.79 | 682.77 | 3626.06 | — |
| 2 h | 4.88 | 81.62 | 377.95 | — | — |

Biological Example 7

Human Dermal Neurofibroma or Cutaneous Neurofibroma Explant Protocol

Dermal neurofibromas (or cutaneous neurofibromas) are benign tumors which develop in individuals affected with Neurofibromatosis-1 (NF1), a rare genetic disease caused by mutations in the NF1 gene, leading to downstream activation of the RAS/MAPK pathway. Recent studies have demonstrated that inhibition of MEK1 using systemic MEK inhibitors can suppress neurofibromas and other NF-1 related tumors in murine models. See, for example, *New Engl J Med* 2016, 375; 26; *J Clin Invest.* 2013, 123(1), 340-347; and *Pediatr Blood Cancer* 2015, 62(10), 1709-1716. This study establishes an in vitro neurofibroma explant model.

Study Objectives: The primary objective was to assess the efficacy of a topically-formulated compound described herein in suppressing p-ERK, a downstream biomarker of RAS/MAPK signaling in neurofibroma explants. The secondary objectives was to assess permeability (where the compound was applied topically) of neurofibroma explants treated with a compound described herein.

Sample Collection and Eligibility

Primary dermal neurofibromas or cutaneous neurofibromas were obtained from patients with clinical or genetic diagnoses of NF1. Discarded human neurofibromas samples were obtained from the Stanford Surgery Clinic, using an approved human subjects protocol (Stanford IRB #18325). Specimens were identified under the direction of the Principal Investigator and placed in cell proliferation media (DMEM/F12 containing penicillin/streptomycin (0.1%); fungizone (40 µg/mL); B27 (without vitamin A).

Patients had the following data to be enrolled in the study: Patient was older than 18 years of age; patient were not undergoing chemotherapy treatment at time of biopsy; and patients met clinical and/or genetic diagnosis of NF1 based on presence of two of the following:

1. Six or more café-au-lait macules over 5 mm in diameter in prepubertal individuals and over 15 mm in greatest diameter in postpubertal individuals.
2. Two or more neurofibromas of any type or one plexiform neurofibroma.
3. Freckling in the axillary or inguinal regions.
4. Two or more Lisch nodules (iris hamartomas).
5. Optic glioma.
6. A distinctive osseous lesion such as sphenoid dysplasia or thinning of long bone cortex, with or without pseudarthrosis.
7. First-degree relative (parent, sibling, or offspring) with NF-1 by the above criteria.

Study Procedures

Samples were primary, untreated neurofibromas of at least 6 mm in size; samples were excised by a shave, punch biopsy or elliptical excision; samples had a histologic diagnosis of dermal neurofibroma or cutaneous neurofibroma. Specimens were identified under the direction of the Principal Investigator Specimens were chopped into 2 mm fragments and placed in 24-well plates containing cell proliferation media (DMEM/F12 containing penicillin/streptomycin (0.1%); fungizone (40 µg/mL); B27 (without vitamin A) and submerged in media with drug. For topical gel application, samples were placed in 96 well plates with epidermal surface exposed to air.

For the data provided in FIG. 4, a topical gel formulation of a compound of Example 2, as well as a topical gel formulation of vehicle, were topically applied to the surface of human neurofibroma explants and harvested at 4 hours for analysis. The gel formulation was 1% hydroxypropyl cellulose in DMSO/PEG 400 1:1 (v/v). Harvested tissue was bisected and with half snap frozen and half fixed in 10% formalin and paraffin embedded for further analysis.

For the data provided in FIGS. 1-3, an explant sample was submerged in media and 5 µL of compound of Ex. 2 in 100% DMSO was added to media to make stated concentrations. Samples were harvested at 4 hours with half snap frozen in liquid nitrogen and half fixed in 10% formalin and paraffin embedded for histologic analysis.

Western Blot analysis: For immunoblotting, total skin biopsies were lysed in lysis buffer and run on Western blots. Antibodies used for immunoblotting included rabbit anti-phospho-p44/42 MAPK (1:3000, Cell Signaling) and rabbit anti-p44/42 MAPK (1:3000, Cell Signaling), rabbit anti-phospho-Mek1/2 (1:3000, Cell Signaling), mouse anti-actin (1:5000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry: Immunohistochemistry was performed on 5 µm paraffin sections. Antigen retrieval with enzyme treatment (1:1000) using standard protocols. Antibodies used were rabbit p-ERK (Cell Signaling, 4307S, 1:100). Bond Polymer Refine anti-rabbit HRP Detection (Leica Biosystems) was used according to manufacturer's protocol. Sections were then counterstained with hematoxylin, dehydrated and film coverslipped using a TissueTek-Prisma and Coverslipper (Sakura).

Data Analysis: Semi-quantative Western blot was used to assess differences in p-ERK in samples treated with a compound described herein compared to vehicle control.

Study Management: The study was conducted with oversight from an IRB with patient informed consent and HIPAA authorization.

Results

Figure 1B:
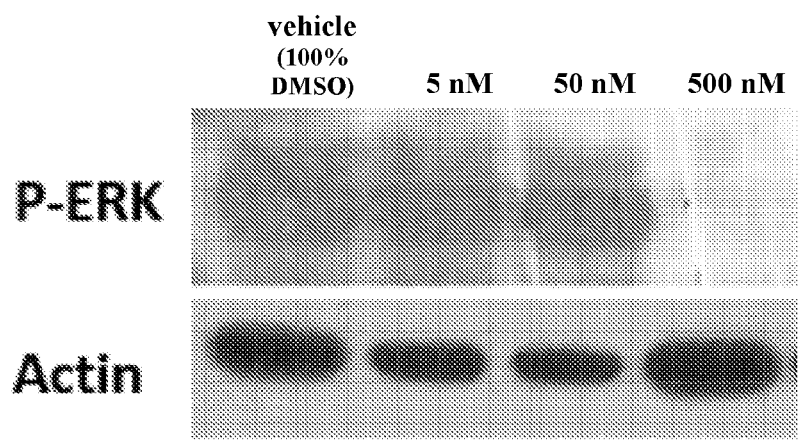

FIGS. 1a and 1b. demonstrate the suppression of pERK by the compound of Ex. 2 in human cutaneous neurofibroma (cNF) explants.

FIG. 2. demonstrates the suppression of p-ERK in human cNF explants with 500 nM of the compound of Ex. 2.

FIG. 3. demonstrates the dose-dependent suppression of p-ERK with the compound of Ex. 2 in human cNF explants.

FIG. 4. demonstrates that p-ERK was suppressed after application of a topical gel comprising Compound of Ex. 2 in Human cNF Explants.

Biological Example 8 hERG Screening Assay hERG screening was conducted using a procedure similar to the procedure described by Piper et al. (Piper, D. R. et al., *Assay Drug Dev. Technol.* 2008, 6(2):213-223). The Predictor hERG FP assay (available from ThermoFisher, cat. no. PV5365) is a homogenous, fluorescence polarization biochemical-based format utilizing a membrane fraction containing hERG channel protein (Predictor hERG Membrane) and a high affinity, red-fluorescent hERG channel ligand (Predictor hERG Tracer Red). When the Predictor hERG Tracer ligand is bound to the hERG channel it produces high fluorescence polarization values. Compounds that bind to the hERG channel protein (competitors) displace the Predictor hERG Tracer Red resulting in decreased fluorescence polarization values.

Test compounds were solubilized in DMSO at 100× (or greater) of the desired starting concentration. Screening was conducted with a final concentration of 1% DMSO. For 10-point titrations, 3-fold serial dilutions were performed from the starting concentrations. The assay buffer used was 25 mM HEPES (pH 7.5), 15 mM KCl, 1 mM MgCl2, and 0.05% Pluronic F-127 (available from Sigma-Aldrich).

Predictor hERG membranes were stored as a 2× stock at −80° C. Each membrane lot was titrated to identify the concentration of membranes required to obtain ~70% bound tracer. Before setting up the assay the membranes were thawed in a 37° C. water bath and stored at room temperature. To avoid light scatter caused by large membrane particulates the membranes were sonicated until a homogeneous solution free of particulates is obtained. Thawed membranes were sonicated with a Branson Sonifer® 450 for 10 pulses (Duty cycle: 20%, Output Control: 3 out of 10, Timer: hold). The sample was returned to ice for 30 seconds followed by another 5-10 pulses until homogeneous. After sonication the membranes were stored at room temperature.

The tracer (E-4031), selectively blocks hERG K+ channels, and is available from Sigma Aldrich. E-4031 was stored as a 250× stock at −20° C. Prior to the assay, the tracer was thawed and stored at room temperature. The tracer was diluted in Assay Buffer to 4× with a final assay concentration of 1 nM.

384 well untreated low-volume polystyrene microplates (Corning Cat. #4511) were used for the assay. To each well was added 5 µL of 4× test compound diluted in Assay Buffer (4% DMSO), or 200 nL 100× test compound in 100% DMSO. An additional 4.8 µL of Assay Buffer was added to the assay plate. Each compound titration was performed in the absence and presence of E-4031. 10 µL of 2× Predictor hERG Membranes was added to the appropriate wells of the assay plate. 5 µL of 4× Predictor hERG Tracer Red was added to the appropriate assay wells. The assay plate was shaken on an orbital shaker for 20-30 seconds. The assay plate was covered and incubated for 3 hours at room temperature. The assay plate was read on a fluorescence plate reader (Tecan Safire$^2$) and the data was analyzed.

Each plate was run with a control representing 100% tracer displacement (the minimum polarization value) as identified by 30 µM E-4031 displacement of Predictor hERG Tracer Red from Predictor hERG Membranes. Assay wells consisted of 30 µM E-4031, Predictor hERG Membranes and Predictor hERG Tracer Red with 1% DMSO.

Each plate also comprised a control representing 0% tracer displacement from the Predictor hERG Membranes (the maximum polarization value). Assay wells consisted of Assay Buffer, Predictor hERG Membranes, and Predictor hERG Tracer Red with 1% DMSO. Assay blank control wells consisted of Predictor hERG Membranes and Assay Buffer. The blank wells were used for background subtraction of raw parallel and perpendicular fluorescence values prior to the calculation of polarization values.

An 8-point titration of the known inhibitor, E-4031, in duplicate was included on each assay plate to ensure that the assay was performing within an expected $IC_{50}$ range.

The following controls were monitored for each concentration of test compound:

Test Compound Polarization Interference (TCPI): At higher concentrations some test compounds may exhibit an additional non-hERG specific reduction in polarization values producing data that appears to be affecting a one-site binding model. This phenomenon is observed with membranes lacking the hERG channel protein suggesting the presence of a non-hERG component in the membrane prep that is binding the tracer. This non-specific interaction is displaced by certain compounds at higher concentrations resulting in a reduction in polarization values. The effect of the test compound on this non-specific interaction was tested in the presence of saturating concentrations of E-4031. Assay wells utilized to test for Test Compound Polarization Interference contained test compound, 30 µM E-4031, Predictor hERG Membranes, and Predictor hERG Tracer Red with DMSO. Calculated TCPI values outside±25% were flagged.

Test Compound Fluorescence Interference (TCFI): Test Compound Fluorescence Interference was determined by comparing the total fluorescence for test compound wells with the total fluorescence values from the 00 and 1000 inhibition control wells. TCFI values outside±20% the controls were flagged. The following equations were used for each set of data points:

| | Equation |
|---|---|
| Background-Subtracted Perpendicular Fluorescence Intensity ($FI_\perp$) | $RFU_{Test\ Compound} - RFU_{Assay\ Blank}$ |
| Background-Subtracted Parallel Fluorescence Intensity ($FI_\parallel$) | G-Factor * $(RFU_{Test\ Compound} - RFU_{Assay\ Blank})$ |
| Total Fluorescence Intensity (TFI) | $FI_\parallel + (2 * FI_\perp)$ |
| Test Compound Fluorescence Interference (TCFI) | |
| If $TFI_{0\%\ Inhibition} > TFI_{100\%\ Inhibition}$ | |
| If $TFI_{Test\ Compound} > [Avg\ (TFI_{0\%\ Inhibition}) * 1.2]$ | $\left\{\dfrac{Avg\ TFI_{Test\ Compound}}{Avg\ TFI_{0\%\ Inhibition}} - 1\right\} * 100$ |
| If $TFI_{Test\ Compound} < [Avg\ (TFI_{0\%\ Inhibition}) * 1.2]$ And If $TFI_{Test\ Compound} > [Avg\ (TFI_{100\%\ Inhibition}) * 0.8]$ | 0 |
| If $TFI_{Test\ compound} < [Avg\ (TFI_{100\%\ Inhibition}) * 0.8]$ | $\left\{\dfrac{Avg\ TFI_{Test\ Compound}}{Avg\ TFI_{100\%\ Inhibition}} - 1\right\} * 100$ |
| If $TFI_{100\%\ Inhibition} > TFI_{0\%\ Inhibition}$ | |
| If $TFI_{Test\ Compound} > [Avg\ (TFI_{100\%\ Inhibition}) * 1.2]$ | $\left\{\dfrac{Avg\ TFI_{Test\ Compound}}{Avg\ TFI_{100\%\ Inhibition}} - 1\right\} * 100$ |
| If $TFI_{Test\ Compound} < [Avg\ (TFI_{100\%\ Inhibition}) * 1.2]$ And If $TFI_{Test\ Compound} > [Avg\ (TFI_{0\%\ Inhibition}) * 0.8]$ | 0 |

| Equation | |
|---|---|
| If $TFI_{Test\ Compound} < [Avg\ (TFI_{0\%\ Inhibition})* 0.8]$ | $\left\{\dfrac{Avg\ TFI_{Test\ Compound}}{Avg\ TFI_{0\%\ Inhibition}} - 1\right\} * 100$ |
| mP | $\dfrac{FI_{\parallel} + FI_{\perp}}{\parallel\ \ \perp} * 100$ |
| Test Compound Polarization Interference (TCPI) | $\left\{\dfrac{mP_{Test\ Compound+E-4031} - mP_{100\%\ Inhibition}}{mP_{0\%\ Inhibition} - mP_{100\%\ Inhibition}}\right\} * 100$ |
| % Inhibition | $\left\{1 - \dfrac{mP_{Test\ Compound} - mP_{Test\ Compound+E-4031}}{mP_{0\%\ Inhibition} - mP_{100\%\ Inhibition}}\right\} * 100$ |
| Z'* (using mP values) | $1 - \dfrac{3*Std\ Dev_{0\%\ Inhibition} + 3*Std\ Dev_{100\%\ Inhibition}}{Mean_{0\%\ Inhibition} - Mean_{100\%\ Inhibition}}$ |

Graphing Software: XLfit from IDBS was used for graphing. The dose response curve was curve fit to model number 205 (sigmoidal dose-response model). If the bottom of the curve did not fit between −20% and 20% inhibition, it was set to 0% inhibition. If the top of the curve did not fit between 70% and 130% inhibition, it was set to 100% inhibition.

The compound of Example 2 demonstrated an activity of >30 µM in this assay. Compound C9 demonstrated an activity of 7.3 µM in this assay. Compound C8 demonstrated an activity of 1.8 µM in this assay.

Biological Example 9

Calculated pKa pKa was calculated using Instant JChem, available from Chemaxon. The pyridine nitrogen of the compound of Example 2 provided a pKa value of 3.65. The pyridine nitrogen of compound C8:

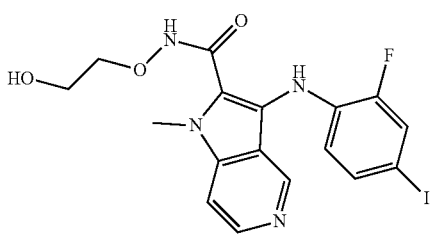 [SMILES: Cn1c(C(=O)NOCCO)c(Nc2ccc(I)cc2F)c2cnccc21]

provided a calculated pKa of 7.46. The difference in the calculated values is close to three log units, or almost 1000 fold.

Biological Example 10

MDCK-MDR1 Bi-Directional Transport Assay

MDCK-MDR1 is a stable-transfected cell line originating from MDCK cells, with over-expression of human MDR1 gene. The cell line is widely used for the identification and characterization of P-gp substrates and inhibitors.

MDCK-MDR1 cells were plated into 96-well Millipore Millicell-96 plates at 7,500 cells/75 µL/well and incubated for three days at 37° C. with 5% $CO_2$. Cells were washed with Hank's Balanced Salt Solution (HBSS) with 5 mM HEPES for 30 minutes before starting the experiment. Test compound solutions were prepared by diluting DMSO stock into HBSS buffer, resulting in a final DMSO concentration of 0.1%. Prior to the experiment, cell monolayer integrity was verified by transendothelial electrical resistance (TEER). Transport experiment was initiated by adding test compounds to the apical (75 µL) or basal (250 µL) side. Transport plates were incubated at 37° C. in a humidified incubator with 5% $CO_2$. Samples were taken from the donor and acceptor compartments after one hour and analyzed by liquid chromatography with tandem mass spectrometry (LC/MS/MS).

Digoxin was used as reference control.

Apparent permeability (Papp) values were calculated using the following equation: $Papp=(dQ/dt)/A/C_0$; where dQ/dt is the initial rate of amount of test compound transported across cell monolayer, A is the surface area of the filter membrane, and $C_0$ is the initial concentration of the test compound, calculated for each direction using a 4-point calibration curve by LC/MS/MS.

Net flux ratio between the two directional transports was calculated by the following equation: Ratio=Papp, $_{B-A}$/Papp, $_{A-B}$; where Papp, $_{B-A}$ and Papp, $_{A-B}$ represent the apparent permeability of test compound from the basal-to-apical and apical-to-basal side of the cellular monolayer, respectively.

Recovery was calculated based on the compound concentration at the end of the experiment, compared to that at the beginning of the experiment, adjusted for volumes.

A net flux ratio greater than two was considered a positive result for substrate determination. To further confirm whether the efflux activity observed for any test compounds is due to P-gp mediated transport, similar bi-directional transport studies in the presence of a potent P-gp inhibitor, such as GF120918, can be done. If the addition of a known P-gp inhibitor to the experiment reduces the net flux ratio by a significant amount (more than 50% reduction or reduces the ratio to close to unity), it is likely that the compound tested is a P-gp substrate.

| Compound | Concentration [μM] | Papp, A-B (×10⁻⁶ cm/s) Value | Papp, A-B (×10⁻⁶ cm/s) Mean | Papp, B-A (×10⁻⁶ cm/s) Value | Papp, B-A (×10⁻⁶ cm/s) Mean | Ratio B-A/ A-B | Recover Rate (%) |
|---|---|---|---|---|---|---|---|
| Digoxin | 5 | 1.3 1.6 | 1.5 | 14.6 14.1 | 14.3 | 9.7 | 96 |
| Cmpd of Ex. 2 | 5 | 50.5 47.8 | 49.1 | 42.3 41.3 | 41.8 | 0.9 | 92 |
| Cmpd C8 | 5 | 12.7 12.9 | 12.8 | 43.2 43.7 | 43.5 | 3.4 | 99 |

Biological Example 11

Metabolite Identification Study

Sample Processing: Compound was dissolved in dimethyl sulfoxide (DMSO) at 10 mM and tested at 20 μM.

Human Liver Microsomes (LM) Incubation: LM were thawed and diluted to 0.5 mg/mL with NADPH (1 mM), alamethicin (10 uM) and UDPGA (1 mM) solution before 0.5 mL was transferred to vials. 0 hr sample: the LM were incubated for 1 hr at 37° C., before 1 mL of quench solution (100% acetonitrile) was added to the vial and mixed well. Then, 1 μL of the stock solution was added to the vials. 1 hr sample: 1 μL of the stock solution was added to the vials with 0.5 mL diluted LM. The sample was incubated at 37° C. for 1 hr and quenched with 1 mL of 100% acetonitrile.

Samples were centrifuged and the supernatant was diluted with water and injected to LC-MS.

Metabolites were characterized by their mass spectronomy fragmentation pattern.

| Column Type: | Phenomenex Luna C18 150 × 2 mm, 5 μM |
|---|---|
| Mobile Phase: | A: water with 0.1% FA |
| | B: ACN with 0.1% FA |

| Pump Program: | Time (min) | B % |
|---|---|---|
| | 0 | 5 |
| | 0.3 | 5 |
| | 11 | 75 |
| | 12.95 | 95 |
| | 13 | 5 |
| | 15 | 5 |

| Flow Rate: | 0.35 mL/min |
|---|---|

Using the above conditions, at least masses of 368 and 457 were observed and are believed to correspond, respectively, to the following metabolites identified for Compound of Example 2:

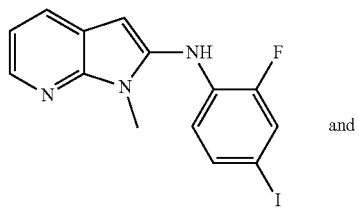

and

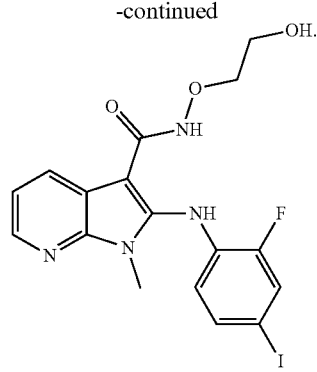

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A method of treating a MEK-inhibitor responsive disorder, MEK-inhibitor responsive dermal disorder, MEK-mediated disorder, or a MEK-mediated dermal disorder comprising administering to a subject in need thereof, a therapeutically effective amount of a compound of Formula (I):

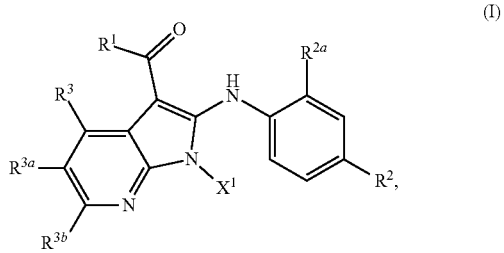

or an N-oxide, a stereoisomer, mixture of stereoisomers, and/or a pharmaceutically acceptable salt thereof, wherein:
  $R^1$ is —$OR^4$, —$NR^5R^{5a}$, or an N-linked heterocycloalkyl wherein the N-linked heterocycloalkyl is optionally substituted with one or two $R^{10}$;
  $R^{2a}$ is halo or $C_1$-$C_6$ alkyl;

R² is —S—C₁-C₆ alkyl, C₁-C₆ alkyl, C₂-C₆ alkenyl, C₂-C₆ alkynyl, or halo;

X¹ is C₁-C₆ alkyl;

R³, R³ᵃ, and R³ᵇ are independently hydrogen, C₁-C₆ alkyl, C₂-C₆ alkenyl, C₂-C₆ alkynyl, —S—C₁-C₆ alkyl, halo, C₁-C₆ alkoxy, C₃-C₈-cycloalkyloxy, heterocycloalkyloxy, heteroaryloxy, or phenoxy wherein each phenyl and heteroaryl is independently optionally substituted with 1, 2, or 3 R⁶;

R⁴ is C₁-C₆ alkyl, C₃-C₈ cycloalkyl, C₃-C₈ cycloalkylalkyl, C₁-C₆ hydroxyalkyl, or C₁-C₆ alkoxyalkyl;

R⁵ is hydrogen, C₁-C₆ alkyl optionally substituted with one heterocycloalkyl, C₃-C₈ cycloalkyl, C₃-C₈ cycloalkyl-C₁-C₆-alkyl-, C₁-C₆ hydroxyalkyl, C₁-C₆ alkoxy-C₁-C₆-alkyl, or —OR⁵ᵇ;

R⁵ᵃ is hydrogen or C₁-C₆ alkyl;

R⁵ᵇ is hydrogen, C₁-C₆ alkyl, C₃-C₈ cycloalkyl, C₃-C₈ cycloalkyl-C₁-C₆-alkyl, C₁-C₆ hydroxyalkyl, or C₁-C₆ alkoxy-C₁-C₆-alkyl;

each R⁶ is independently selected from the group consisting of carboxy, C₁-C₆-alkoxycarbonyl, C₁-C₆-alkyl, C₁-C₆-haloalkyl, C₁-C₆-alkoxy-C₁-C₆-alkyl, C₃-C₈ cycloalkyl, heterocycloalkyl, —OC(O)R⁷, —OS(O)₂R⁷, —O—C₁-C₆-haloalkyl, C₃-C₈ cycloalkyloxy, heterocycloalkyloxy, aryloxy, heteroaryloxy, amino, C₁-C₆-alkylamino, di-C₁-C₆-alkylamino, —NR⁸ᵃS(O)₂R⁸, —NR⁸ᵃC(O)R⁸, —S(O)₂R⁸, —S(O)₂NR⁸ᵃR⁸, —C(O)R⁸, —C(O)NR⁸ᵃR⁸, and —C₁-C₆-alkylene-R⁶ᵃ;

each R⁶ᵃ is independently selected from the group consisting of C₃-C₈ cycloalkyl, heterocycloalkyl, —NH₂, —NH(C₁-C₆-alkyl), —N(C₁-C₆-alkyl)₂, —NR⁹ᵃS(O)₂R⁹, —NR⁹ᵃC(O)R⁹, —S(O)₂R⁹, —S(O)₂NR⁹ᵃR⁹, —C(O)R⁹, and —C(O)NR⁹ᵃR⁹;

each R⁷ is independently selected from the group consisting of amino, C₁-C₆-alkylamino, di-C₁-C₆-alkylamino, C₁-C₆ alkyl, C₃-C₈ cycloalkyl, C₁-C₆-alkoxy, heterocycloalkyl, aryl, and heteroaryl;

each R⁸ᵃ and R⁹ᵃ is independently H or C₁-C₆ alkyl;

each R⁸ and R⁹ is independently C₁-C₆ alkyl, aryl, heteroaryl, C₃-C₈ cycloalkyl, or heterocycloalkyl; and each R¹⁰ is independently hydrogen, halo, hydroxy, oxo, C₁-C₆ alkyl, C₁-C₆ hydroxyalkyl, C₁-C₆ haloalkyl, amino-C₁-C₆-alkyl, C₁-C₆-alkylamino-C₁-C₆-alkyl, di-C₁-C₆-alkylamino-C₁-C₆-alkyl, C₁-C₆-alkoxy, C₃-C₈ cycloalkyl, heterocycloalkyl, or heteroaryl.

2. The method of claim 1, wherein the MEK-inhibitor responsive dermal disorder or a MEK-mediated dermal disorder is selected from the group consisting of a dermal rasopathy, a neurofibromatosis type 1, a cutaneous neurofibroma, a subdermal neurofibroma, and a superficial plexiform neurofibroma.

3. The method of claim 2, wherein the dermal rasopathy is selected from the group consisting of psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, pyogenic granuloma, sebaceous gland hyperplasia, cutaneous neurofibromas, seborrheic keratosis, sebaceous hyperplasia, seborrheic keratosis, and Multiple lentigines syndrome (formerly called Leopard syndrome).

4. The method of claim 1, wherein the compound is administered topically, subcutaneously, transdermally, intradermally, or intralesionally.

5. The method of claim 1, wherein X¹ is —CH₃.

6. The method of claim 1, wherein R³ and R³ᵇ are each hydrogen and R³ᵃ is C₁-C₆ alkyl, halo, or C₁-C₆ alkoxy.

7. The method of claim 1, wherein R³ and R³ᵇ are each hydrogen and R³ᵃ is methyl, fluoro, or methoxy.

8. The method of claim 1, wherein R³, R³ᵃ, and R³ᵇ are hydrogen.

9. The method of claim 1, wherein R² is —S—C₁-C₆ alkyl.

10. The method of claim 9, wherein R² is —SCH₃.

11. The method of claim 1, wherein R² is C₂-C₆ alkynyl.

12. The method of claim 11, wherein R² is C₂-C₃ alkynyl.

13. The method of claim 1, wherein R² is halo.

14. The method of claim 13, wherein R² is iodo.

15. The method of claim 1, wherein R²ᵃ is C₁-C₆ alkyl.

16. The method of claim 15, wherein R²ᵃ is methyl.

17. The method of claim 1, wherein R²ᵃ is halo.

18. The method of claim 17, wherein R²ᵃ is fluoro.

19. The method of claim 1, wherein R¹ is —NR⁵R⁵ᵃ and R⁵ is C₁-C₆ hydroxyalkyl.

20. The method of claim 1, wherein R¹ is —NR⁵R⁵ᵃ and R⁵ is —OR⁵ᵇ.

21. The method of claim 20, wherein R⁵ᵇ is C₃-C₈ cycloalkyl-C₁-C₆-alkyl.

22. The method of claim 20, wherein R⁵ᵇ is cyclopropylmethyl.

23. The method of claim 20, wherein R⁵ᵇ is C₁-C₆ hydroxyalkyl.

24. The method of claim 23, wherein R⁵ᵇ is an unbranched C₁-C₆ hydroxyalkyl.

25. The method of claim 23, wherein the C₁-C₆ alkyl in C₁-C₆ hydroxyalkyl is substituted with one hydroxy.

26. The method of claim 1, wherein R¹ is —NR⁵R⁵ᵃ and R⁵ᵃ is hydrogen.

27. The method of claim 1, wherein R¹ is —NH—O—CH₂CH₂OH.

28. The method of claim 1, wherein R¹ is —NH—O—CH₂(cyclopropyl).

29. The method of claim 1, wherein the compound is selected from the group consisting of:

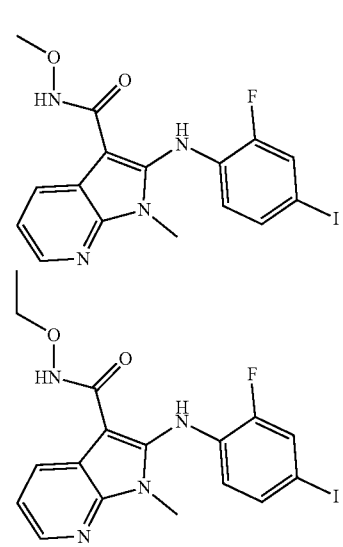

127
-continued
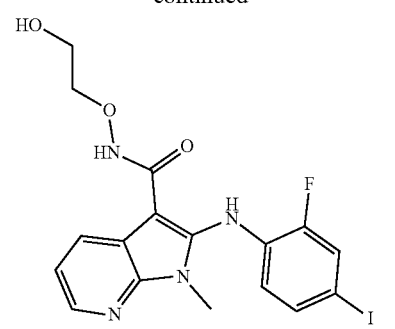
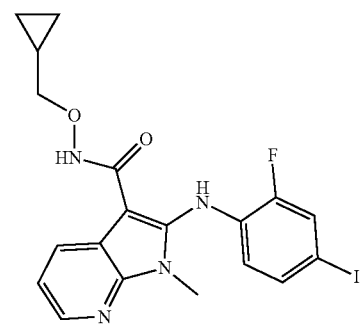
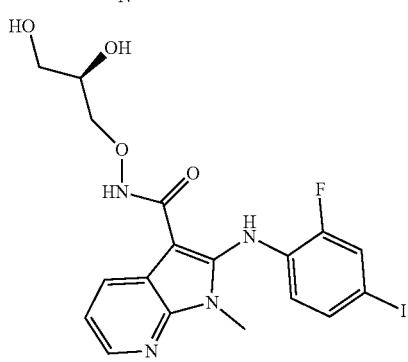
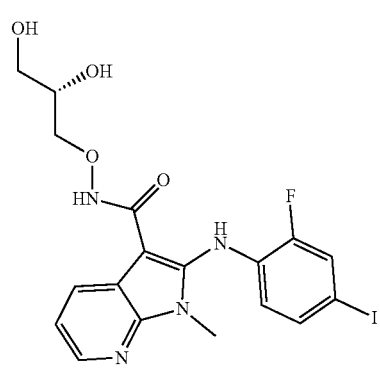
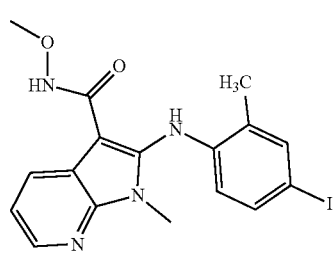
128
-continued
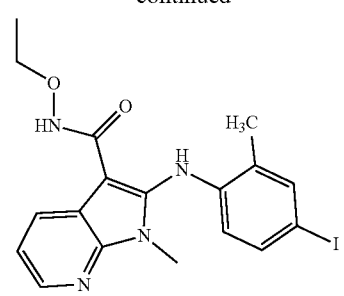
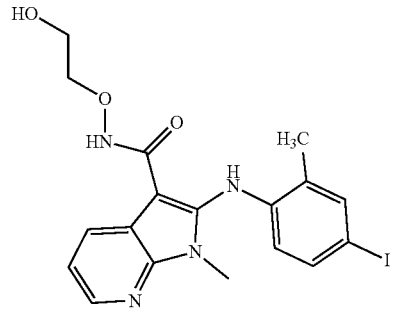
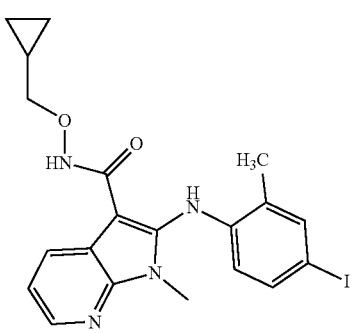
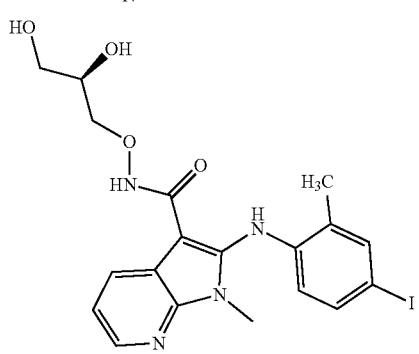
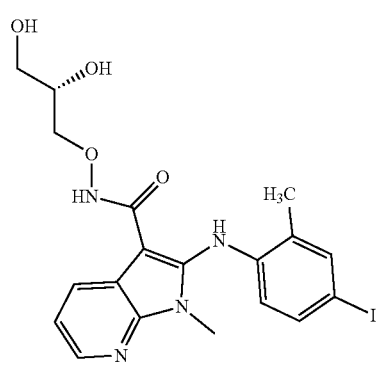

129
-continued
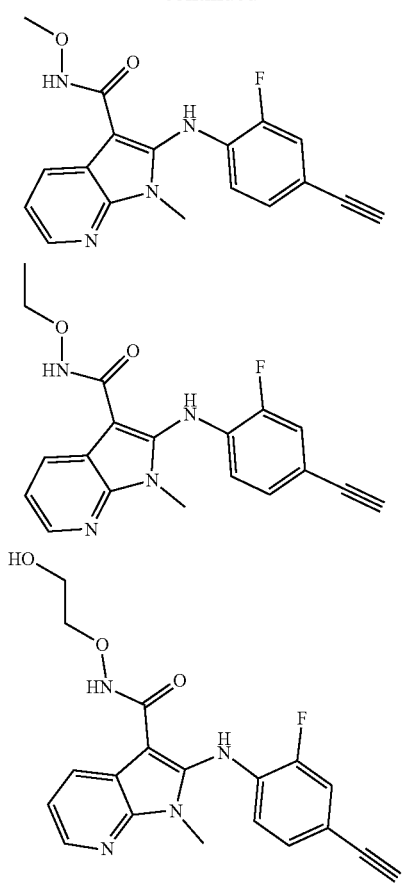
130
-continued
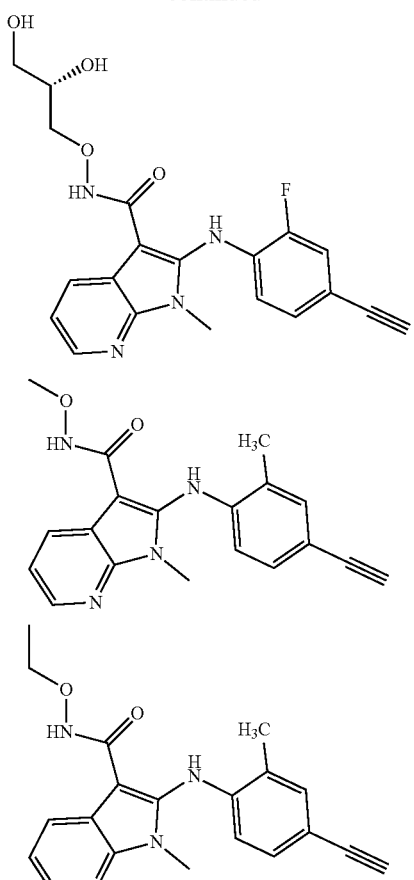
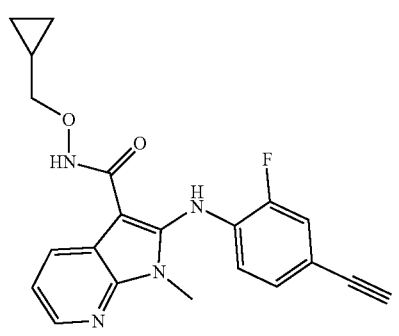
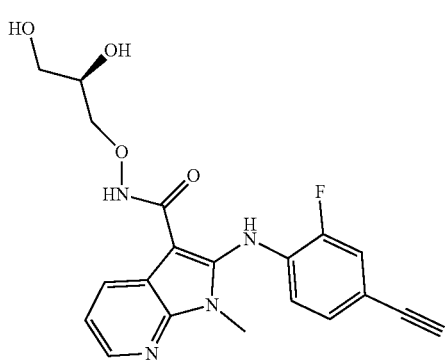
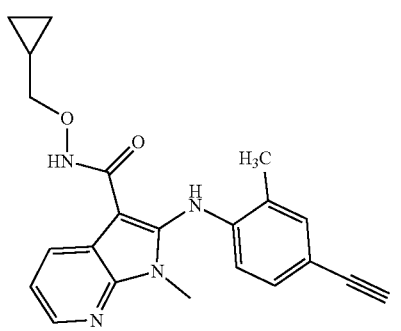

131
-continued
132
-continued
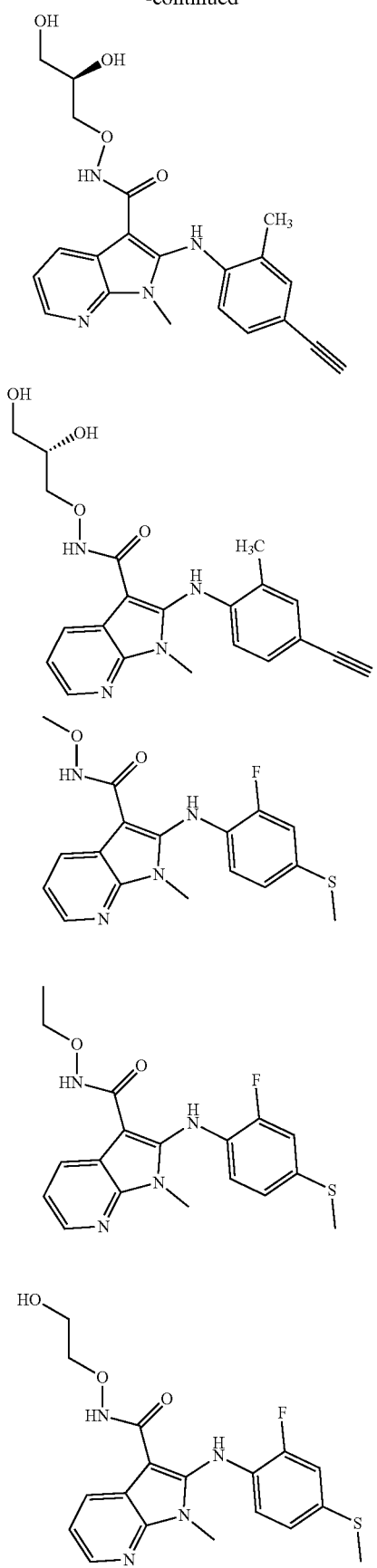
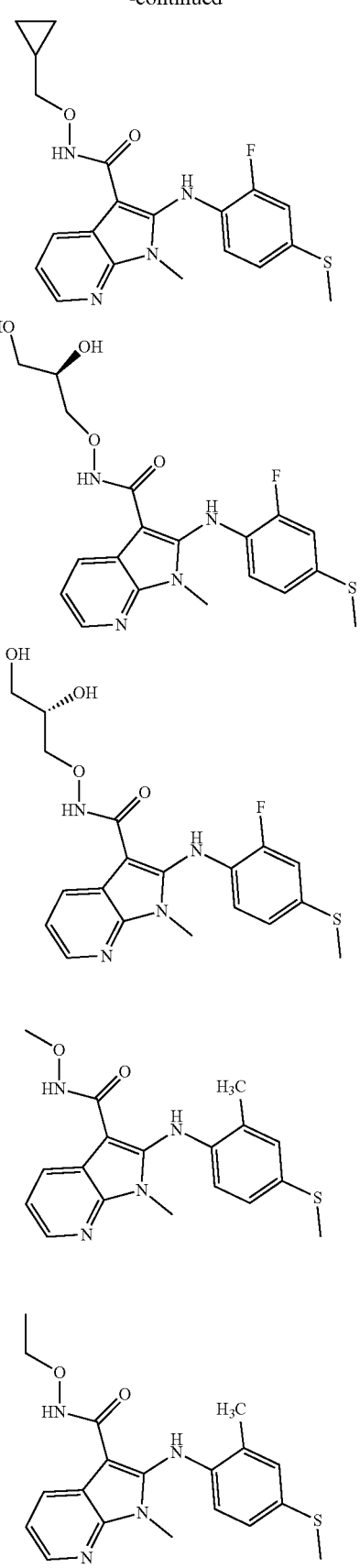

133
-continued
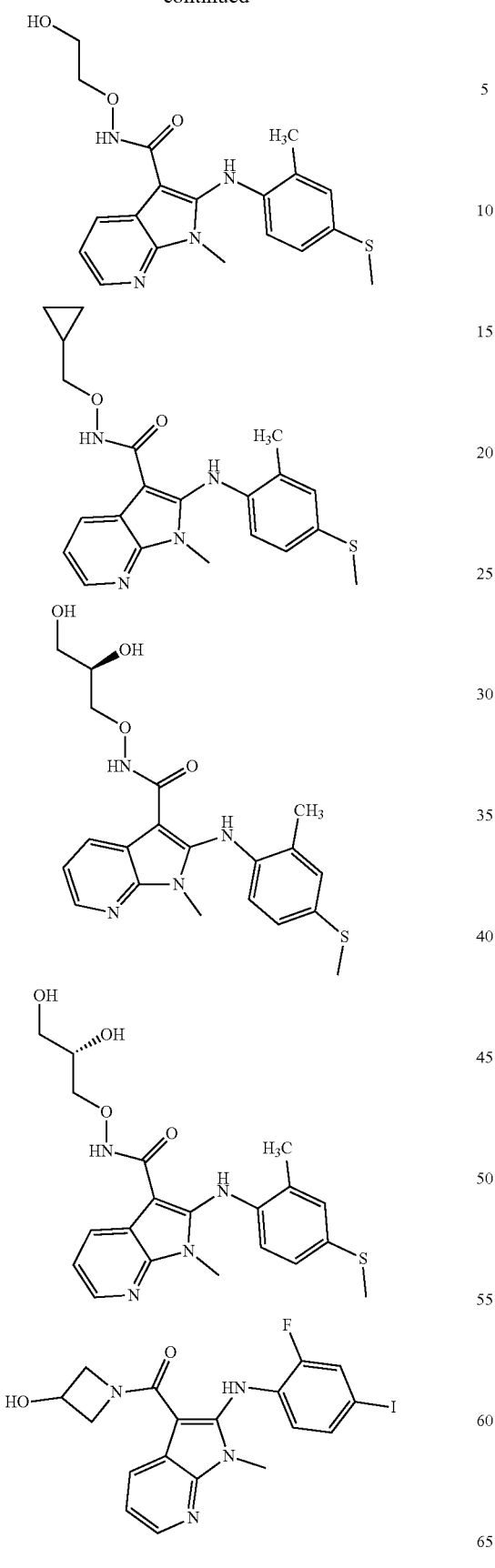
134
-continued
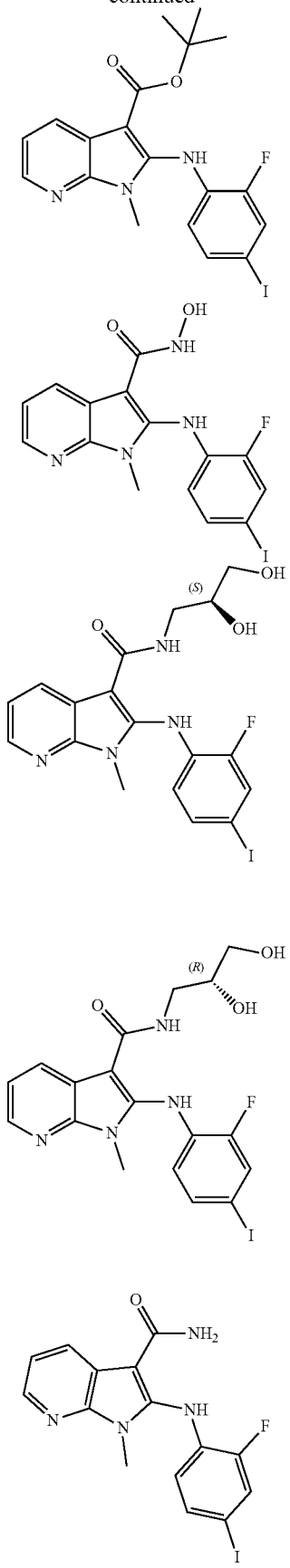

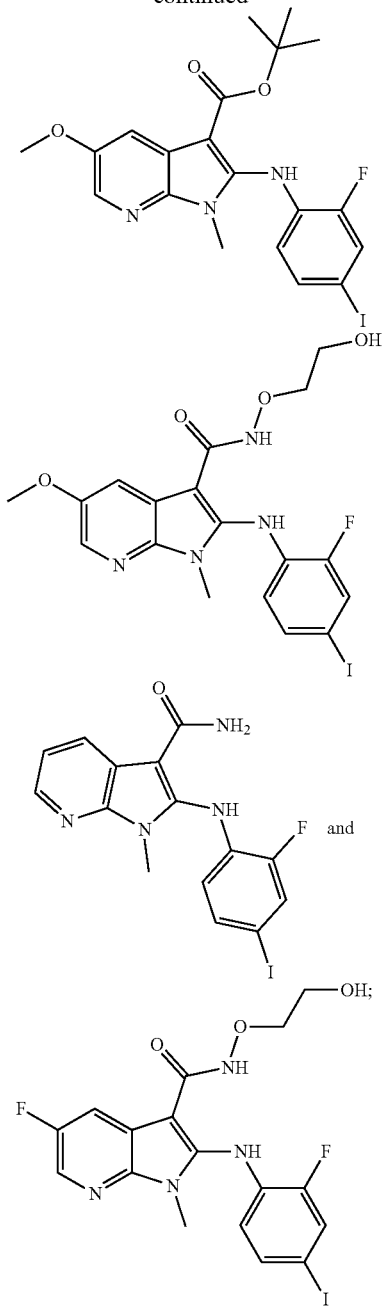

or a stereoisomer, mixture of stereoisomers, and/or a pharmaceutically acceptable salt thereof.

30. The method of claim 1, wherein the compound is selected from the group consisting of:

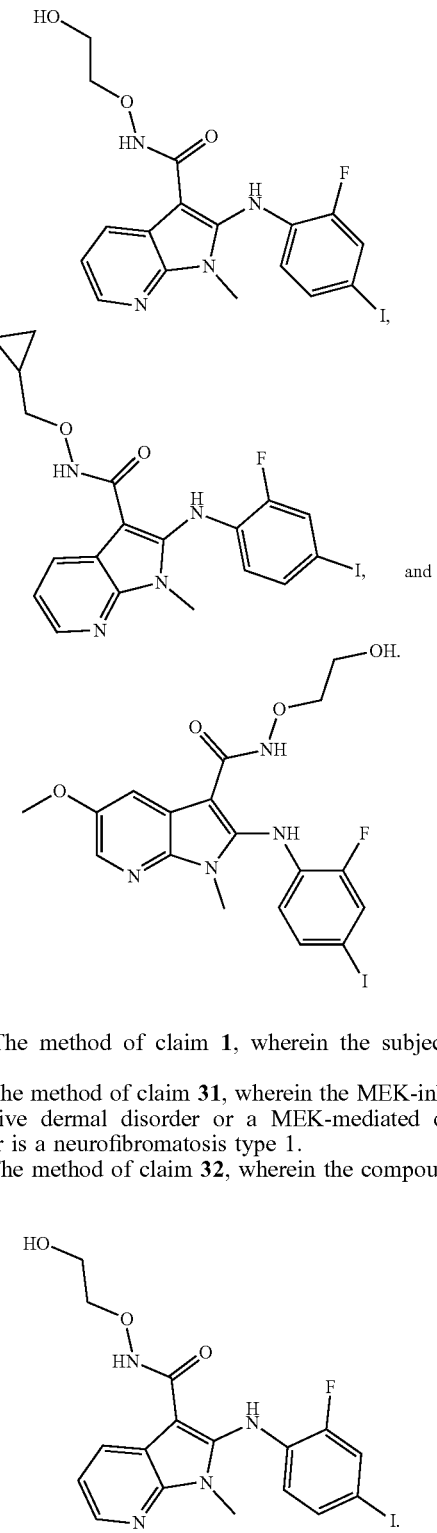

31. The method of claim 1, wherein the subject is a human.

32. The method of claim 31, wherein the MEK-inhibitor responsive dermal disorder or a MEK-mediated dermal disorder is a neurofibromatosis type 1.

33. The method of claim 32, wherein the compound is:

* * * * *